United States Patent
Faller et al.

(10) Patent No.: US 12,295,608 B2
(45) Date of Patent: May 13, 2025

(54) ROTATION FEATURES FOR ULTRASONIC SURGICAL INSTRUMENT

(71) Applicant: Cilag GmbH International, Zug (CH)

(72) Inventors: Craig N. Faller, Batavia, OH (US); Elizabeth DeBenedictis, Chicago, IL (US); William D. Kelly, Los Altos, CA (US); Michael R. Lamping, Cincinnati, OH (US); Timothy G. Dietz, Reading, MA (US); Patrick A. Weizman, Liberty Township, OH (US); Jacob S. Gee, Cincinnati, OH (US); John B. Schulte, West Chester, OH (US); Tylor C. Muhlenkamp, Cincinnati, OH (US); Douglas J. Turner, Cincinnati, OH (US); Eric B. Smith, Cincinnati, OH (US); Sean P. Conlon, Loveland, OH (US); Richard W. Timm, Cincinnati, OH (US); Jeffrey D. Messerly, Cincinnati, OH (US); Brian D. Bertke, Fort Thomas, KY (US)

(73) Assignee: Cilag GmbH International, Zug (CH)

( * ) Notice: Subject to any disclaimer, the term of this patent is extended or adjusted under 35 U.S.C. 154(b) by 203 days.

(21) Appl. No.: 17/831,598

(22) Filed: Jun. 3, 2022

(65) Prior Publication Data
US 2022/0361911 A1    Nov. 17, 2022

Related U.S. Application Data

(60) Continuation of application No. 16/429,122, filed on Jun. 3, 2019, now Pat. No. 11,389,190, which is a
(Continued)

(51) Int. Cl.
*A61B 17/32*     (2006.01)
*A61B 17/00*     (2006.01)
(Continued)

(52) U.S. Cl.
CPC .............. *A61B 17/320092* (2013.01); *A61B 2017/00026* (2013.01); *A61B 2017/2825* (2013.01);
(Continued)

(58) Field of Classification Search
CPC ............ A61B 17/32; A61B 17/320092; A61B 17/320068; A61B 2017/320094;
(Continued)

(56) References Cited

U.S. PATENT DOCUMENTS

| 5,322,055 A | 6/1994 | Davison et al. |
| 5,873,873 A | 2/1999 | Smith et al. |

(Continued)

FOREIGN PATENT DOCUMENTS

| CN | 103381108 A | 11/2013 |
| EP | 2221011 A2 | 8/2010 |

(Continued)

OTHER PUBLICATIONS

Chinese Search Report dated Mar. 20, 2018, for Application No. 201480075683.5, 2 pages.
(Continued)

*Primary Examiner* — Vi X Nguyen
(74) *Attorney, Agent, or Firm* — Frost Brown Todd LLP

(57) ABSTRACT

An apparatus includes a shaft assembly, an ultrasonic blade, and a clamp assembly. The shaft assembly includes an acoustic waveguide operable to transmit ultrasonic vibrations to the blade. The clamp assembly includes a clamp arm pivotable toward and away from the blade about a pivot axis, to clamp tissue between the clamp arm and the blade. A rotation feature may provide rotation of the blade relative to the clamp arm about the longitudinal axis of the waveguide. Alternatively, the rotation feature may provide rotation of the clamp arm relative to the blade about the longitudinal
(Continued)

axis. The rotation feature may be driven based on pivotal positioning of the clamp arm relative to the blade about the pivot axis. The rotation feature may selectively lock and unlock the angular position of either the blade or the clamp arm about the longitudinal axis at any of a number of predetermined angular positions.

20 Claims, 65 Drawing Sheets

Related U.S. Application Data continuation of application No. 15/680,495, filed on Aug. 18, 2017, now Pat. No. 10,470,792, which is a division of application No. 14/109,013, filed on Dec. 17, 2013, now Pat. No. 9,743,946.

(51) Int. Cl.
*A61B 17/28* (2006.01)
*A61B 17/29* (2006.01)
*A61B 90/00* (2016.01)

(52) U.S. Cl.
CPC .............. *A61B 2017/2929* (2013.01); *A61B 2017/2947* (2013.01); *A61B 2017/320072* (2013.01); *A61B 2017/320075* (2017.08); *A61B 2017/320088* (2013.01); *A61B 2017/320093* (2017.08); *A61B 2017/320094* (2017.08); *A61B 2017/320095* (2017.08); *A61B 2090/0811* (2016.02)

(58) Field of Classification Search
CPC ....... A61B 2017/320093; A61B 2017/320095; A61B 2017/320075; A61B 17/00; A61B 2017/00026; A61B 2017/2825
See application file for complete search history.

(56) References Cited

U.S. PATENT DOCUMENTS

| | | | |
|---|---|---|---|
| 5,893,835 A | 4/1999 | Witt et al. | |
| 5,944,737 A | 8/1999 | Tsonton et al. | |
| 5,980,510 A | 11/1999 | Tsonton et al. | |
| 6,139,561 A | 10/2000 | Shibata et al. | |
| 6,325,811 B1 | 12/2001 | Messerly | |
| 6,458,142 B1 | 10/2002 | Faller et al. | |
| 6,669,690 B1 | 12/2003 | Okada et al. | |
| 6,773,444 B2 | 8/2004 | Messerly | |
| 6,783,524 B2 | 8/2004 | Anderson et al. | |
| 7,520,865 B2 | 4/2009 | Young et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,894,674 B2 | 11/2014 | Balanev et al. | |
| 8,936,614 B2 | 1/2015 | Allen | |
| 8,986,302 B2 | 3/2015 | Aldridge et al. | |
| 9,023,071 B2 | 5/2015 | Miller et al. | |
| 9,060,775 B2 | 6/2015 | Weiner et al. | |
| 9,095,367 B2 | 8/2015 | Olsen et al. | |
| 9,381,058 B2 | 7/2016 | Houser et al. | |
| 9,386,983 B2 | 7/2016 | Swensgard et al. | |
| 9,393,037 B2 | 7/2016 | Olson et al. | |
| 9,675,375 B2 | 6/2017 | Houser et al. | |
| 9,743,946 B2 | 8/2017 | Faller et al. | |
| 10,470,792 B2 | 11/2019 | Faller et al. | |
| 11,389,190 B2 | 7/2022 | Faller et al. | |
| 2006/0058825 A1* | 3/2006 | Ogura | A61B 17/320092 606/169 |
| 2006/0079874 A1 | 4/2006 | Faller et al. | |
| 2007/0173871 A1* | 7/2007 | Houser | A61B 17/320092 606/169 |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0063525 A1 | 3/2010 | Beaupre et al. | |
| 2010/0331873 A1 | 12/2010 | Dannaher et al. | |
| 2011/0087256 A1 | 4/2011 | Wiener et al. | |
| 2012/0078139 A1 | 3/2012 | Aldridge et al. | |
| 2012/0078278 A1* | 3/2012 | Bales, Jr. | A61B 17/320092 307/116 |
| 2012/0116263 A1 | 5/2012 | Houser et al. | |
| 2012/0116265 A1 | 5/2012 | Houser et al. | |
| 2013/0116717 A1 | 5/2013 | Balek et al. | |
| 2015/0080924 A1 | 3/2015 | Stulen et al. | |
| 2015/0080925 A1 | 3/2015 | Schulte et al. | |

FOREIGN PATENT DOCUMENTS

| | | |
|---|---|---|
| JP | 2000-312682 A | 11/2000 |
| JP | 2001-037769 A | 2/2001 |
| JP | 2010-167204 A | 8/2010 |
| WO | WO 2013/183715 A1 | 12/2013 |
| WO | WO 2013/062103 A1 | 4/2015 |

OTHER PUBLICATIONS

Chinese Office Action dated Feb. 22, 2019, for Application No. 201480075683.5, 9 pages.
European Decision to Grant dated Oct. 19, 2017, for Application No. 14824216.7, 2 pages.
International Search Report and Written Opinion dated May 19, 2015, for International Application No. PCT/US2014/069036, 16 pages.
Japanese Notification of Reasons for Refusal and Search Report dated Sep. 4, 2018, for Application No. JP 2016-540551, 16 pages.
Japanese Decision to Grant a Patent dated Jan. 22, 2019, for Application No. 2016-540551, 2 pages.
U.S. Appl. No. 61/410,603, entitled "Energy-Based Surgical Instruments," filed Nov. 5, 2010.

* cited by examiner

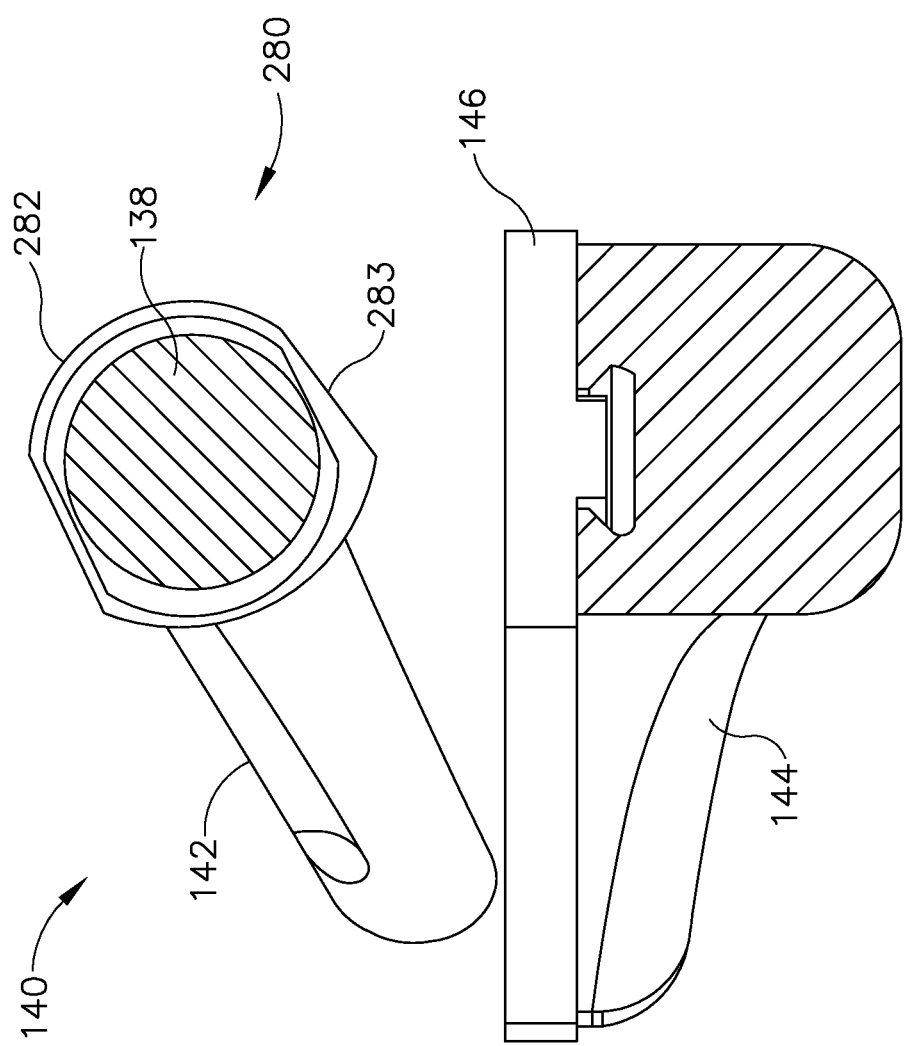

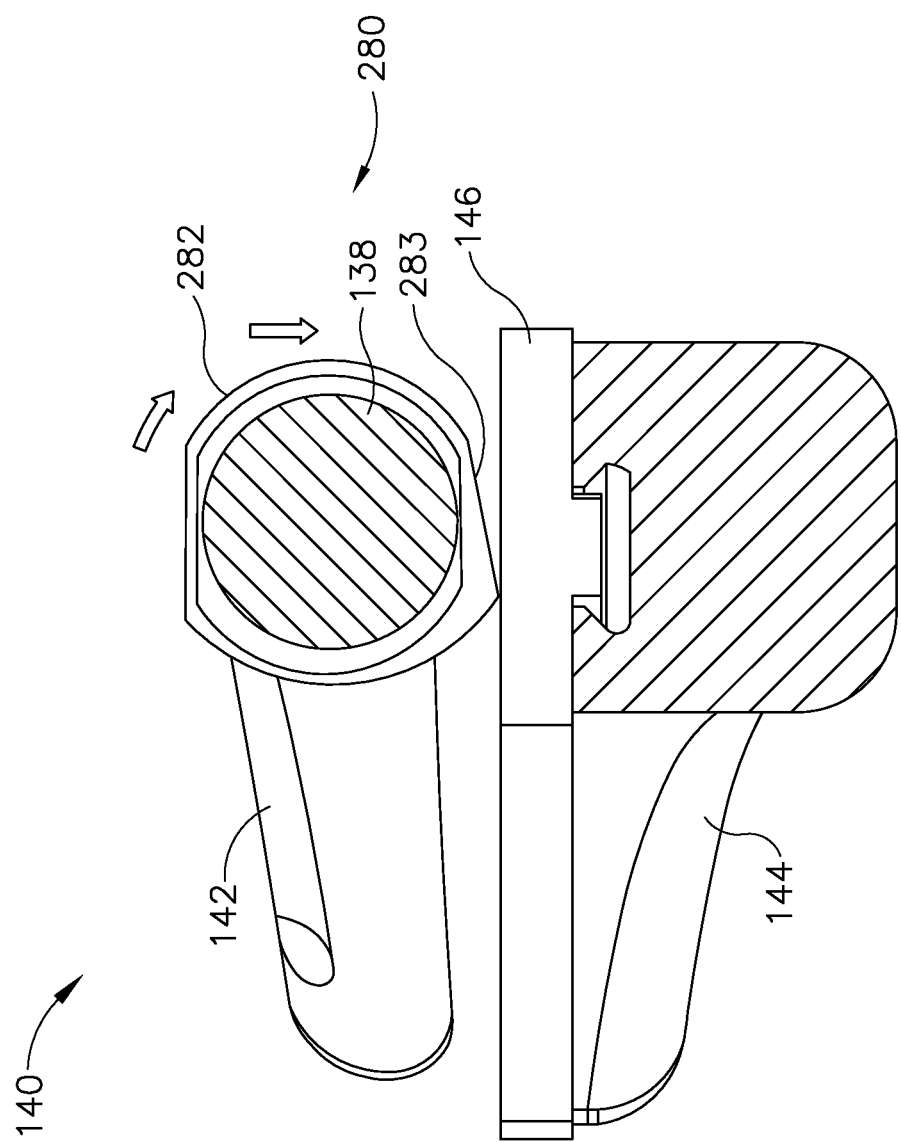

ROTATION FEATURES FOR ULTRASONIC SURGICAL INSTRUMENT

This application is a continuation of U.S. application Ser. No. 16/429,122, filed Jun. 3, 2019, and published as U.S. Pat. Pub. No. 2019/0350616 on Nov. 21, 2019, entitled "Rotation Features for Ultrasonic Surgical Instrument," issued as U.S. Pat. No. 11,389,190 on Jul. 19, 2022, which is a continuation of U.S. application Ser. No. 15/680,495, filed Aug. 18, 2017, issued as U.S. Pat. No. 10,470,792 on Nov. 12, 2019, entitled "Rotation Features for Ultrasonic Surgical Instrument," which is a divisional of U.S. application Ser. No. 14/109,013, filed Dec. 17, 2013, issued as U.S. Pat. No. 9,743,946 on Aug. 29, 2017, entitled "Rotation Features for Ultrasonic Surgical Instrument."

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, now U.S. Pat. No. 8,623,027, issued on Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; U.S. Pub. No. 2012/0029546, entitled "Ultrasonic Surgical Instrument Blades," published Feb. 2, 2012, now U.S. Pat. No. 8,591,536, issued on Nov. 26, 2013, the disclosure of which is incorporated by reference herein; and U.S. patent application Ser. No. 14/031,665, entitled "Alignment Features for Ultrasonic Surgical Instrument," filed Sep. 19, 2013, published as U.S. Pub. No. 2015/0080925 on Mar. 19, 2015, now abandoned, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued on Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," now U.S. Pat. No. 9,095,367, issued on Aug. 4, 2015, the disclosure of which is incorporated by reference herein.

Some ultrasonic surgical instruments may include a clamping feature to compress tissue against the ultrasonic blade of the end effector. Examples of such an arrangement (sometimes referred to as a clamp coagulator shears or an ultrasonic transector) are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; and U.S. Pat. No. 6,325,811, entitled "Blades with Functional Balance Asymmetries for use with Ultrasonic Surgical Instruments," issue Dec. 4, 2001, the disclosure of which is incorporated by reference herein. Some versions of clamp coagulator shears utilize handles that are of either a pistol or scissors grip design. The scissor grip designs may have one thumb or finger grip that is immovable and fixed to the housing; and one movable thumb or finger grip. Some designs have scissor arms that extend from the grips, with one of the arms rotating around a fixed pivot or rotation point that is perpendicular to the longitudinal axis of the working element. The pistol grip designs may have a trigger that is pivotable toward and away from a pistol grip to pivotally drive a clamp arm. The operator may thus squeeze a handgrip or other feature to drive the clamp arm, to thereby pivot the clamp pad toward the blade.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 15A depicts a cross-sectional view of the instrument of FIG. 14, with the instrument in an open configuration and with an ultrasonic blade in a first rotational position;

FIG. 15B depicts a cross-sectional view of the instrument of FIG. 14, with the instrument moved into a partially closed configuration and with the ultrasonic blade rotated into a second rotational position;

Figure 1:
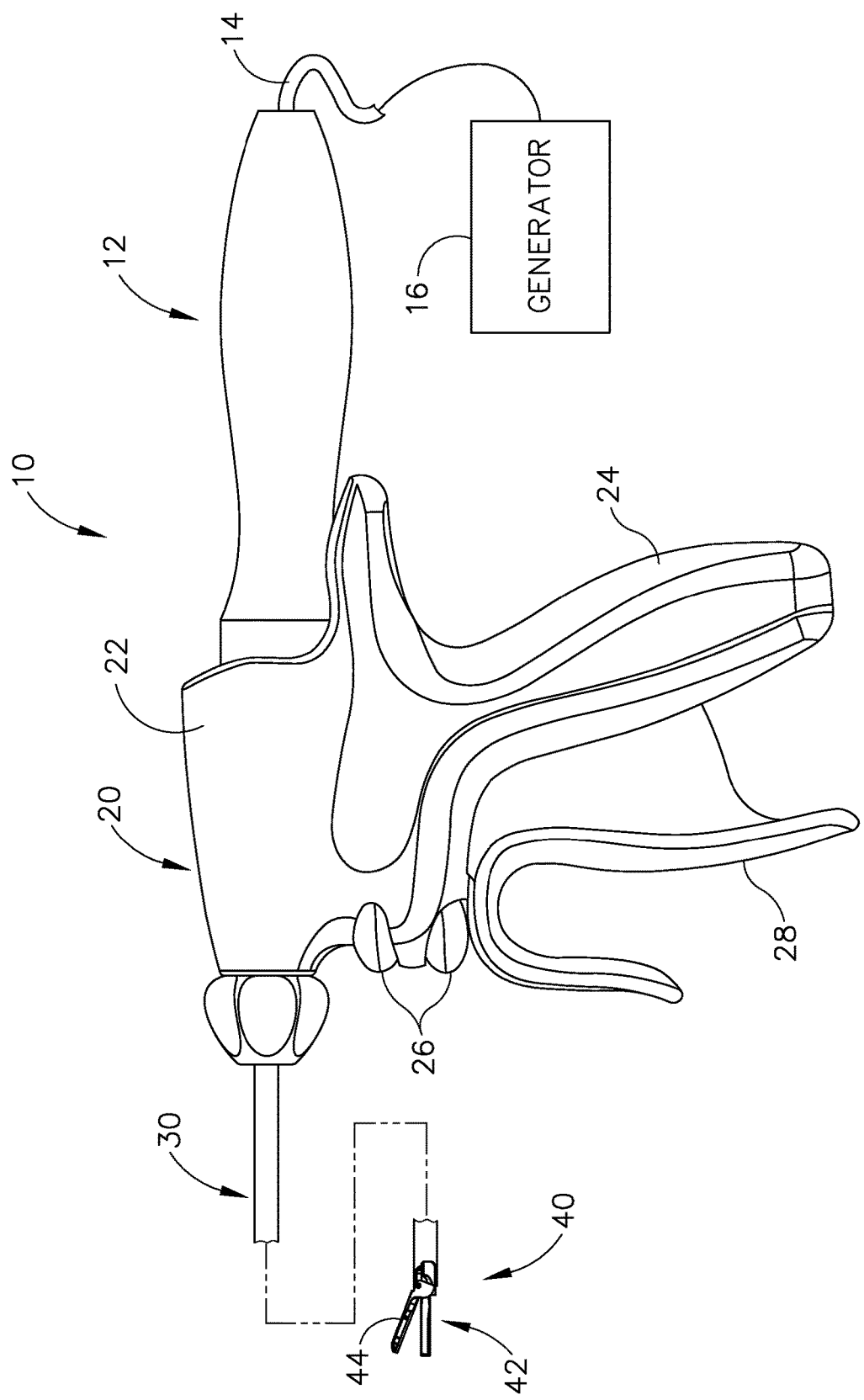
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIGS. 1-6B illustrate exemplary ultrasonic surgical instruments (10, 100). At least part of each instrument (10, 100) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, now U.S. Pat. No. 8,623,027, issued on Jan. 7, 2014; U.S. Pub. No. 2010/0069940, now U.S. Pat. No. 9,023,071, issued on May 5, 2015; U.S. Pub. No. 2011/0015660, now U.S. Pat. No. 8,461,744, issued on Jun. 11, 2013; U.S. Pub. No. 2012/0112687, now U.S. Pat. No. 9,381,058, issued on Jul. 5, 2016; U.S. Pub. No. 2012/0116265, now abandoned; U.S. patent application Ser. No. 13/538,588, now U.S. Pat. No. 9,393,037, issued on Jul. 19, 2016; U.S. patent application Ser. No. 13/657,553, now U.S. Pat. No. 9,095,367, issued on Aug. 4, 2015; U.S. Pat. App. No. 61/410,603; and/or U.S. patent application Ser. No. 14/028,717, now U.S. Pat. No. 10,172,636, issued on Jan. 8, 2019. The disclosures of each of the foregoing patents, publications, and applications are incorporated by reference herein. As described therein and as will be described in greater detail below, each instrument (10, 100) is operable to cut tissue and seal or weld tissue (e.g., a blood vessel, etc.) substantially simultaneously. It should also be understood that instruments (10, 100) may have various structural and functional similarities with the HARMONIC ACER Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instruments (10, 100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instruments (10, 100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
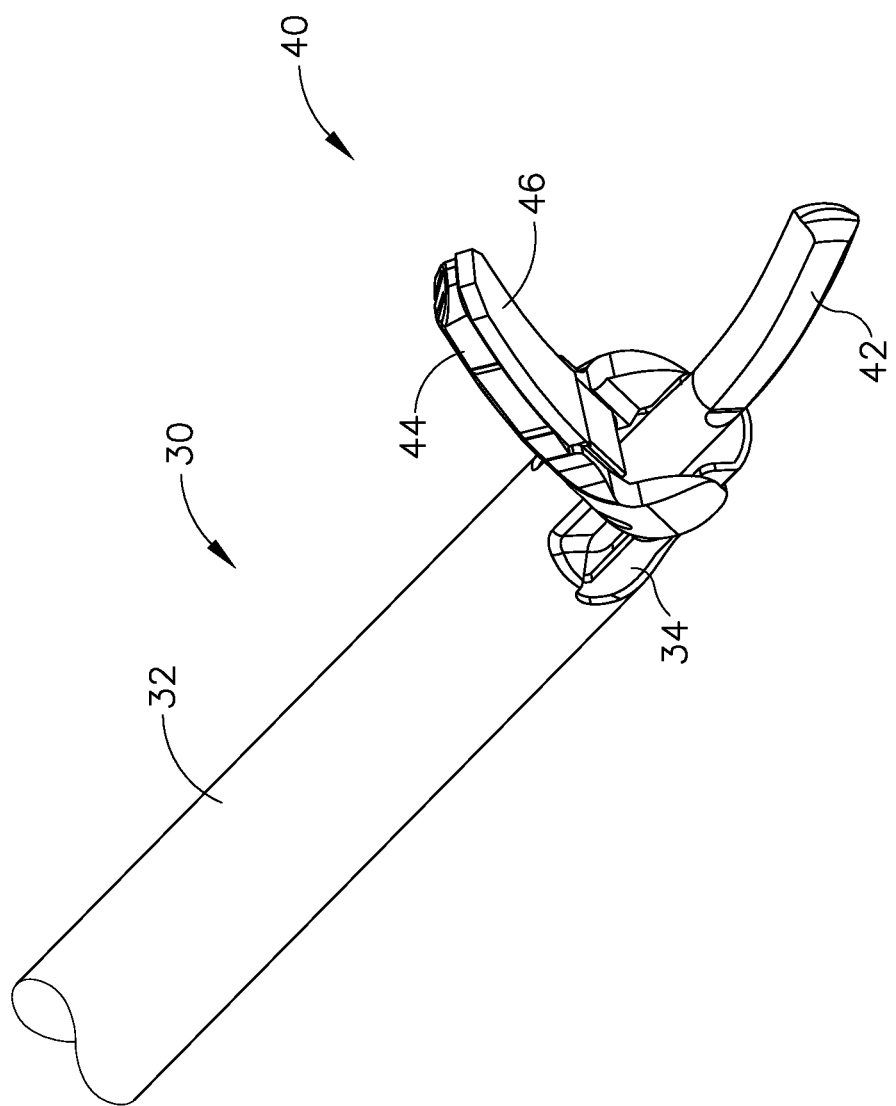
FIG. 2 depicts a perspective view of the end effector of the instrument of FIG. 1, in an open configuration.

A. Exemplary Ultrasonic Surgical Instrument for Minimally Invasive Surgical Procedures FIG. 1 illustrates an exemplary ultrasonic surgical instrument (10) that is configured to be used in minimally invasive surgical procedures (e.g., via a trocar or other small diameter access port, etc.). Instrument (10) of this example comprises a handle assembly (20), a shaft assembly (30), and an end effector (40). As shown in FIGS. 2-3B, shaft assembly (30) comprises an outer sheath (32), an inner tube (34) slidably disposed within outer sheath (32), and a waveguide (38) disposed within inner tube (34). As will be discussed in more detail below, longitudinal translation of inner tube (34) relative to outer sheath (32) causes actuation of clamp arm (44) at end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. In the present example, a resilient member biases trigger (28) away from pistol grip (24). Trigger (28) is pivotable toward pistol grip (24) to drive inner tube (34) proximally relative to outer sheath (32). When trigger (28) is thereafter released or driven away from pistol grip (24), inner tube (34) is driven distally relative to outer sheath (32). By way of example only, trigger (28) may be coupled with inner tube (34) in accordance with the teachings of various references cited herein. Other suitable ways in which trigger (28) may be coupled with inner tube (34) will be apparent to those of ordinary skill in the art in view of the teachings herein.

Figure 3A:
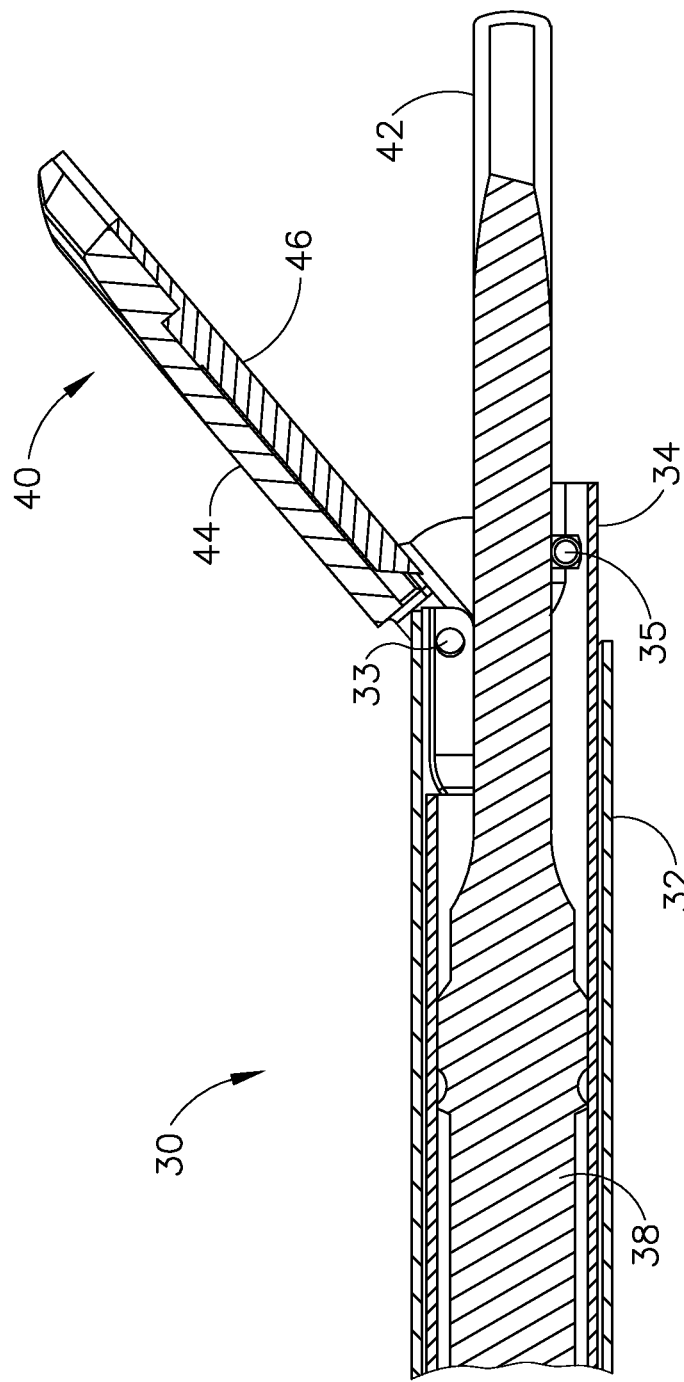
FIG. 3A depicts a side cross-sectional view of the end effector of FIG. 2, in the open configuration.
Figure 3B:
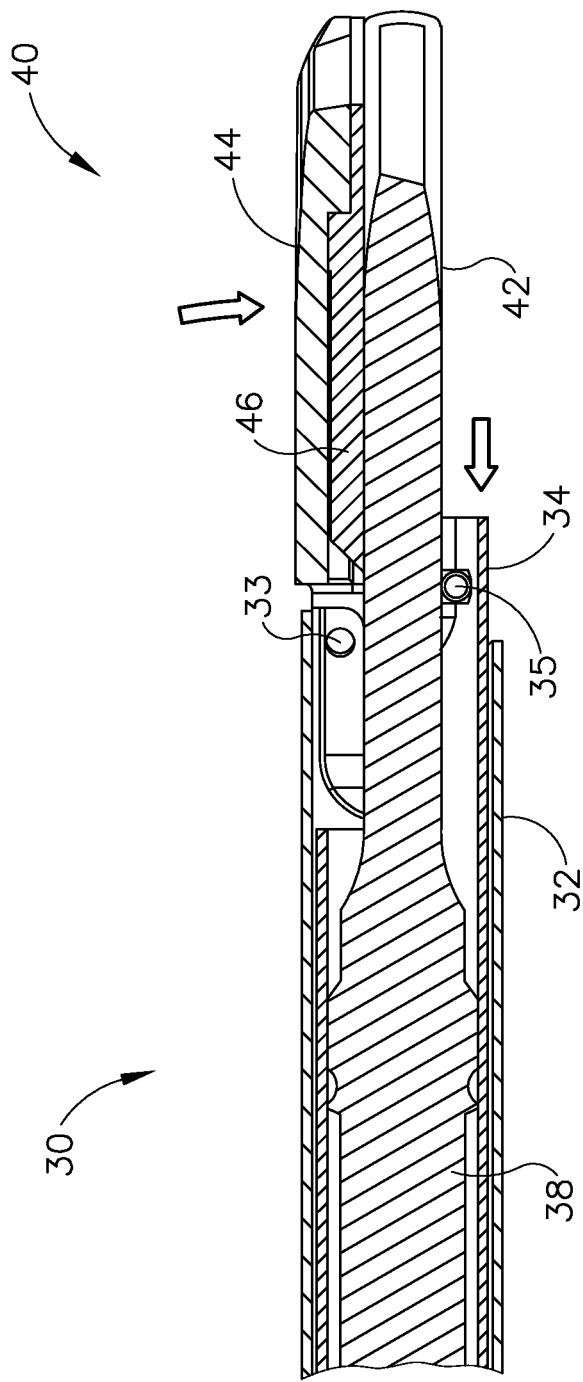
FIG. 3B depicts a side cross-sectional view of the end effector of FIG. 2, in a closed configuration.

As shown in FIGS. 2-3B, end effector (40) includes an ultrasonic blade (42) and a pivoting clamp arm (44). Clamp arm (44) includes a clamp pad (46) facing ultrasonic blade (42). Clamp arm (44) is pivotably coupled with a distal end of outer sheath (32) of shaft assembly (30), above ultrasonic blade (42), via a pin (33). A distal end of inner tube (34) is pivotably coupled with a proximal end of clamp arm (44), below ultrasonic blade (42), via another pin (35). Thus, longitudinal translation of inner tube (34) relative to outer sheath (32) causes clamp arm (44) to pivot about pin (33) toward and away from ultrasonic blade (42) to thereby clamp tissue between clamp pad (46) and ultrasonic blade (42) to transect and/or seal the tissue. In particular, as seen in the transition from FIG. 3A to FIG. 3B, proximal longitudinal translation of inner tube (34) relative to outer sheath (32) and handle assembly (20) causes clamp arm (44) to pivot toward ultrasonic blade (42); and distal longitudinal translation of inner tube (34) relative to outer sheath (32) and handle assembly (20) causes clamp arm (44) to pivot away from ultrasonic blade (42). It should therefore be understood that pivoting of trigger (28) toward pistol grip (24) will cause clamp arm (44) to pivot toward ultrasonic blade (42);

and that pivoting of trigger (28) away from pistol grip (24) will cause clamp arm (44) to pivot away from ultrasonic blade (42).

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (38), which extends through shaft assembly (30) to reach ultrasonic blade (42). Waveguide (38) is secured within shaft assembly (30) via a pin (not shown), which passes through waveguide (38) and shaft assembly (30). The pin is located at a position along the length of waveguide (38) corresponding to a node associated with resonant ultrasonic vibrations communicated through waveguide (38). As noted above, when ultrasonic blade (42) is in an activated state (i.e., vibrating ultrasonically), ultrasonic blade (42) is operable to effectively cut through and seal tissue, particularly when the tissue is being clamped between clamp pad (46) and ultrasonic blade (42). It should be understood that waveguide (38) may be configured to amplify mechanical vibrations transmitted through waveguide (38). Furthermore, waveguide (38) may include features operable to control the gain of the longitudinal vibrations along waveguide (38) and/or features to tune waveguide (38) to the resonant frequency of the system.

In the present example, the distal end of ultrasonic blade (42) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (42) and clamp pad (46), the ultrasonic oscillation of ultrasonic blade (42) may simultaneously sever the tissue and denature the proteins in adjacent tissue cells, thereby providing a coagulative effect with relatively little thermal spread. In some versions, generator (16) drives transducer assembly (12) dynamically, such that the ultrasonic vibrations at blade (42) vary. Such variation may be provided as a function of time, as a function of sensed conditions at the surgical site (e.g., tissue thickness, tissue impedance, etc.), and/or based on other factors or combinations of factors. By way of example only, generator (16) may adjust the amplitude and/or duty cycle associated with the ultrasonic vibrations based on sensed tissue impedance, in order to optimize performance. It should also be understood that, in some versions, an electrical current may also be provided through ultrasonic blade (42) and/or clamp pad (46) to also seal the tissue.

An operator may activate buttons (26) to selectively activate transducer assembly (12) to thereby activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, now U.S. Pat. No. 9,023,071, issued on May 5, 2015; U.S. Pub. No. 2011/0015660, now U.S. Pat. No. 8,461,744, issued on Jun. 11, 2013; U.S. Pub. No. 2012/0112687, now U.S. Pat. No. 9,381,058, issued on Jul. 5, 2016; U.S. Pub. No. 2012/0116265, now abandoned; U.S. patent application Ser. No. 13/538,588, now U.S. Pat. No. 9,393,037, issued on Jul. 19, 2016; and/or U.S. patent application Ser. No. 13/657,553, now U.S. Pat. No. 9,095,367, issued on Aug. 4, 2015. Additional merely illustrative variations for instrument (10) will be described in greater detail below. It should be understood that the below described variations may be readily applied to instrument (10) described above and any of the instruments referred to in any of the references that are cited herein, among others.

B. Exemplary Ultrasonic Surgical Instrument for Open Surgical Procedures

Figure 4:
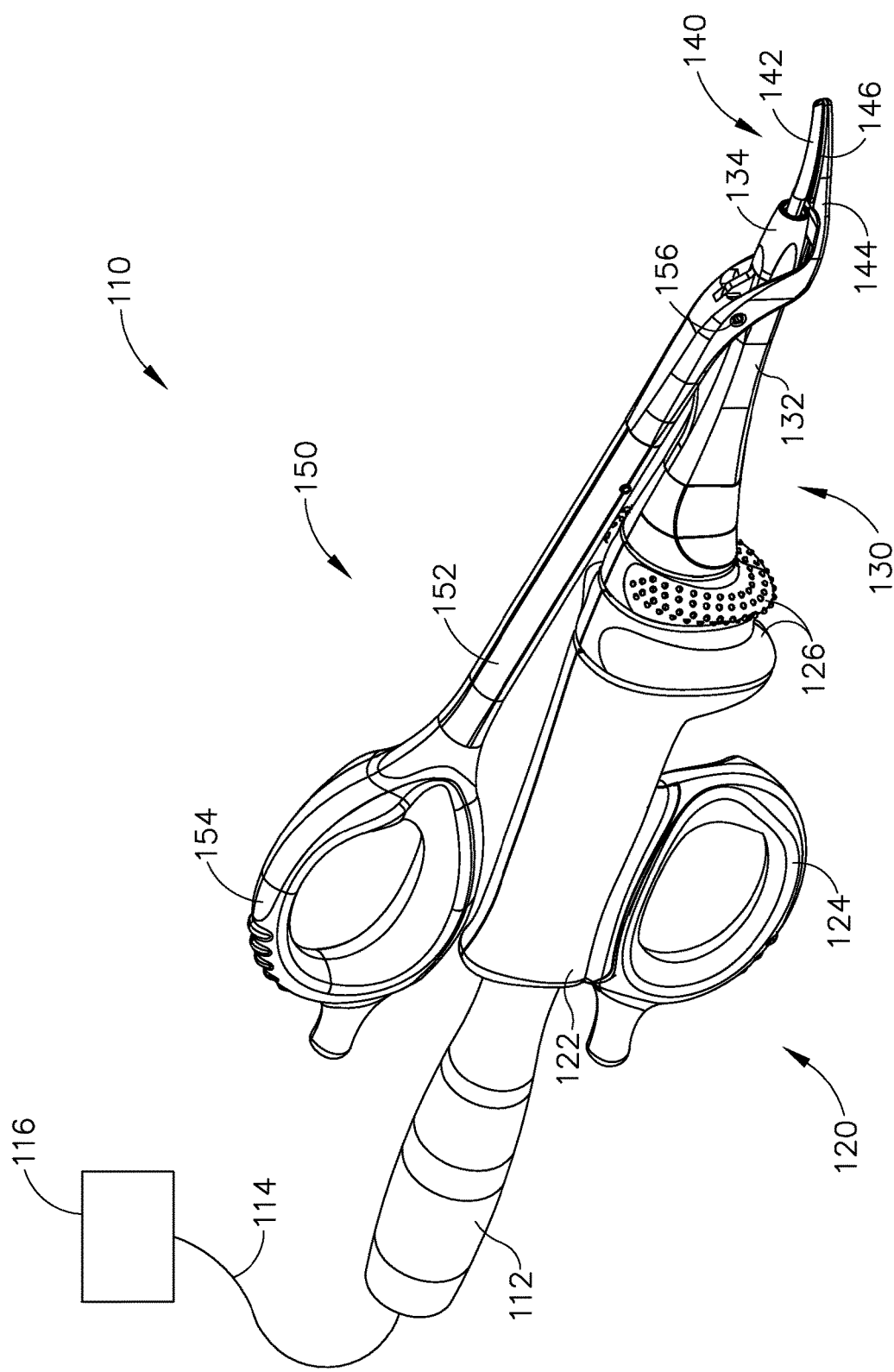
FIG. 4 depicts a perspective view of another exemplary surgical instrument.

FIG. 4 illustrates an exemplary ultrasonic surgical instrument (100) that is configured to be used in open surgical procedures. Instrument (100) of this example comprises a handle assembly (120), a shaft assembly (130), and an end effector (140). Handle assembly (120) comprises a body (122) including a finger grip ring (124) and a pair of buttons (126). Instrument (100) also includes a clamp arm assembly (150) that is pivotable toward and away from body (122). Clamp arm assembly (150) includes a shank (152) with a thumb grip ring (154). Thumb grip ring (154) and finger grip ring (124) together provide a scissor grip type of configuration. It should be understood, however, that various other suitable configurations may be used, including but not limited to a pistol grip configuration.

Figure 5:
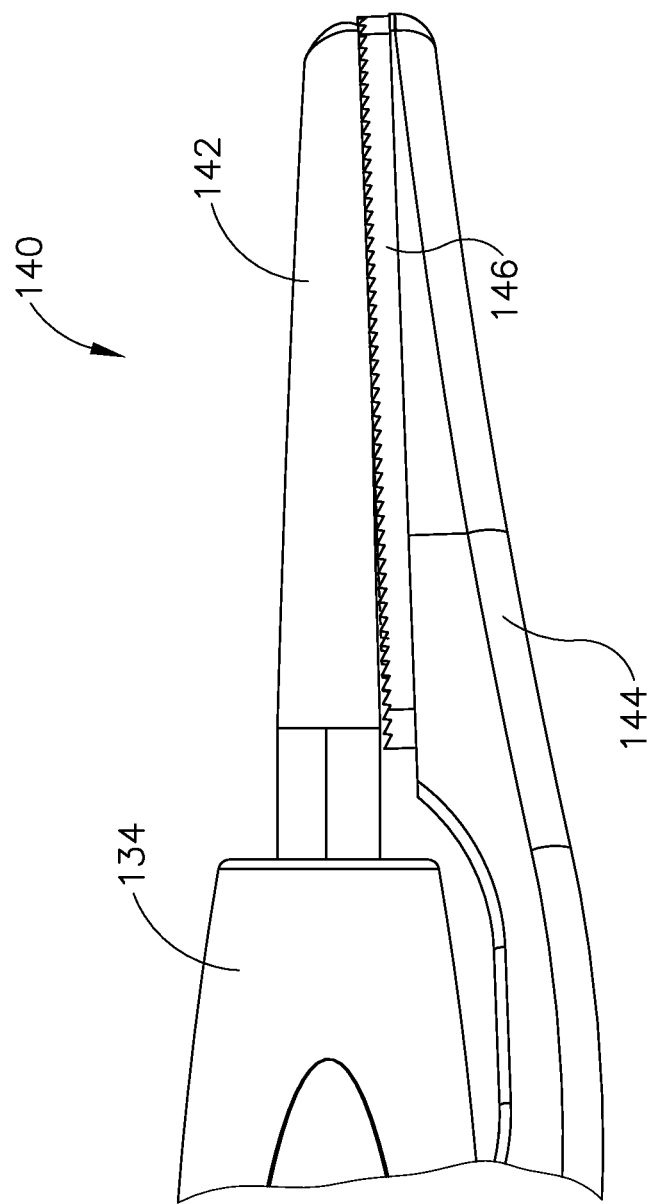
FIG. 5 depicts a side elevational view of the end effector of the instrument of FIG. 4, in a closed configuration.
Figure 6A:
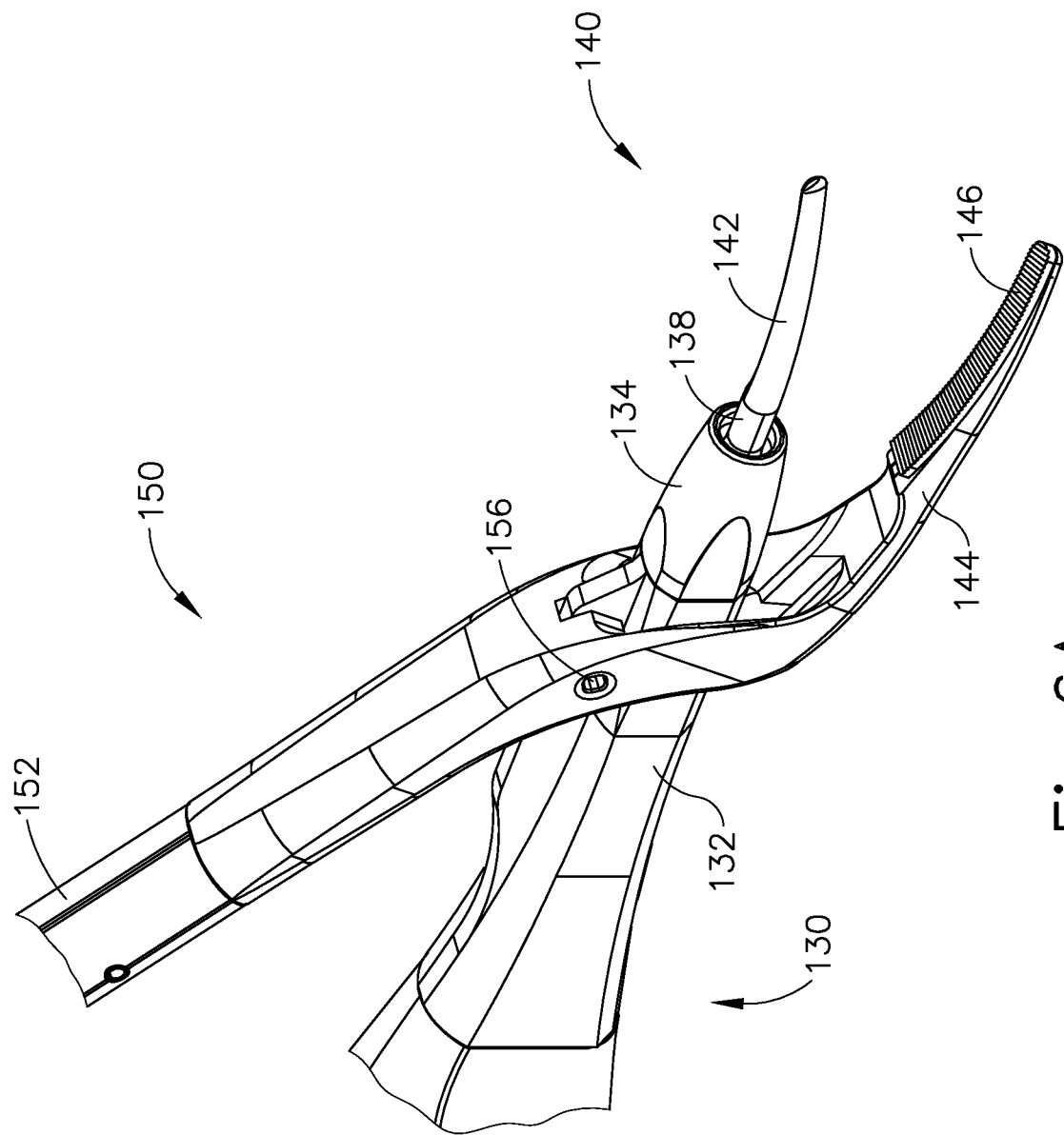
FIG. 6A depicts a perspective view of the end effector of FIG. 5, in an open configuration.
Figure 6B:
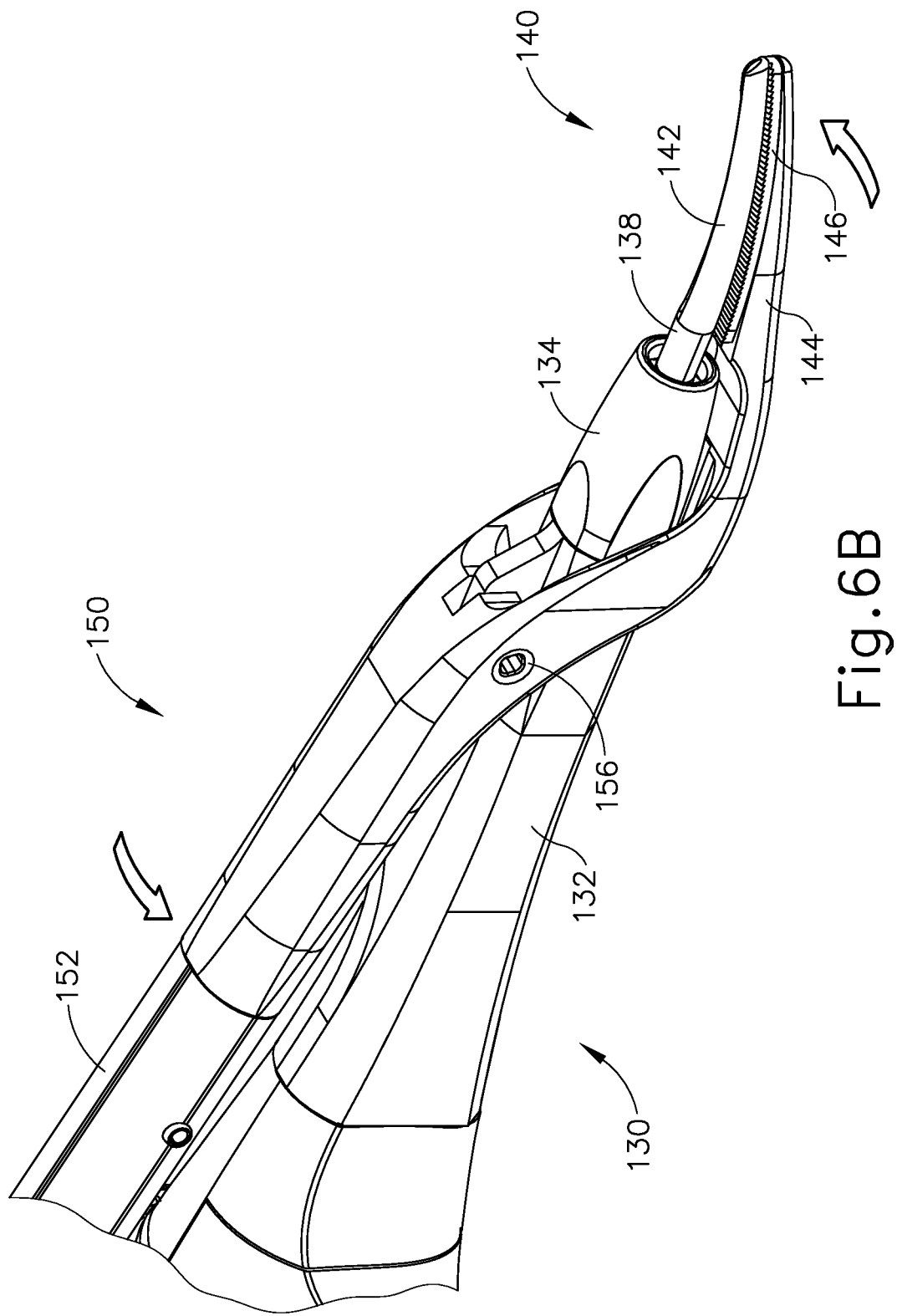
FIG. 6B depicts a perspective view of the end effector of FIG. 5, in a closed configuration.

Shaft assembly (130) comprises an outer sheath (132) extending distally from body (122). A cap (134) is secured to the distal end of sheath (132). As best seen in FIGS. 5-6B, end effector (140) comprises an ultrasonic blade (142) and a clamp arm (144). Ultrasonic blade (142) extends distally from cap (134). Clamp arm (144) is an integral feature of clamp arm assembly (150). Clamp arm (144) includes a clamp pad (146) facing ultrasonic blade (142). Clamp arm assembly (150) is pivotally coupled with outer sheath (132) via a pin (156). Clamp arm (144) is positioned distal to pin (156); while shank (152) and thumb grip ring (154) are positioned proximal to pin (156). Thus, as shown in FIGS. 6A-6B, clamp arm (144) is pivotable toward and away from ultrasonic blade (142) based on pivoting of thumb grip ring (154) toward and away from body (122) of handle assembly (120). It should therefore be understood that an operator may squeeze thumb grip ring (154) toward body (122) to thereby clamp tissue between clamp pad (146) and ultrasonic blade (142) to transect and/or seal the tissue. In some versions, one or more resilient members are used to bias clamp arm (144) to the open position shown in FIG. 6A. By way of example only, such a resilient member may comprise a leaf spring, a torsion spring, and/or any other suitable kind of resilient member.

Referring back to FIG. 4, an ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Ultrasonic vibrations that are generated by transducer assembly (112) are communicated along an acoustic waveguide (138), which extends through shaft assembly (130) to reach ultrasonic blade (142). Waveguide (138) is secured within shaft assembly (130) via a pin (not shown), which passes through waveguide (138) and shaft assembly (130). This pin is located at a position along the length of waveguide (138) corresponding to a node associated with resonant ultrasonic vibrations communicated through waveguide (138). As noted above, when ultrasonic blade (142) is in an activated state (i.e., vibrating ultrasonically), ultrasonic blade (142) is operable to effectively cut through and seal tissue, particularly when the tissue is being clamped between clamp pad (146) and ultrasonic blade (142). It should be understood that waveguide (138) may be configured to amplify mechanical vibrations transmitted through waveguide (138). Furthermore, waveguide (138) may include features operable to control the gain of the longitudinal vibrations along waveguide (138) and/or features to tune waveguide (138) to the resonant frequency of the system.

In the present example, the distal end of ultrasonic blade (142) is located at a position corresponding to an anti-node associated with resonant ultrasonic vibrations communicated through waveguide (138), in order to tune the acoustic assembly to a preferred resonant frequency $f_o$ when the acoustic assembly is not loaded by tissue. When transducer assembly (112) is energized, the distal end of ultrasonic blade (142) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (142) and clamp pad (46), the ultrasonic oscillation of ultrasonic blade (142) may simultaneously sever the tissue and denature the proteins in adjacent tissue cells, thereby providing a coagulative effect with relatively little thermal spread. In some versions, an electrical current may also be provided through ultrasonic blade (142) and/or clamp pad (146) to also seal the tissue.

An operator may activate buttons (126) to selectively activate transducer assembly (112) to thereby activate ultrasonic blade (142). In the present example, two buttons (126) are provided—one for activating ultrasonic blade (142) at a low power and another for activating ultrasonic blade (142) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb in thumb grip ring (154), position their ring finger in finger grip ring (124), position their middle finger about body (122), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874, now abandoned; U.S. Pub. No. 2007/0191713, now abandoned;

U.S. Pub. No. 2007/0282333, now abandoned; U.S. Pub. No. 2008/0200940, now abandoned; U.S. Pub. No. 2010/0069940, now U.S. Pat. No. 9,023,071, issued on May 5, 2015; U.S. Pub. No. 2011/0015660, now U.S. Pat. No. 8,461,744, issued on Jun. 11, 2013; U.S. Pub. No. 2012/0112687, now U.S. Pat. No. 9,381,058, issued on Jul. 5, 2016; U.S. Pub. No. 2012/0116265, now abandoned; U.S. patent application Ser. No. 13/538,588, now U.S. Pat. No. 9,393,037, issued on Jul. 19, 2016; U.S. patent application Ser. No. 13/657,553, now U.S. Pat. No. 9,095,367, issued on Aug. 4, 2015; and/or U.S. patent application Ser. No. 14/031,665, published as U.S. Pub. No. 2015/0080925 on Mar. 19, 2015, now abandoned. Additional merely illustrative variations for instrument (100) will be described in greater detail below. It should be understood that the below described variations may be readily applied to instrument (100) described above and any of the instruments referred to in any of the references that are cited herein, among others.

II. Exemplary Ultrasonic Surgical Instruments with Ultrasonic Blade Rotation Mechanisms Clamp arms (44, 144) of instruments (10, 100) discussed above move pivotally toward and away from ultrasonic blades (42, 142), along a single plane. In some instances, this pivotal movement of clamp arm (44, 144) may not allow for an adequate distribution of force to be applied to the tissue clamped between clamp arm (44, 144) and ultrasonic blade (42, 142). This inadequate distribution of force may allow for "tags" of tissue (e.g., flattened but uncut regions of tissue) to be formed, particularly at a distal end and/or proximal end of end effector (40, 140). Thus, in some versions of instrument (10, 100) it may be desirable to provide a mechanism that provides improved distribution of force to be applied to the tissue clamped between clamp arm (44, 144) and ultrasonic blade (42, 142) to reduce the occurrence of tissue tags and/or to provide severing of tissue tags. For instance, one mechanism may selectively rotate ultrasonic blade (42, 142) about a longitudinal axis (e.g., the longitudinal axis of waveguide (38, 138)) as clamp arm (44, 144) moves toward and/or away from ultrasonic blade (42, 142) to take advantage of a curved profile of ultrasonic blade (42, 142), to thereby apply an adequate distribution of force to the tissue clamped between clamp arm (44, 144) and ultrasonic blade (42, 142) through a rolling contact effect.

In versions where ultrasonic blade (42, 142) has a curved configuration, this rolling contact may provide a contact interface between ultrasonic blade (42, 142) and clamp pad (46, 146) that is localized along a portion of the length of blade (42, 142), with that localized contact interface area traveling along the length of ultrasonic blade (42, 142) (e.g., from the distal end of ultrasonic blade (42, 142) to the proximal end of ultrasonic blade (42, 142) or from the proximal end of ultrasonic blade (42, 142) to the distal end of ultrasonic blade (42, 142), etc.) as ultrasonic blade (42, 142) rotates relative to clamp pad (46, 146). This rolling contact may ensure that pressure is applied to tissue along the entire length of tissue captured between ultrasonic blade (42, 142) and clamp pad (46, 146). This rolling contact may also reduce wear on clamp pad (46, 146) and thus increase its useful life. It should be understood that the rolling contact described herein may occur directly between ultrasonic blade (42, 142) and clamp pad (46, 146) (e.g., in regions where no tissue is captured between ultrasonic blade (42, 142) and clamp pad (146)) or indirectly between ultrasonic blade (42, 142) and clamp pad (46, 146) (e.g., in regions where tissue is captured between ultrasonic blade (42, 142) and clamp pad (46, 146)).

In addition to or as an alternative to preventing or otherwise addressing tissue tags, the examples described herein may also provide varying pressure profiles on tissue clamped between ultrasonic blade (42, 142) and clamp pad (46, 146). For instance, when end effector (40, 140) is used to apply a rolling contact pressure on a vessel that is approximately 7 mm in thickness, ultrasonic blade (42, 142) and clamp pad (46, 146) may initially provide a low pressure to seal the tissue; followed by a high pressure to cut the tissue. As yet another merely illustrative example, rolling contact applied through ultrasonic blade (42, 142) and clamp pad (46, 146) may squeeze and roll a vessel to better direct apposition of the collagen rich adventia layers of the tissue of the vessel.

Various illustrative examples of an instrument that includes an ultrasonic blade (42, 142) rotation mechanism will be described in greater detail below, while other examples will be apparent to those of ordinary skill in the art in view of the teachings herein. It should be understood that the below examples may be viewed as variations of instruments (10, 100), such that various teachings below may be readily combined with various teachings above as will be apparent to those of ordinary skill in the art. It should also be understood that ultrasonic blade (42, 142) may be activated ultrasonically while ultrasonic blade (42, 142) is being rotated about the longitudinal axis.

A. First Exemplary Ultrasonic Blade Rotation Mechanism

Figure 7A:
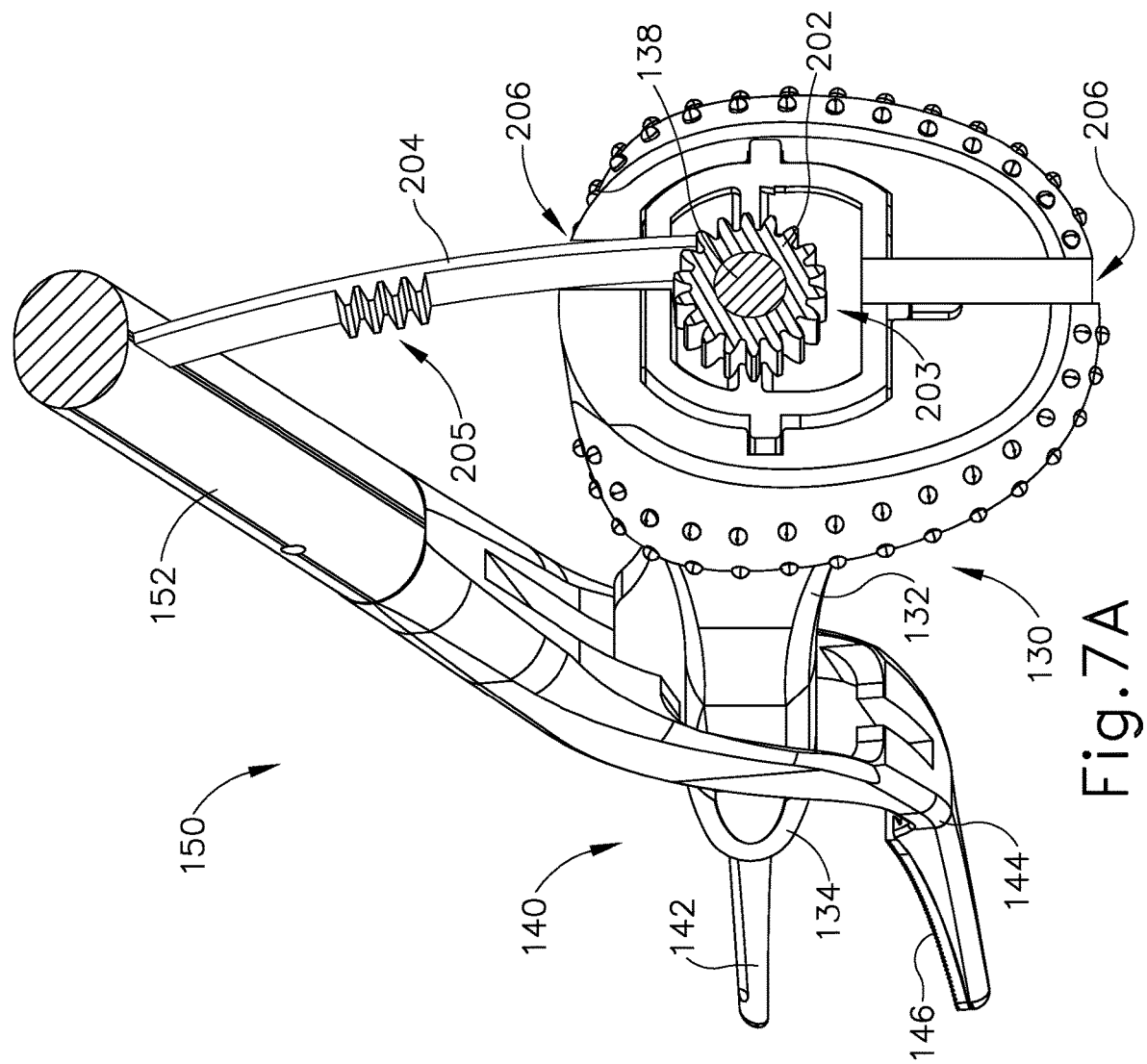
FIG. 7A depicts a cross-sectional view of a variation of the instrument of FIG. 4 having an exemplary ultrasonic blade rotation mechanism in a first configuration.
Figure 7B:
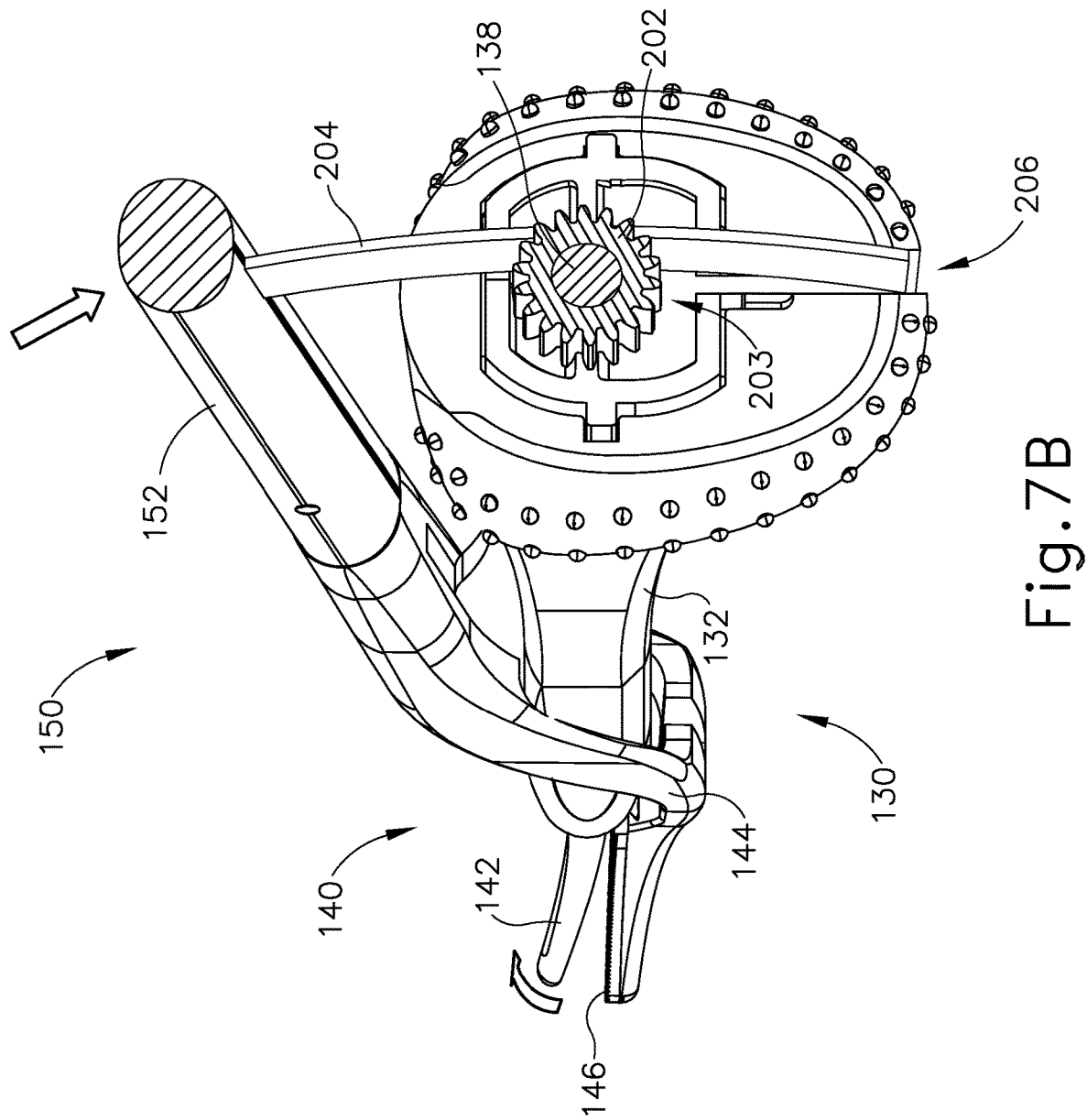
FIG. 7B depicts a cross-sectional view of the instrument of FIG. with the ultrasonic blade rotation mechanism in a second configuration.

FIGS. 7A and 7B show an exemplary ultrasonic blade rotation mechanism (200), which may be readily incorporated into instrument (100). Rotation mechanism (200) of the present example comprises a pinion gear (202) and a rack member (204). Gear (202) is secured to exterior surface of waveguide (138), such that gear (202) and waveguide (138) rotate concomitantly. In the present example, gear (202) is secured to waveguide (138) at a node associated with resonant ultrasonic vibrations communicated through waveguide (138) and ultrasonic blade (142). Alternatively, gear (202) may be secured to waveguide (138) away from a node associated with resonant ultrasonic vibrations communicated through waveguide (138) and ultrasonic blade (142). Waveguide (138) of the present example is rotatably disposed within shaft assembly (130) such that waveguide (138) is rotatable relative to shaft assembly (130). Gear (202) comprises a plurality of teeth (203) arranged in an angular pattern and extending radially and longitudinally from an exterior surface of gear (202).

Rack member (204) extends downwardly from a bottom surface of shank (152) of clamp arm assembly (150) and passes through a passageway (206) that passes through shaft assembly (130). Passageway (206) passes through shaft assembly (130) at a position adjacent to teeth (203) of gear (202). A portion of rack member (204) near shank (152) comprises a plurality of teeth (205). As will be understood from the discussion below, teeth (205) of rack member (204) are configured to engage teeth (203) of gear (202) to thereby cause rotation of gear (202).

As shown in FIG. 7A, with clamp arm assembly (150) in an open position, teeth (205) of rack member (204) are not engaged with teeth (203) of gear (202). Thus, that as clamp arm assembly (150) is moved through a first range of motion toward a closed position, movement of rack member (204) through passageway (206) will not cause rotation of gear (202). However, teeth (205) eventually engage teeth (203) as clamp arm assembly (150) continues to pivot toward the closed position. In particular, teeth (205) of rack member (204) mesh with teeth (203) of gear (202) as clamp arm assembly (150) continues to pivot through a second range of motion toward the closed position as shown in FIG. 7B. This engagement of teeth (203) with teeth (205) causes rotation of gear (202), waveguide (138), and ultrasonic blade (142) as clamp arm assembly (150) pivots through the second range of motion.

As can be seen in the transition from FIG. 7A to FIG. 7B, the rotation of ultrasonic blade (142) provides a rolling engagement between ultrasonic blade (142) and clamp pad (146) as clamp arm assembly (150) pivots through the second range of motion, due to the curved configuration of ultrasonic blade (142). In some versions, only the distal end of ultrasonic blade (142) contacts clamp pad (146) at the beginning of the second range of motion; then the area of localized contact between ultrasonic blade (142) and clamp pad (146) translates proximally along the length of blade (142) as clamp arm assembly (150) travels through the remainder of the second range of motion. As yet another merely illustrative example, the full length of ultrasonic blade (142) may initially contact clamp pad (146) at the beginning of the second range of motion; then an area of localized contact between ultrasonic blade (142) and clamp pad (146) translates proximally from the distal end of blade (142) to the proximal end of blade (142) (or distally from the proximal end of blade (142) to the distal end of blade (142)) as clamp arm assembly (150) travels through the remainder of the second range of motion. In any of the foregoing examples, the rolling engagement between a localized region of the length of ultrasonic blade (142) and clamp pad (146) may either prevent tissue tags from being formed or may sever tissue tags, promoting a clean, full cut by end effector (140).

In the present example, the location of teeth (205) proximal to shank (152) causes waveguide (138) to only rotate as clamp arm assembly (150) reaches a substantially closed position, such that ultrasonic blade (142) will only rotate after tissue has been clamped between clamp arm (144) and ultrasonic blade (142). Alternatively, teeth (205) may be located anywhere along rack member (204) to thereby cause rotation of waveguide (138) and ultrasonic blade (142) at any point between the open position and the closed position of clamp arm assembly (150). It should further be appreciated that, as clamp arm assembly (150) is moved from the closed position back toward the open position, teeth (205) of rack member (204) engages teeth (203) of gear (202) to thereby rotate waveguide (202) and ultrasonic blade (142) back toward their original orientation.

Although rotation mechanism (200) is discussed as being used with instrument (100) in the present example, it should be understood that rotation mechanism (200) may be readily incorporated into instrument (10). For instance, rack member (204) may be secured to trigger (28) and configured to cause rotation of waveguide (38) as trigger (28) is moved toward and away from pistol grip (24). Other suitable variations of rotation mechanism (200) will be apparent to those of ordinary skill in the art in view of the teachings herein.

B. Second Exemplary Ultrasonic Blade Rotation Mechanism

Figure 8:
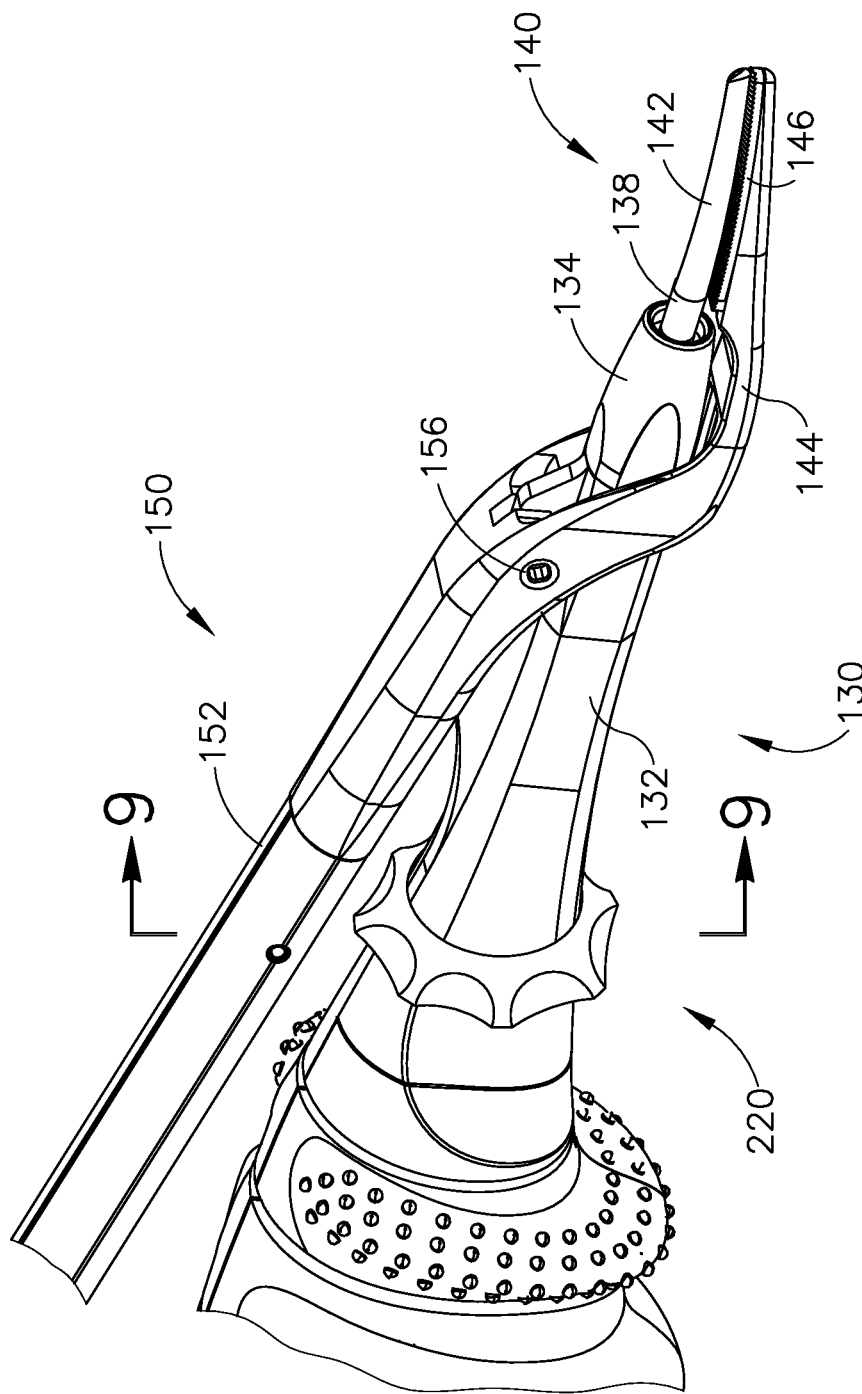
FIG. 8 depicts a perspective view of another variation of the instrument of FIG. 4 having an exemplary alternative ultrasonic blade rotation mechanism.
Figure 9:
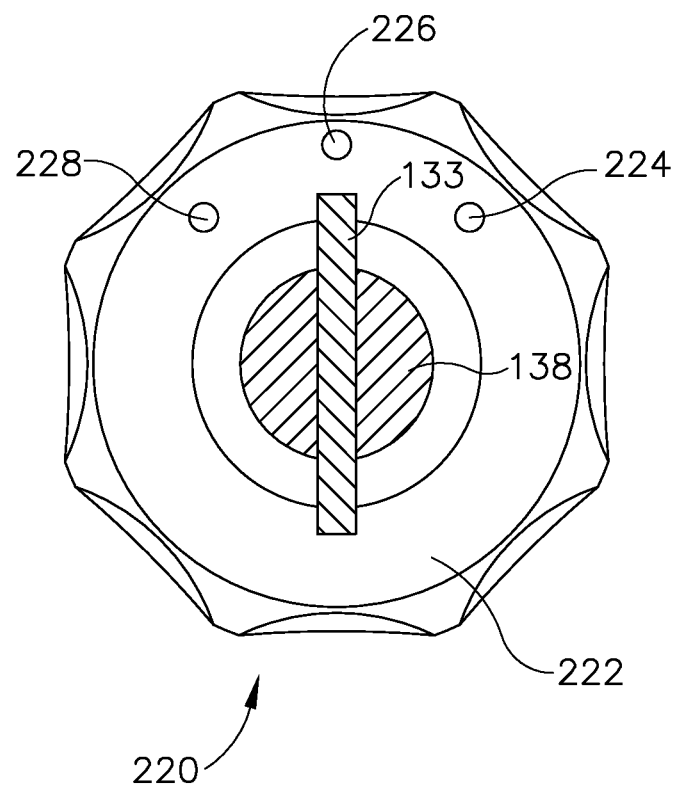
FIG. 9 depicts a cross-sectional view of the instrument of FIG. 8, taken along line 9-9 of FIG. 8.

FIGS. 8 and 9 show an exemplary alternative ultrasonic blade rotation mechanism (220) that may be readily incorporated into instrument (100). Rotation mechanism (220) of this example comprises a rotation knob (222). Waveguide (138) of the present example is rotatably disposed within shaft assembly (130) such that waveguide (138) is rotatable relative to shaft assembly (130). Rotation knob (222) is secured to waveguide (138) via pin (133) such that rotation of rotation knob (222) causes concurrent rotation of waveguide (138). It should therefore be understood that before, while, and/or after clamp arm assembly (150) is moved toward the closed position, a user may manually rotate waveguide (138) and ultrasonic blade (142) via rotation knob (222).

As shown in FIG. 9, a proximal surface of rotation knob (222) comprises a series of detent recesses (224, 226, 228). Detent recesses (224, 226, 228) are configured to align with a projection (not shown) of shaft assembly (130) to thereby selectively lock rotation knob (222), waveguide (138), and ultrasonic blade (142) in a particular rotational position. The projection may be resiliently biased or otherwise deformable. In addition to providing selective locking of the angular position of rotation knob (222), waveguide (138), and ultrasonic blade (142) in a particular rotational position relative to shaft assembly (130), detent recesses (224, 226, 228) and the projection may also provide audible and/or tactile feedback to the operator indicating that a particular angular orientation has been reached. For instance, the operator may hear and/or feel the projection pop into a recess (224, 226, 228).

Detent recess (226) of rotation knob (222) represents a rotational position wherein ultrasonic blade (142) is oriented substantially parallel to clamp pad (146). Detent recess (224) of rotation knob (222) represents a rotational position wherein ultrasonic blade (138) has been rotated counterclockwise approximately 45° such that a distal tip of ultrasonic blade (142) is angled toward clamp pad (146), with the proximal portion of ultrasonic blade (142) being angled away from clamp pad (146). In other words, detent recess (224) is associated with a tip-loaded configuration for end effector (140). Such a tip-loaded configuration may be used to prevent tissue tags that might otherwise be left by end effector (140) if end effector (140) were actuated with ultrasonic blade (142) oriented substantially parallel to clamp pad (146). In addition or in the alternative, such a tip-loaded configuration may promote the use of the distal end of end effector (140) to make smaller "nibble" types of incisions in tissue.

Detent recess (228) of rotation knob (222) represents a rotational position wherein ultrasonic blade (138) has been rotated clockwise approximately 45° such that a distal tip of ultrasonic blade (142) is angled away from clamp pad (146), with the proximal portion of ultrasonic blade (142) being angled toward clamp pad (146). In other words, detent recess (228) is associated with a proximal-loaded configuration for end effector (140). Such a proximal-loaded configuration may be used to prevent tissue tags that might otherwise be left by end effector (140) if end effector (140) were actuated with ultrasonic blade (142) oriented substantially parallel to clamp pad (146). In some instances, the operator rotates knob (222) to select which detent recess (224, 226, 228) to engage, and then actuates end effector (140) to compress, cut, and coagulate tissue clamped between clamp pad (146) and ultrasonic blade (142) at the corresponding angular orientation relative to shaft assembly (130). In some other versions, the operator rotates knob (222) to cycle through or between two or more detent recess (224, 226, 228) while tissue is clamped in end effector (140), such as to provide a rolling engagement between ultrasonic blade (142) and clamp pad (146) as described above. Other suitable ways in which rotation mechanism (200) may be operated will be apparent to those of ordinary skill in the art in view of the teachings herein.

While detent recesses (224, 226, 228) of the present example are angularly arranged approximately 45° from one another, it should be understood that detents (224, 226, 228) may be arranged at any other suitable angular distance. Moreover, any other suitable number of detents may be provided. While rotation mechanism (220) is discussed as being used with instrument (100) in the present example, it should be understood that rotation mechanism (220) may readily incorporated into instrument (10).

C. Third Exemplary Ultrasonic Blade Rotation Mechanism

Figure 10:
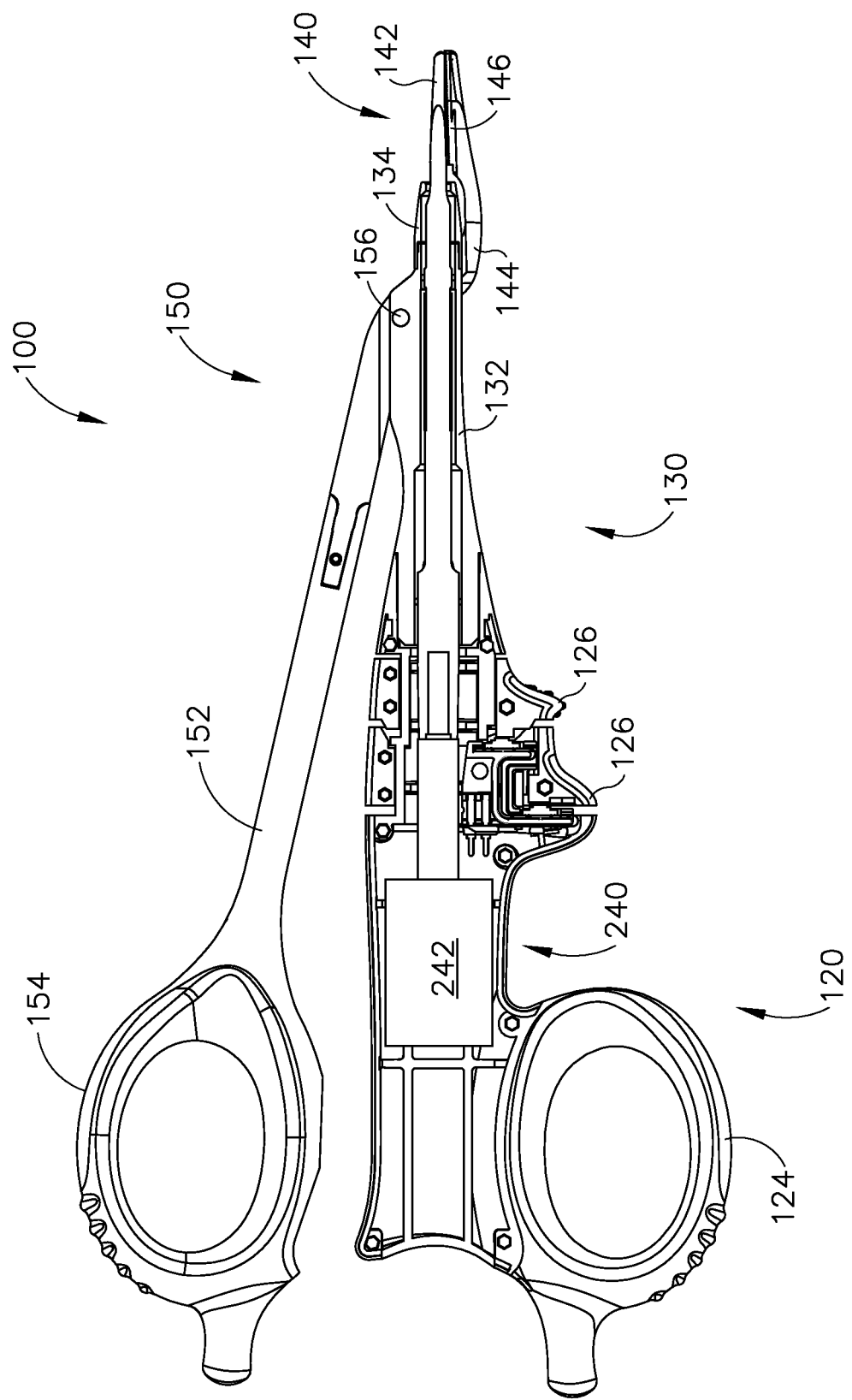
FIG. 10 depicts a side elevational view of another variation of the instrument of FIG. 4 having another exemplary alternative ultrasonic blade rotation mechanism.
Figure 11A:
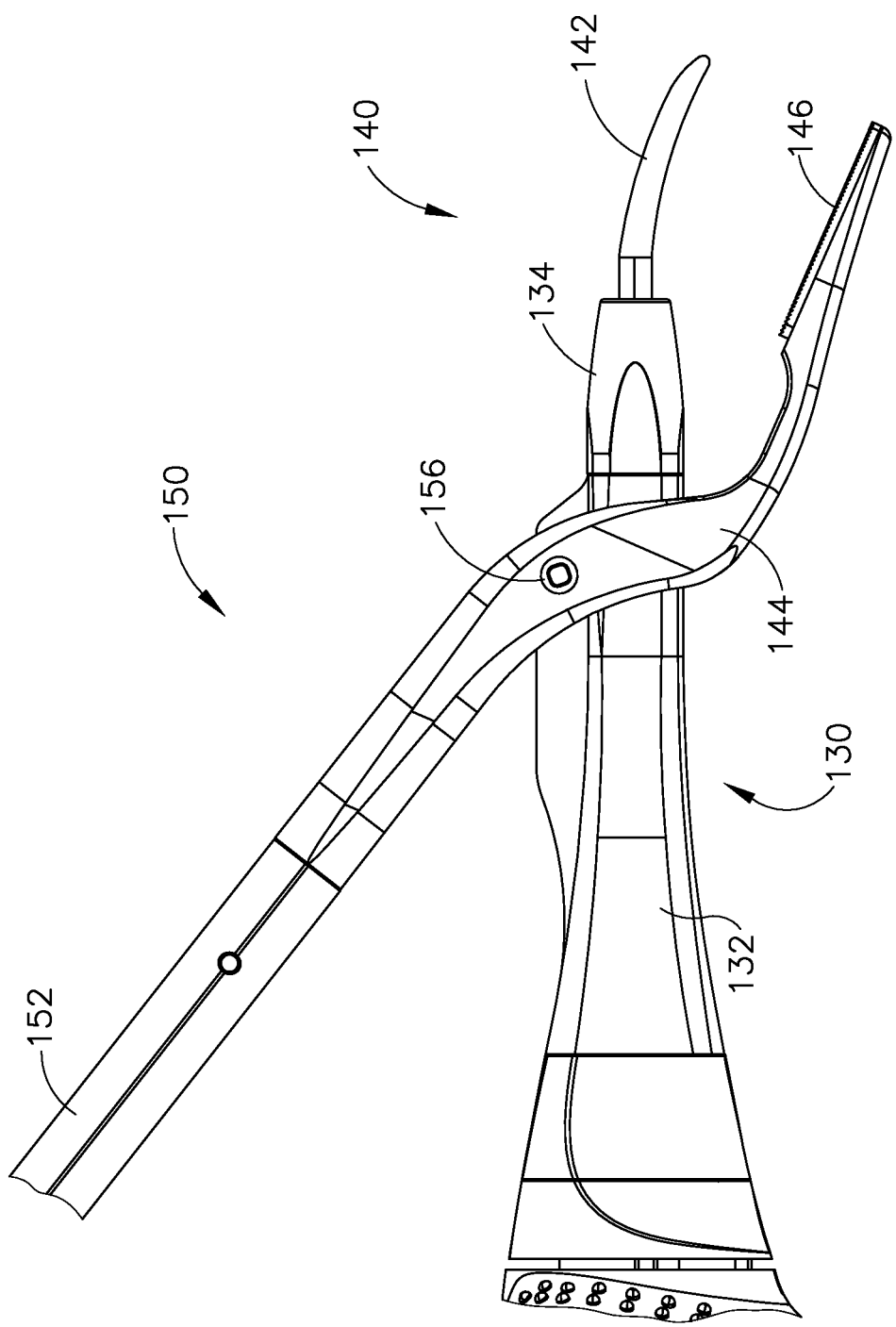
FIG. 11A depicts a side elevational view of the instrument of FIG. 10, with the instrument in an open configuration and with an ultrasonic blade in a first rotational position.
Figure 11B:
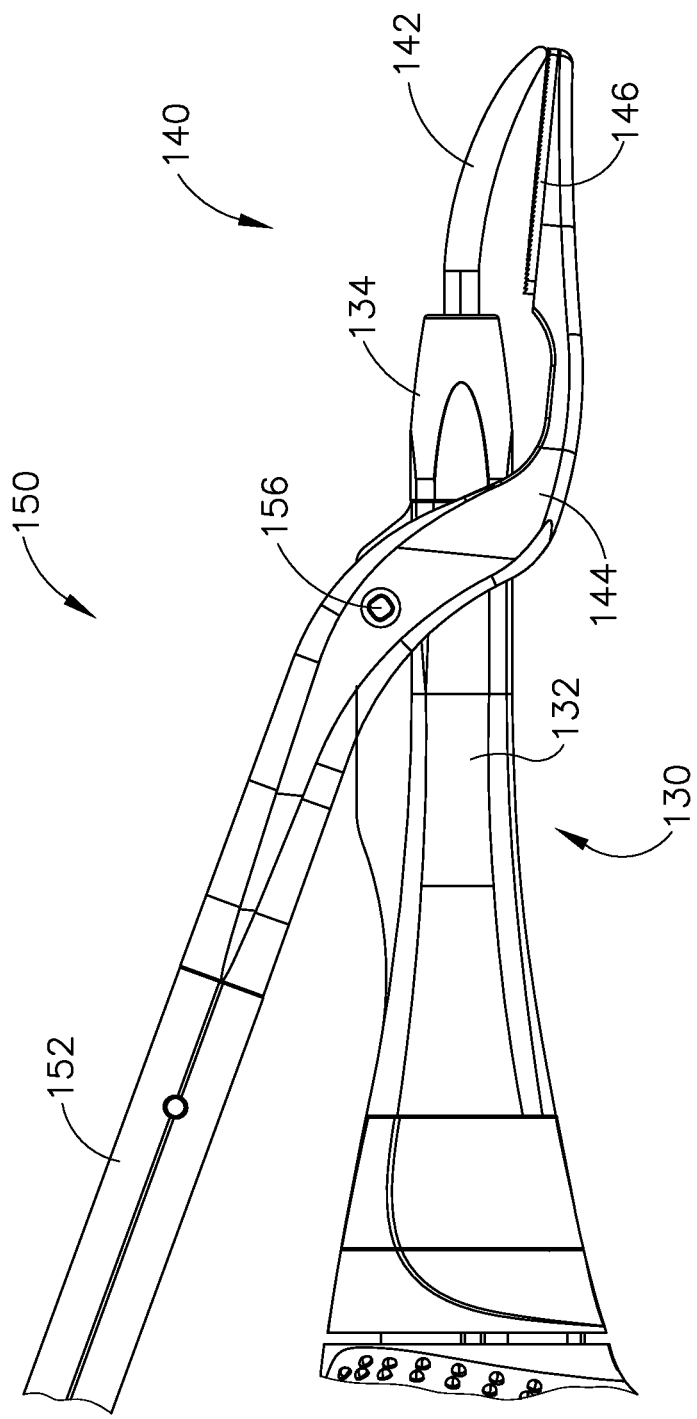
FIG. 11B depicts a side elevational view of the instrument of FIG. 10, with the instrument in a first closed configuration and with the ultrasonic blade in the first rotational position.
Figure 11C:
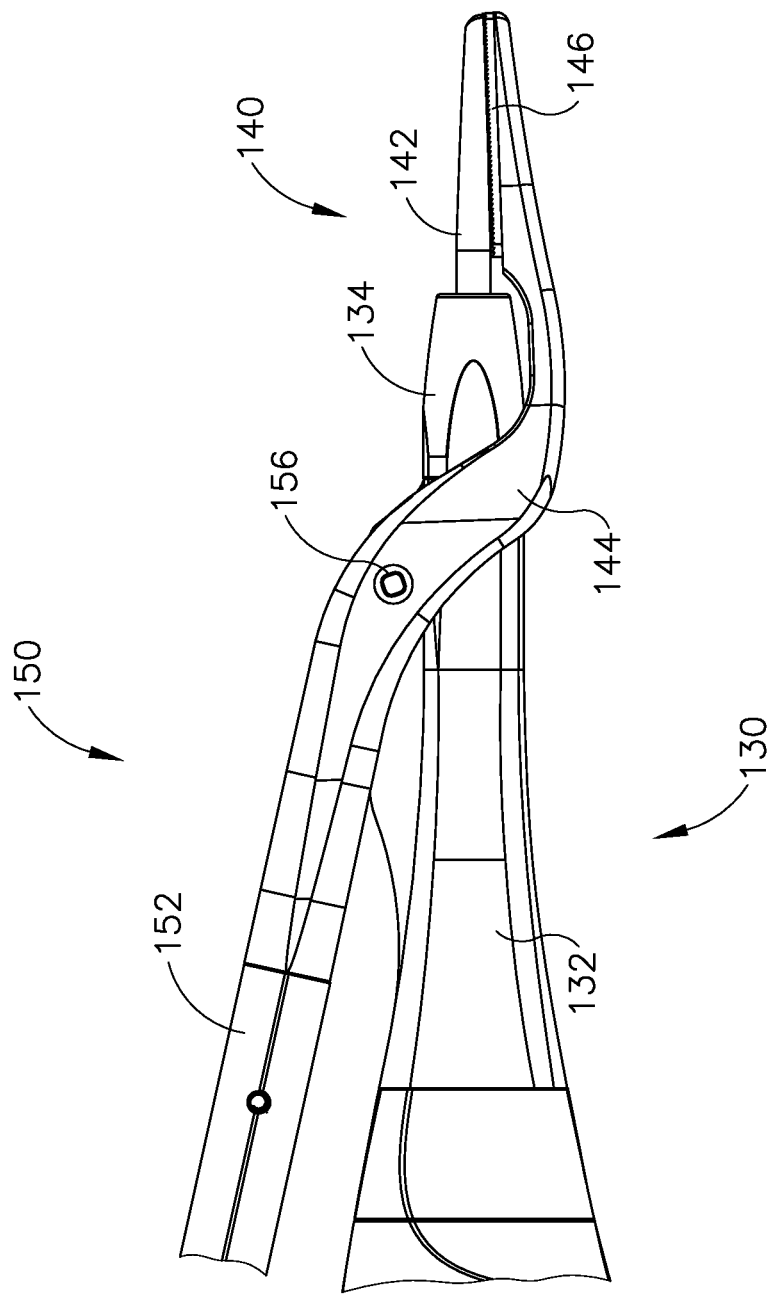
FIG. 11C depicts a side elevational view of the instrument of FIG. 10, with the instrument in a second closed configuration and with the ultrasonic blade rotated into a second rotational position.
Figure 11D:
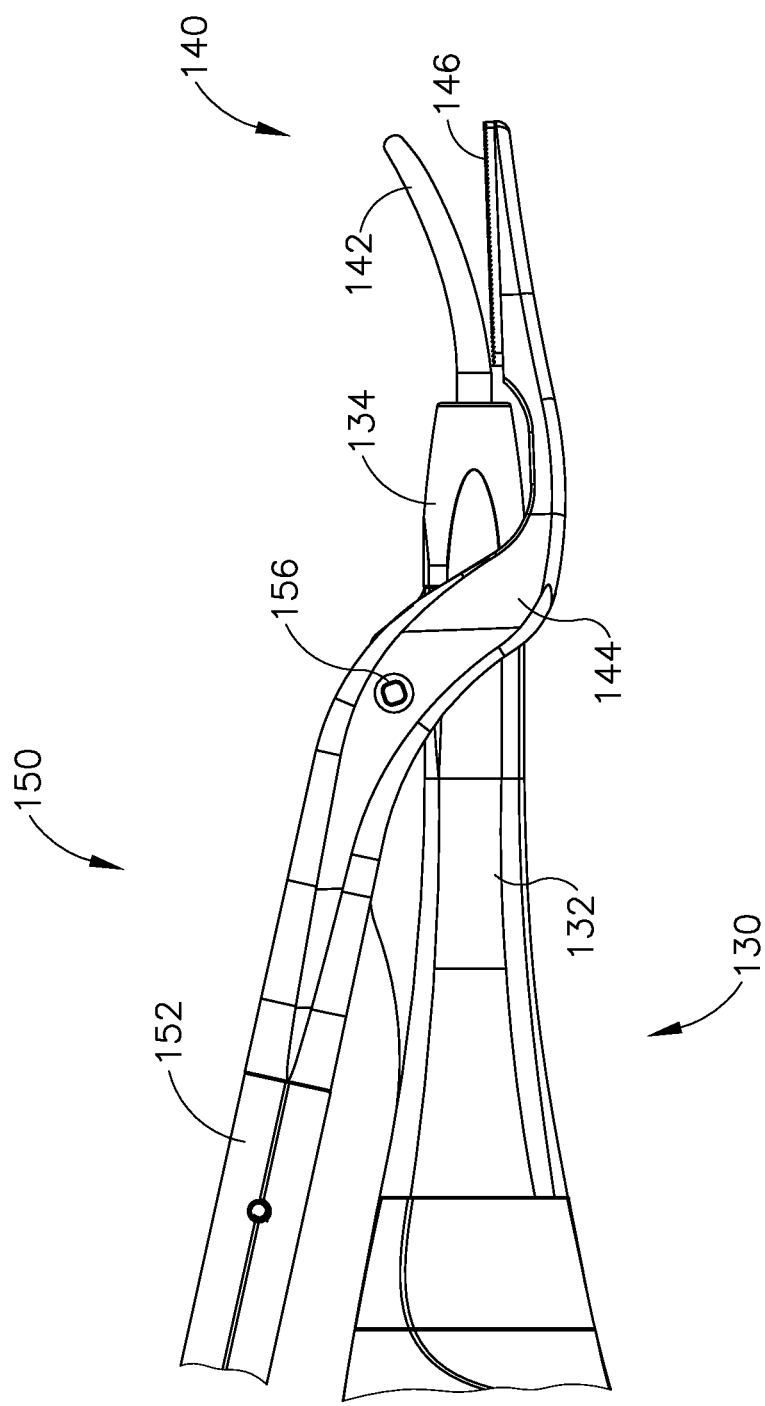
FIG. 11D depicts a side elevational view of the instrument of FIG. 10, with the instrument in the second closed configuration with the ultrasonic blade rotated into a third rotational position.
Figure 12A:
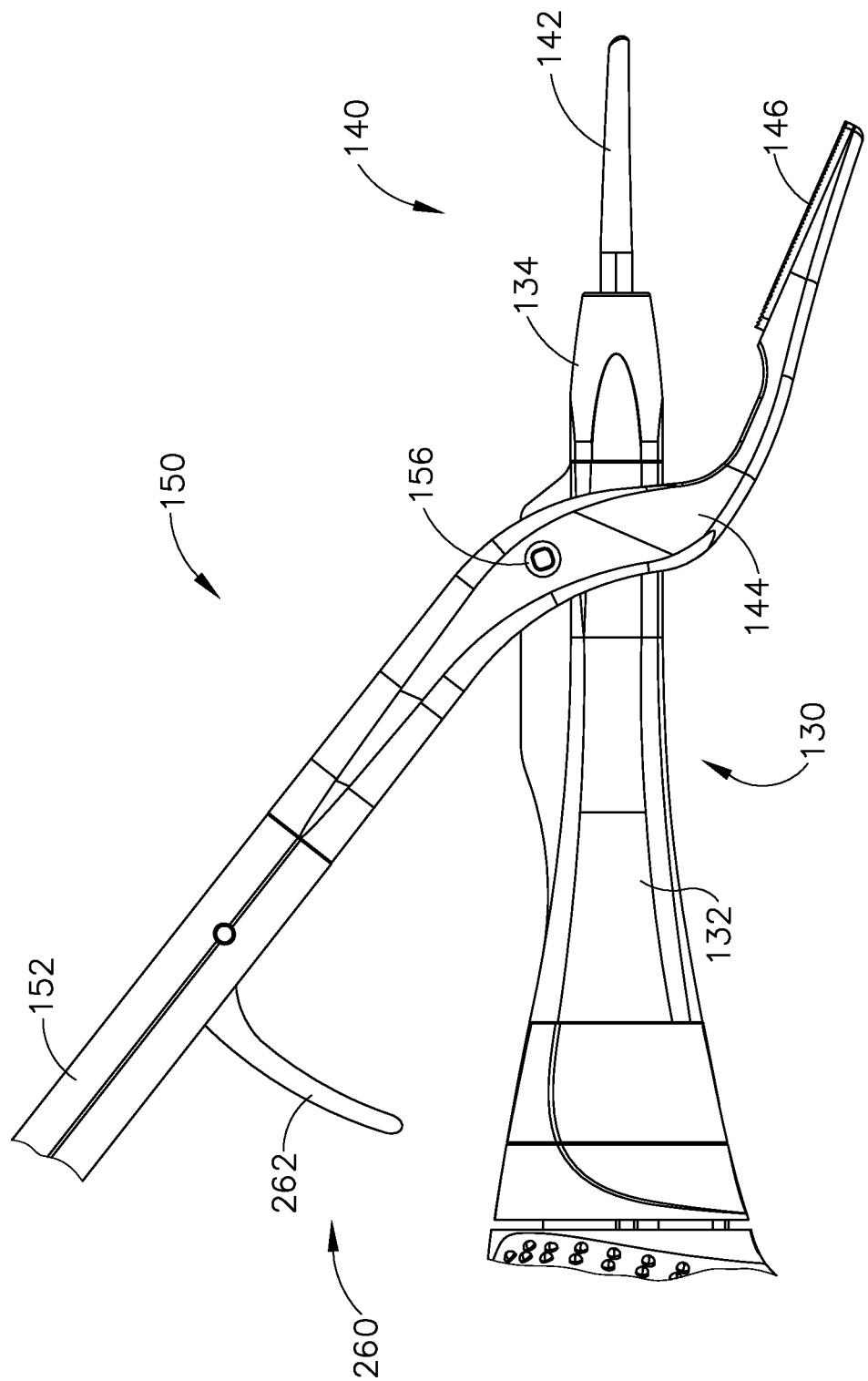
FIG. 12A depicts a side elevational view of another variation of the instrument of FIG. 4 having yet another exemplary alternative ultrasonic blade rotation mechanism, with the instrument in an open configuration.
Figure 12B:
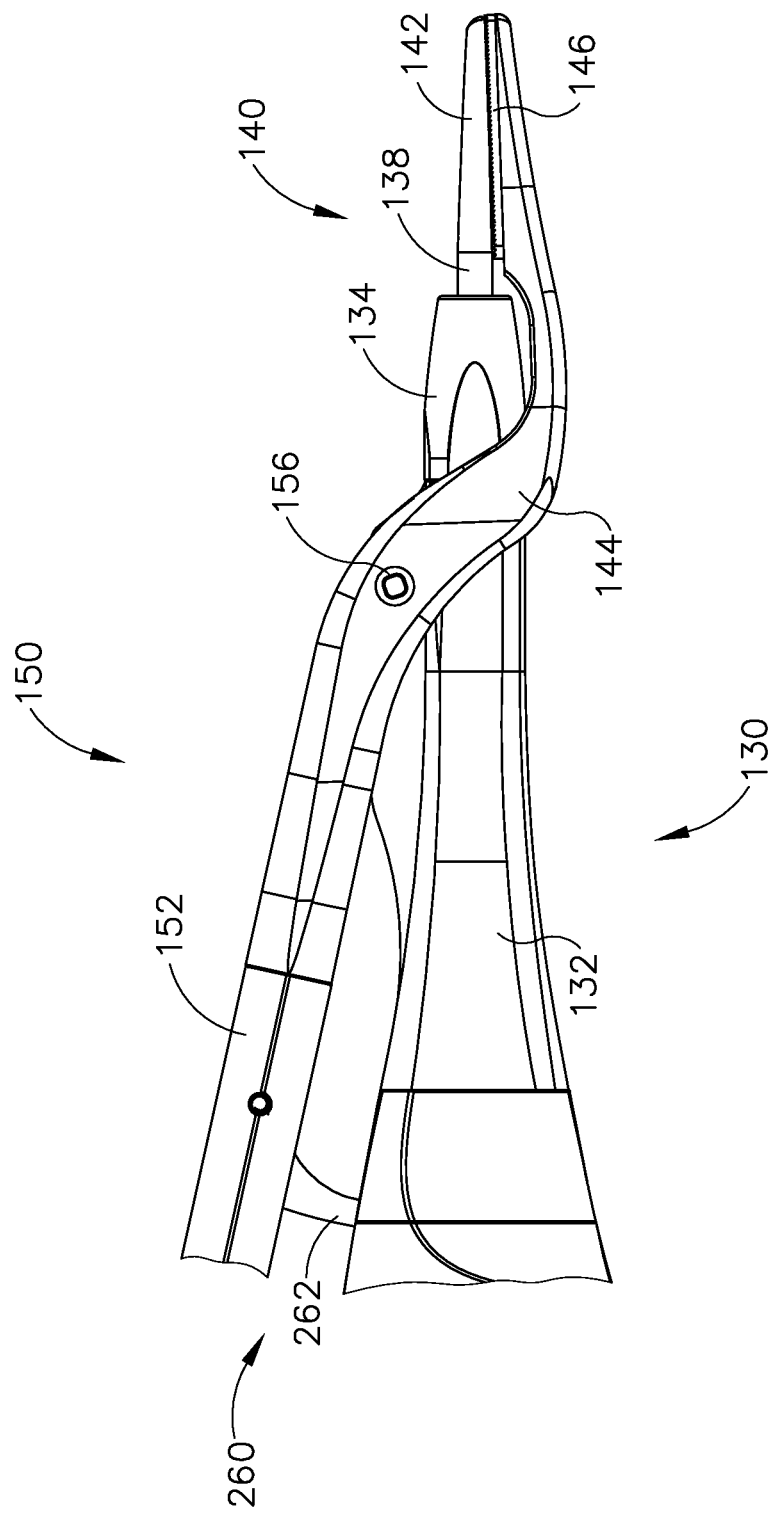
FIG. 12B depicts a side elevational view of the instrument of FIG. 12A, with the instrument moved into a closed configuration.

FIGS. 10-11D show another exemplary alternative ultrasonic blade rotation mechanism (240) that may be readily incorporated into instrument (100). Rotation mechanism (240) of the present example comprises a motor (242) secured to a proximal end of waveguide (138). Waveguide (138) of the present example is rotatably disposed within shaft assembly (130) such that waveguide (138) is rotatable relative to shaft assembly (130). Motor (242) is configured to rotate waveguide (138) and ultrasonic blade (142) within shaft assembly (130). Motor (242) is operable to turn in both clockwise and counter clockwise directions. Motor (242) may comprise a hub motor, a hollow shaft motor, a hollow shaft pancake motor, or any other type of motor appropriate to cause rotation of waveguide (138). As will be described in greater detail below, motor (242) of the present example is configured to rotate waveguide (138) and ultrasonic blade (142) in response to pivotal movement of clamp arm assembly (150) between the open position and the closed position. In some instances, one or more reed switches, hall effect sensors, and/or other kind(s) of position sensitive sensor(s) is/are used to sense pivotal position of clamp arm assembly (150) relative to shaft assembly (130). Such sensor(s) may thus be used to activate motor (242) once clamp arm assembly (150) reaches a particular position relative to shaft assembly (130). Other suitable ways in which motor (242) may be activated will be apparent to those of ordinary skill in the art in view of the teachings herein.

FIGS. 11A-11D show the rotation of waveguide (138) and ultrasonic blade (142) via motor (242) as clamp arm assembly (150) moves toward the closed position. As shown in FIG. 11A, in the open position, the distal tip of ultrasonic blade (142) is angled downwardly. As clamp arm assembly (150) is moved toward the closed position through a first range of motion, clamp pad (146) of clamp arm (144) contacts the downwardly angled distal tip of ultrasonic blade (142) as shown in FIG. 11B. Once clamp arm assembly (150) reaches this position, motor (242) rotates waveguide (138) and ultrasonic blade (142) until ultrasonic blade (142) is substantially parallel with clamp pad (146), and clamp arm assembly (150) is pivoted further through a second range of motion to bring clamp pad (146) in full apposition with ultrasonic blade (142), as shown in FIG. 11C. This rotation of ultrasonic blade (142) causes the force applied by clamp arm (144) to transition along the curved profile of ultrasonic blade (142) from the distal tip of ultrasonic blade (142) proximally toward waveguide (138), along the full length of ultrasonic blade (142). With clamp arm assembly (150) remaining in the closed position, motor (242) continues to rotate waveguide (138) and ultrasonic blade (142) until the distal tip of ultrasonic blade (142) is angled upwardly as shown in FIG. 11D. This rotation of ultrasonic blade (142) causes the force applied by clamp arm (144) to transition further proximally along the curved profile of ultrasonic blade (142) toward waveguide (138). Thus, the sequence shown in FIGS. 11A-11D show a rolling contact between ultrasonic blade (142) and clamp pad (146) that begins at the distal end of ultrasonic blade (142) and transitions proximally to the proximal end of ultrasonic blade (142).

In some other versions, motor (242) rotates in the opposite direction such that the rolling contact between ultrasonic blade (142) and clamp pad (146) that begins at the proximal end of ultrasonic blade (142) and transitions distally to the distal end of ultrasonic blade (142). It should also be understood that motor (242) may be operated to provide a rocking motion through ultrasonic blade (142) such that motor (242) drives blade in a reciprocating angular motion of less than 360°. Other suitable ways in which motor (242) may be used to controllably vary the relationship between ultrasonic blade (142) and clamp pad (146) will be apparent to those of ordinary skill in the art in view of the teachings herein. While rotation mechanism (240) is discussed as being used with instrument (100) in the present example, it should be understood that rotation mechanism (240) may also be readily incorporated into instrument (10).

D. Fourth Exemplary Ultrasonic Blade Rotation Mechanism

FIGS. 12A-13B show yet another exemplary alternative ultrasonic blade rotation mechanism (260) that may be readily incorporated into instrument (100). Rotation mechanism (260) of the present example comprises an elongate member (262) extending downwardly from shank (152). Waveguide (138) of the present example is rotatably disposed within shaft assembly (130) such that waveguide (138) is rotatable relative to shaft assembly (130). Elongate member (262) is configured to move within a passageway (264) in shaft assembly (130) as clamp arm assembly (150) is moved between the open position and the closed position. As will be described in greater detail below, movement of elongate member (262) within passageway (264) causes rotation of waveguide (138) and ultrasonic blade (142) as clamp arm assembly (150) approaches the closed position.

Figure 13A:
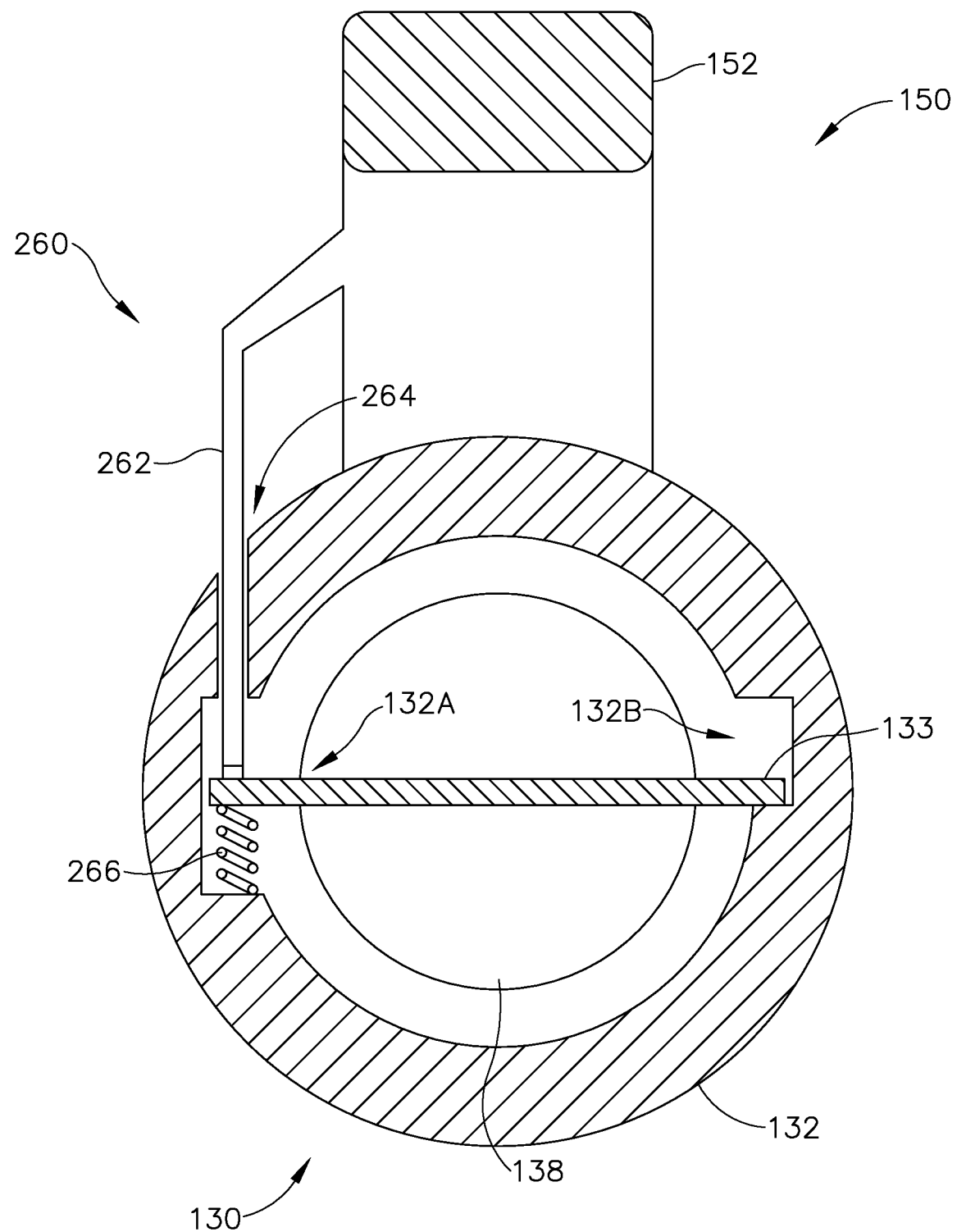
FIG. 13A depicts a cross-sectional view of the instrument of FIG. 12A, with the instrument in the open configuration and with an ultrasonic blade in a first rotational position.
Figure 13B:
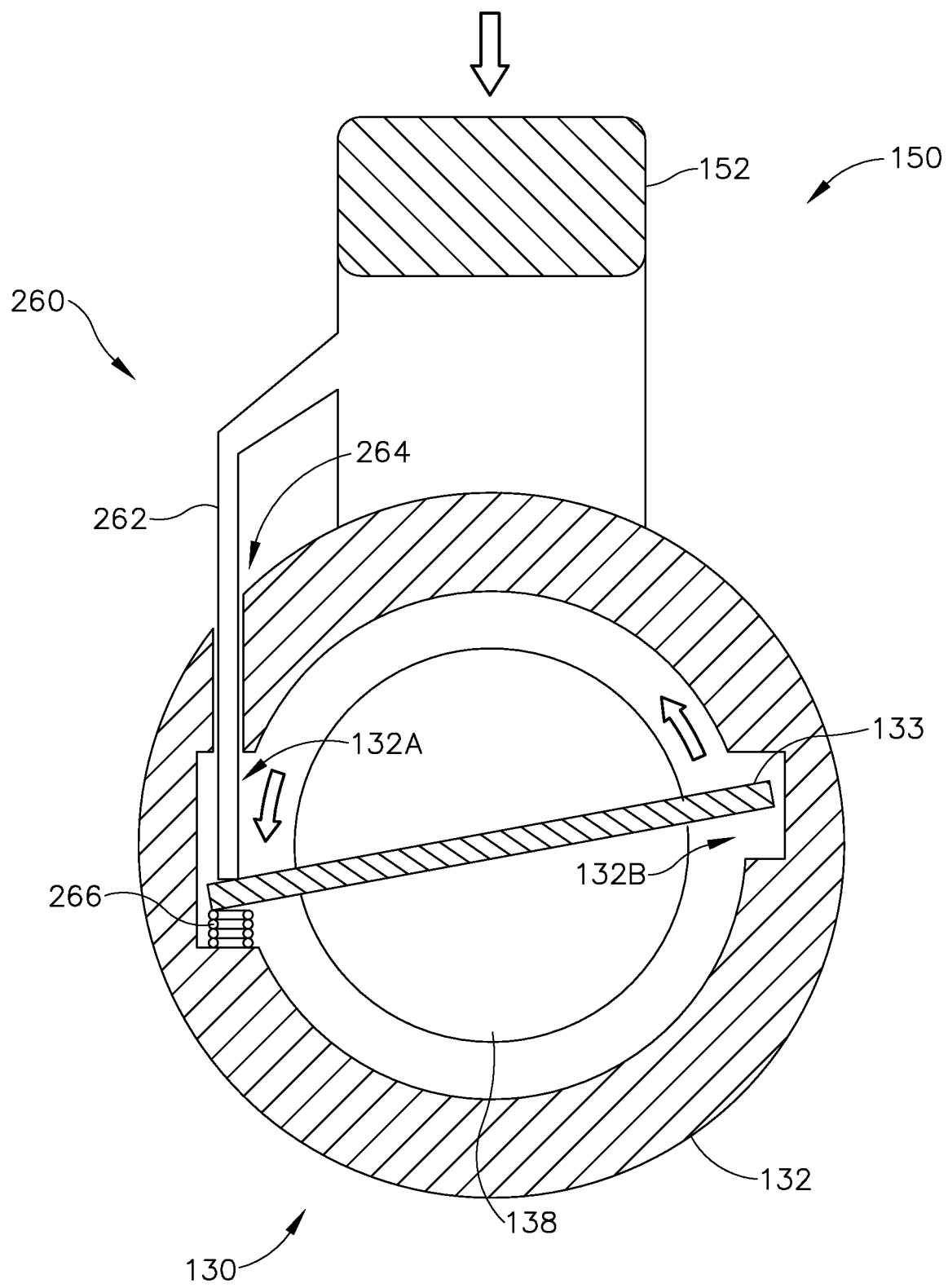
FIG. 13B depicts a cross-sectional view of the instrument of FIG. 12A, with the instrument moved into the closed configuration and with the ultrasonic blade rotated into a second rotational position.

As shown in FIGS. 13A-13B, the interior of outer sheath (132) of the present example presents a first recess (132A) and a second recess (132B). Pin (133) extends transversely through waveguide (138) such that a first end of pin (133) is disposed within first recess (132A) and a second end of pin (133) is disposed within second recess (132B). Pin (133) is located at a position along the length of waveguide (138) corresponding to a node associated with resonant ultrasonic vibrations communicated through waveguide (138). FIG. 13A shows waveguide (138) a position wherein ultrasonic blade (142) is substantially parallel to clamp pad (142). In this position, the first end of pin (133) rests upon a spring (266) positioned within first recess (132A). Also in this position, the second end of pin (133) rests upon a bottom surface of second recess (132B). As clamp arm assembly (150) is moved toward into a substantially closed position, as shown n FIG. 13A, a bottom tip of elongate member (262) contacts the first end of pin (133). As clamp arm assembly (150) is moved into the closed position the bottom tip of elongate member (262) drives the first end of pin (133) downwardly to thereby rotate waveguide (138) counterclockwise about the longitudinal axis of waveguide (138) as shown in FIG. 13B.

In the present example, ultrasonic blade (142) is configured to reach a state of full apposition with clamp pad (146) along the length of ultrasonic blade (142) and clamp pad (146) once clamp arm assembly (150) reaches the position shown in FIG. 13A. As clamp arm assembly (150) is driven further toward shaft assembly (130) to rotate waveguide (138) as shown in FIG. 13B, the curved configuration of ultrasonic blade (142) and the rotation of ultrasonic blade (142) together provide a distally advancing rolling engagement, such that an increased amount of compression force is applied between the distal end of ultrasonic blade (142) and clamp pad (146). Thus, the compression force between the distal end of ultrasonic blade (142) and clamp pad (146) increases during the transition from the configuration shown in FIG. 13A to the configuration shown in FIG. 13B. This increase in distal compression may prevent formation of a tissue tag or cut a tissue tag at the distal end of end effector (140). As soon as the operator relaxes their grip on grip rings (124, 154), allowing clamp arm assembly (150) to pivot back away from shaft assembly (130), the resilient bias of spring (266) may urge pin (133) back to the position shown in FIG. 13A.

While rotation mechanism (260) is discussed as being incorporated into instrument (100) in the present example, it should be understood that rotation mechanism (260) may be readily incorporated into instrument (10).

E. Fifth Exemplary Ultrasonic Blade Rotation Mechanism

Figure 14:
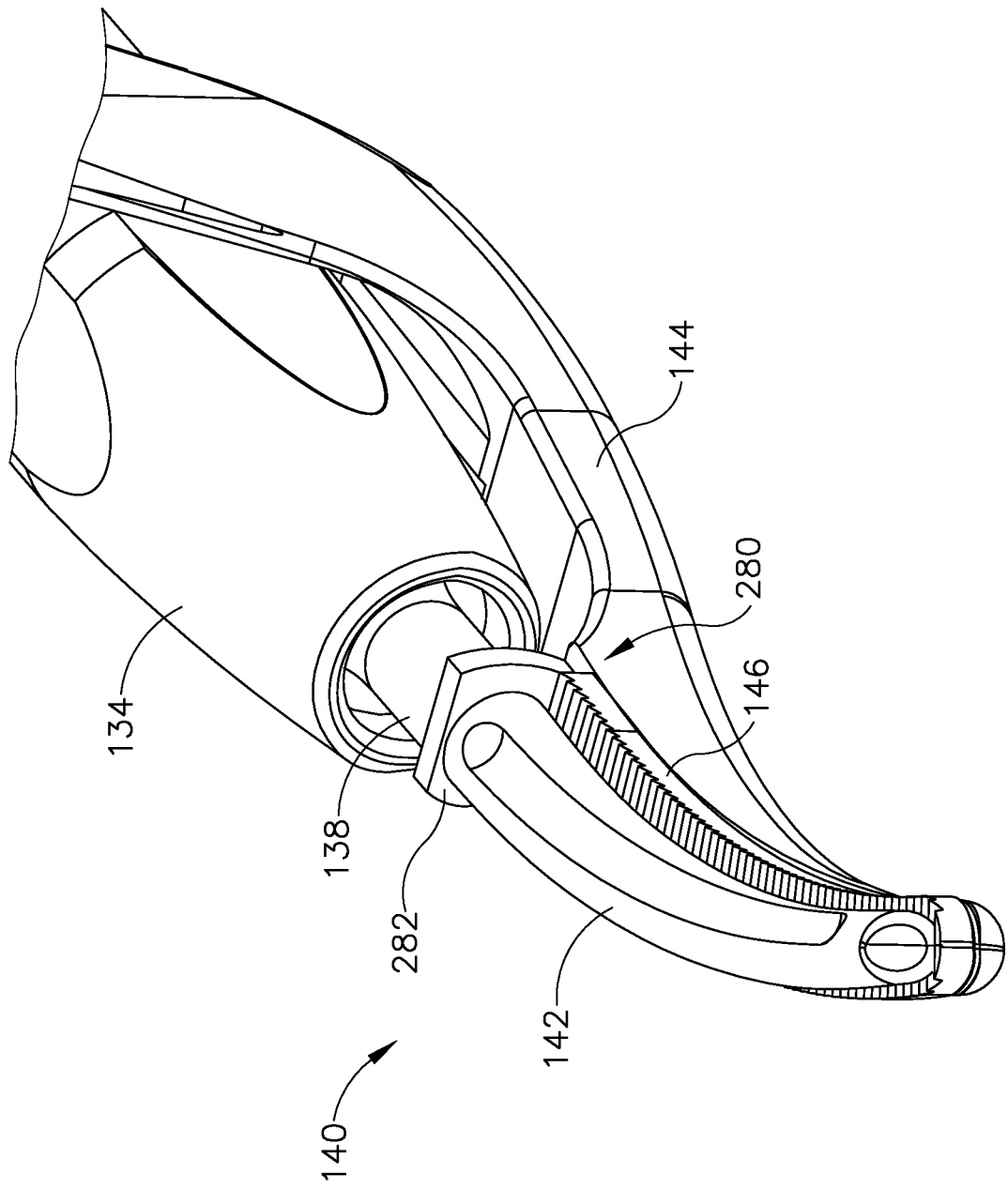
FIG. 14 depicts a perspective view of another variation of the instrument of FIG. 4 having yet another exemplary alternative ultrasonic blade rotation mechanism.
Figure 15C:
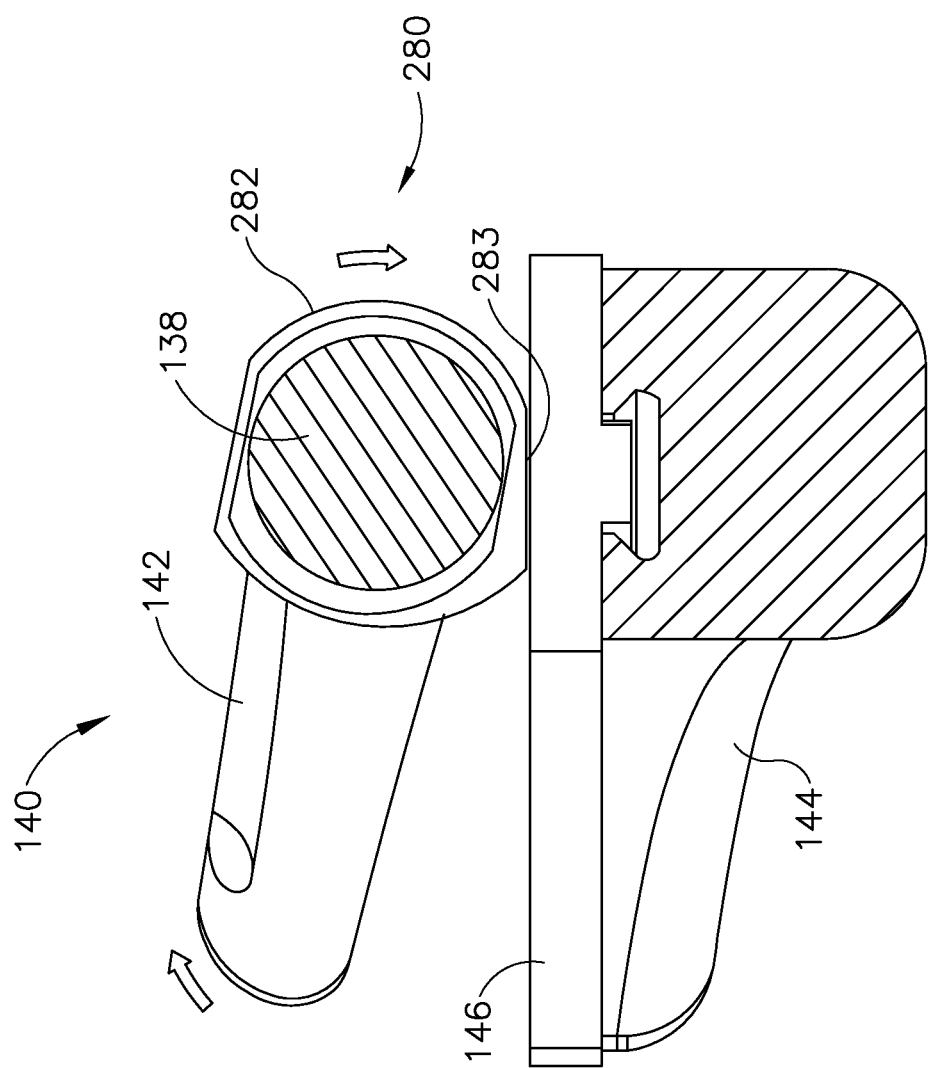
FIG. 15C depicts a cross-sectional view of the instrument of FIG. 14, with the instrument moved into a completely closed configuration and with the ultrasonic blade rotated into a third rotational position.

FIGS. 14-15C show yet another exemplary alternative ultrasonic blade rotation mechanism (280) that may be readily incorporated into instrument (100). Rotation mechanism (280) of the present example comprises an elastomeric bushing (282) secured to a distal end of waveguide (138), just proximal to ultrasonic blade (142). Waveguide (138) of the present example is rotatably disposed within shaft assembly (130) such that waveguide (138) is rotatable relative to shaft assembly (130) and is biased toward a counter-clockwise rotational position, as shown in FIG. 15A, such that the distal tip of ultrasonic blade (142) is angled downwardly to first contact clamp pad (146) as clamp arm assembly (150) is pivoted toward shaft assembly (130). As best seen in FIG. 14, bushing (282) is secured to an exterior of waveguide (138). As shown in FIGS. 15A-15C, a bottom of bushing (282) presents a flat surface (283). Flat surface (283) is formed at an angle that is oblique relative to a bottom surface of ultrasonic blade (142) and relative to an opposing surface of clamp pad (146). As will be described in greater detail below, flat surface (283) of bushing (282) is configured to bear against clamp pad (146) of clamp arm (144) as clamp arm assembly (150) is pivoted further toward clamp arm assembly (130), thereby causing waveguide (138) and ultrasonic blade (142) to rotate clockwise such that ultrasonic blade (142) reaches a state of full apposition with clamp pad (146); and in some versions, ultimately to a position where the distal tip of ultrasonic blade (142) is angled upwardly and away from clamp pad (146).

FIGS. 15A-15C show the rotation of waveguide (138) and ultrasonic blade (142) as clamp arm assembly (150) is pivoted toward shaft assembly (130) to provide varying degrees of closure. As previously discussed, waveguide (138) is biased toward a counter-clockwise rotational position, as shown in FIG. 15A, such that when clamp arm assembly (150) in the first closed position, the distal tip of ultrasonic blade (142) is angled downwardly and in contact with clamp pad (146). As clamp arm assembly (150) is moved toward a further closed position, a corner of flat surface (283) contacts clamp pad (146). This contact begins to rotate waveguide (138) clockwise as clamp arm assembly (150) is moved further toward the closed position as shown in FIG. 15B. At this stage the full length of ultrasonic blade (142) may or may not reach a state of apposition with clamp pad (146). As clamp arm assembly (150) is pivoted further toward shaft assembly (130), substantially all of flat surface (283) contacts clamp pad (146) to further rotate waveguide (138) and ultrasonic blade (142) clockwise such that the distal tip of ultrasonic blade (142) is angled upwardly and away from clamp pad (146) as shown in FIG. 15C. Thus, the sequence shown in FIGS. 15A-15C provides a rolling contact beginning at the distal end of ultrasonic blade (142) and travelling proximally to the proximal end of ultrasonic blade (142).

In some versions, a resilient member such as a torsion spring, elastomeric bushing, and/or other feature is used to rotationally bias ultrasonic blade (142) to the orientation shown in FIG. 15A. Thus, when the operator relaxes their grip on grip rings (124, 154), the bias of the resilient member rotates ultrasonic blade (142) back from the orientation shown in FIG. 15C to the orientation shown in FIG. 15A. Alternatively, the resilience of bushing (282) itself may suffice to rotate ultrasonic blade (142) back from the orientation shown in FIG. 15C to the orientation shown in FIG. 15A when the operator relaxes their grip on grip rings (124, 154).

Also in some versions, a detent feature is included to provide audible and/or tactile feedback indicating when end effector (140) is transitioning from the state shown in FIG. 15A to the state shown in FIG. 15B; and/or when end effector (140) is transitioning from the state shown in FIG. 15B to the state shown in FIG. 15C. It should also be understood that such detent features may be provided in various other examples described herein, including but not limited to the other examples described herein providing a rolling contact between an ultrasonic blade (142) and clamp pad (146).

While rotation mechanism (260) is discussed as being incorporated into instrument (100) in the present example, it should be understood that rotation mechanism (260) may be readily incorporated into instrument (10). For instance, bushing (282) may be secured to a distal end of waveguide (38) of instrument (10) such that bushing (282) bears against clamp arm (44) to thereby cause rotation of waveguide (38).

F. Sixth Exemplary Ultrasonic Blade Rotation Mechanism

Figure 16:
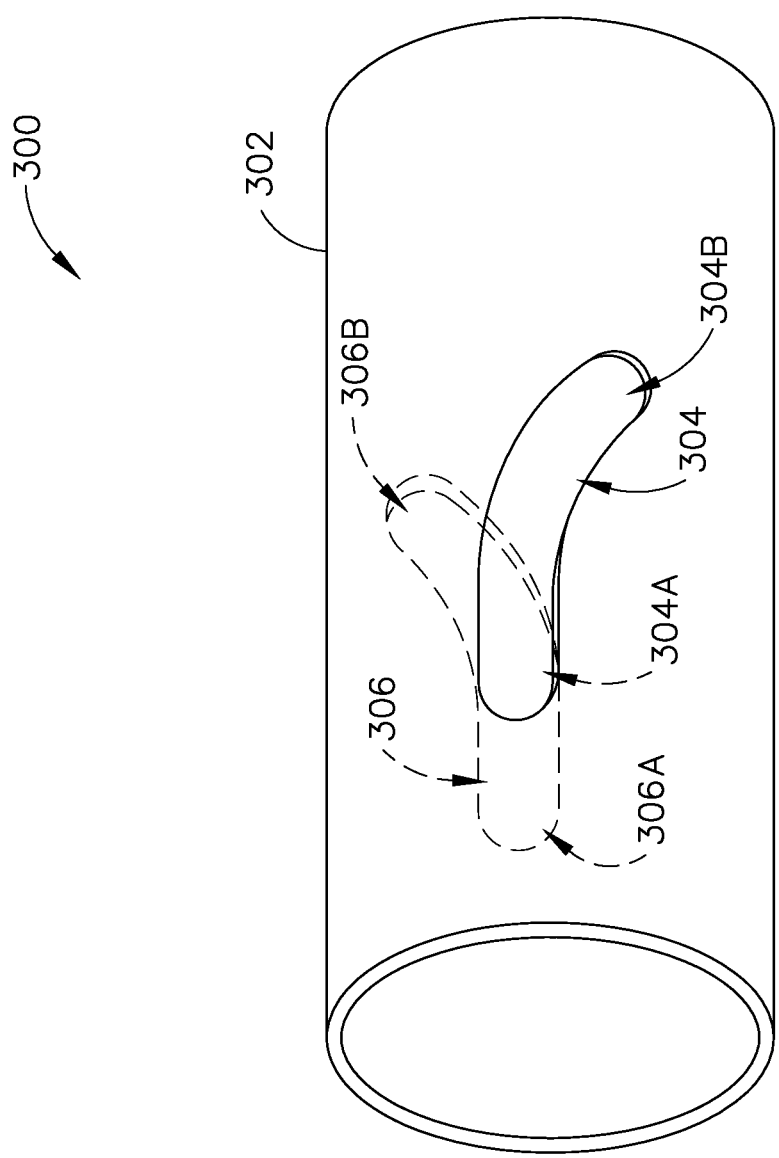
FIG. 16 depicts a perspective view of a barrel cam of an ultrasonic blade rotation mechanism suitable for incorporation into the instrument of FIG. 1.
Figure 17A:
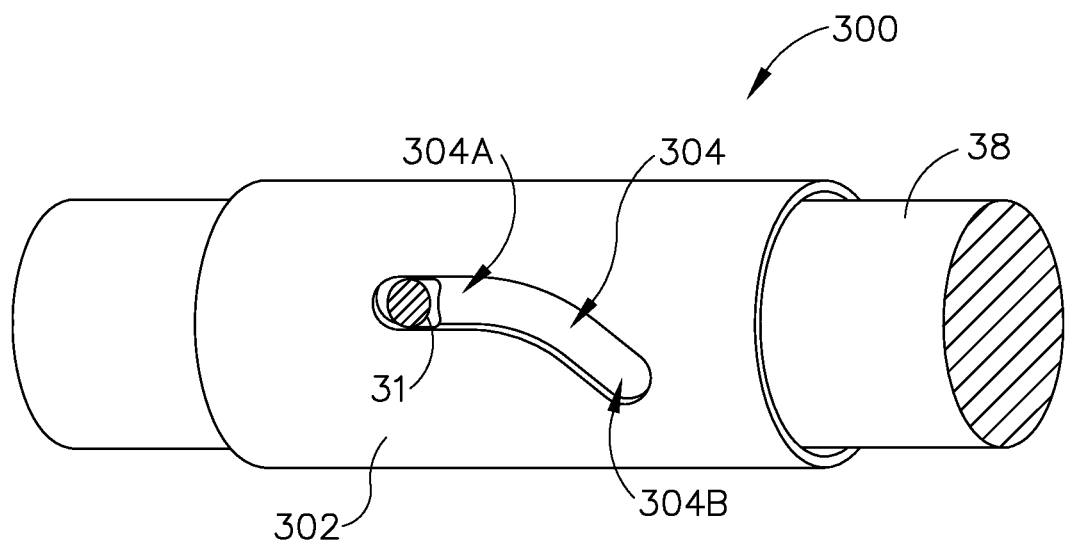
FIG. 17A depicts a perspective view of the barrel cam of FIG. 16 and an ultrasonic blade, with the ultrasonic blade in a first longitudinal position and in a first rotational position.
Figure 17B:
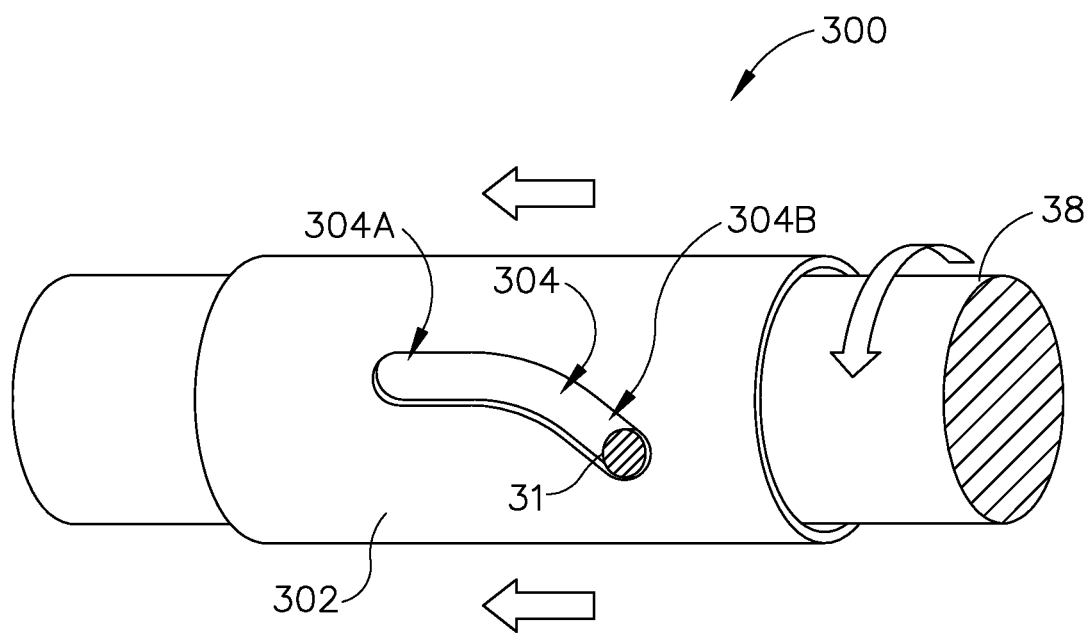
FIG. 17B depicts a perspective view of the barrel cam of FIG. 16 and the ultrasonic blade, with the ultrasonic blade moved into a second longitudinal position and rotated into a second rotational position.

FIGS. 16-17B show yet another exemplary alternative ultrasonic blade rotation mechanism (300) that may be readily incorporated into instrument (10). Rotation mechanism (300) of the present example comprises an exemplary alternative inner tube (302). Inner tube (302) of the present example is configured to operate substantially similar to inner tube (34) discussed above except for the differences discussed below. In particular, longitudinal translation of inner tube (302) relative to outer sheath (32) causes actuation of clamp arm (44) at end effector (40). Waveguide (38) of the present example is rotatably disposed within inner tube (302) such that waveguide (38) is rotatable relative to shaft assembly (30). Inner tube (302) comprises a pair of camming channels (304, 306) formed in diametrically opposite sides of inner tube (302). While inner tube (302) is translatable relative to outer sheath (32) in this example, inner tube (302) does not rotate relative to outer sheath (32) in this example.

As discussed above with reference to instrument (10), waveguide (38) is secured within shaft assembly (30) via a pin (31), which passes transversely through waveguide (38). Pin (31) is located at a position along the length of waveguide (38) corresponding to a node associated with resonant ultrasonic vibrations communicated through waveguide (38). As will be described in greater detail below, rotation of pin (31) about the longitudinal axis of waveguide (38) causes concurrent rotation of waveguide (38) about the longitudinal axis of waveguide (38). As shown in FIGS. 17A and 17B, pin (31) extends through waveguide (38) and inner tube (302) such that a first end of pin (31) is slidably disposed within camming channel (304) and such that a second end of pin (31) is slidably disposed within camming channel (306). As will be discussed in more detail below, pin (31) is operable to slide within camming channels (304, 306) as inner tube (302) translates longitudinally relative to waveguide (38). This sliding of pin (31) within camming channels (304, 306) causes rotation of pin (31) and waveguide (38) about the longitudinal axis of waveguide (38).

FIGS. 17A and 17B show the steps of rotating waveguide (38) via longitudinal translation of inner tube (302) relative to waveguide (38). With clamp arm (44) in an open position relative to ultrasonic blade (42), inner tube (302) is in a first longitudinal position as shown in FIG. 17A. In this first longitudinal position, pin (31) is disposed within a longitudinal portion (304A, 306A) of camming channels (304, 306). At this stage, ultrasonic blade (42) and clamp arm (44) are both oriented as shown in FIG. 3A. As inner tube (302) is translated longitudinally through a first range of motion relative to waveguide (38) and outer sheath (32), pin (31) slides within camming channels (304, 306) through longitudinal portions (304A, 306A) until clamp arm (44) reaches a closed position relative to ultrasonic blade (42), similar to the configuration shown in FIG. 3B. Alternatively, clamp arm (44) may be in a substantially closed position at this stage (e.g., such that clamp arm (44) defines a sharply acute angle with ultrasonic blade (42), substantially near the closed position).

As inner tube (302) continues to translate longitudinally through a second range of motion relative to waveguide (38) and outer sheath (32), pin (31) slides through slanted portions (304B, 306B) of camming channels (304, 306), as shown in FIG. 17B. It should be understood that, as pin (31) is slid into slanted portions (304B, 306B), clamp arm (44) reaches or remains in a closed position relative to ultrasonic blade (42). As shown in FIG. 17B, movement of pin (31) within camming channels (304, 306) into slanted portions (304B, 306B) causes rotation of waveguide (38) and thus ultrasonic blade (42) about the longitudinal axis of waveguide (38). Thus, it should be understood that ultrasonic blade (42) rotates as clamp arm (44) pivots toward ultrasonic blade (42) and clamps tissue there between.

In the present example, ultrasonic blade (42) is configured to reach a state of full apposition with clamp pad (46) along the length of ultrasonic blade (42) and clamp pad (46) (e.g., as shown in FIG. 3B) once pin (31) reaches the transition between longitudinal portions (304A, 306A) and slanted portions (304B, 306B). As inner tube (302) is translated further relative to waveguide (38) and outer sheath (32) to rotate waveguide (38) as shown in FIG. 17B, the curved configuration of ultrasonic blade (42) and the rotation of ultrasonic blade (42) together provide a distally advancing rolling engagement, such that an increased amount of compression force is applied between the distal end of ultrasonic blade (42) and clamp pad (46). Thus, the compression force between the distal end of ultrasonic blade (42) and clamp pad (46) increases during the transition from the configuration shown in FIG. 17A to the configuration shown in FIG. 17B. This increase in distal compression may prevent formation of a tissue tag or cut a tissue tag at the distal end of end effector (40).

While rotation mechanism (300) is discussed as being used with instrument (10) in the present example, it should be understood that rotation mechanism (300) may be readily incorporated into instrument (100).

G. Seventh Exemplary Ultrasonic Blade Rotation Mechanism

Figure 18:
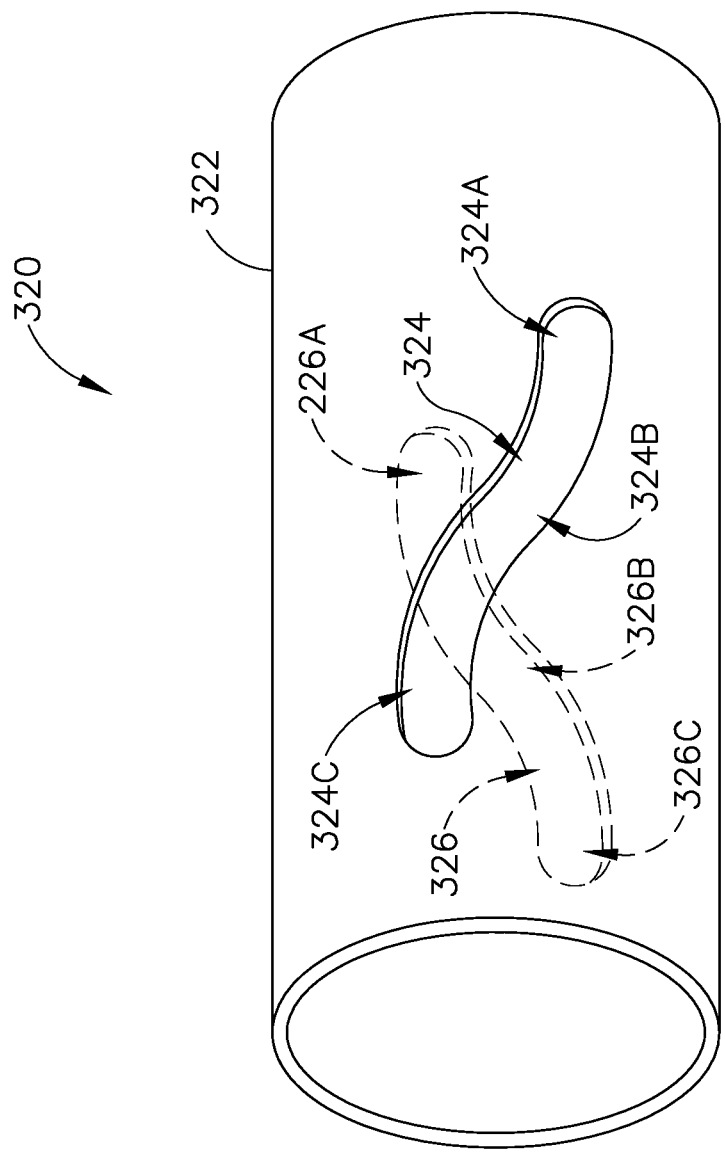
FIG. 18 depicts a perspective view of an inner tube of an ultrasonic blade rotation mechanism suitable for incorporation into the instrument of FIG. 1.
Figure 19A:
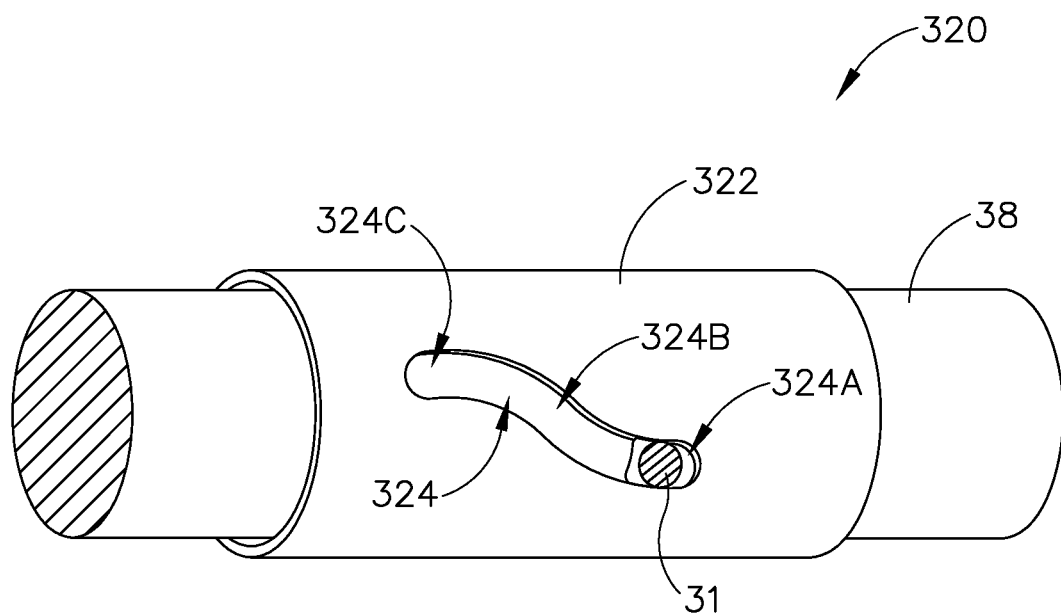
FIG. 19A depicts a perspective view of the inner tube of FIG. 18 and an ultrasonic blade, with the inner tube in a first longitudinal position and with the ultrasonic blade in a first rotational position.
Figure 19B:
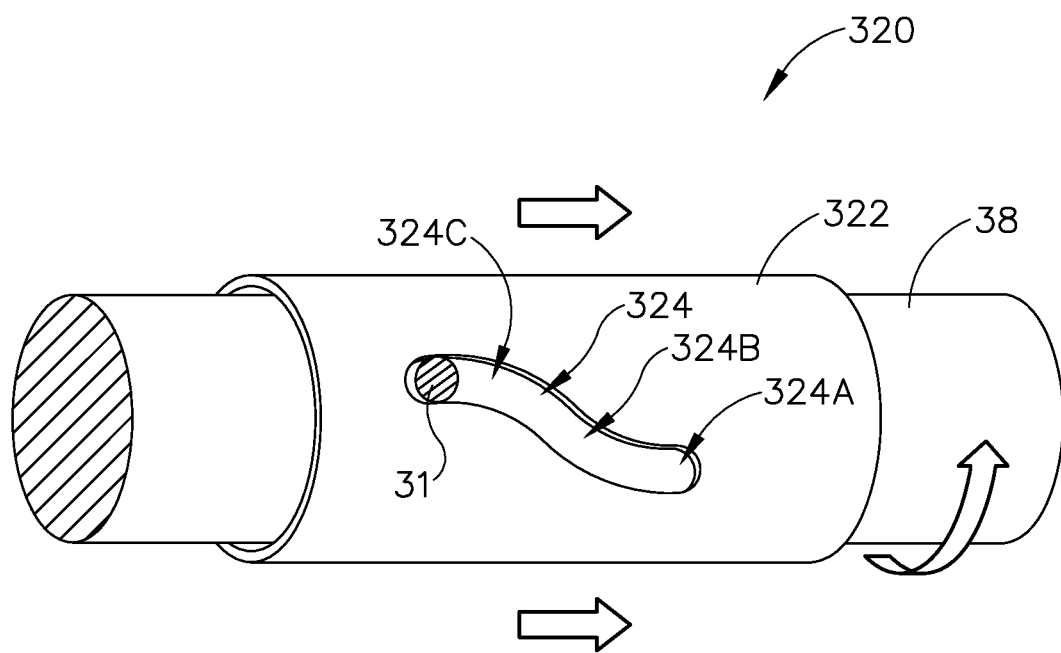
FIG. 19B depicts a perspective view of the inner tube of FIG. 18 and the ultrasonic blade, with the inner tube moved into a second longitudinal position and with the ultrasonic blade rotated into a second rotational position.

FIGS. 18-19B show yet another exemplary alternative ultrasonic blade rotation mechanism (320) that may be readily incorporated into instrument (10). Rotation mechanism (320) of the present example comprises an exemplary alternative inner tube (322). Inner tube (322) of the present example is configured to operate substantially similar to inner tubes (34, 302) discussed above except for the differences discussed below. In particular, longitudinal translation of inner tube (322) relative to outer sheath (32) causes actuation of clamp arm (44) at end effector (40). Waveguide (38) of the present example is rotatably disposed within inner tube (322) such that waveguide (38) is rotatable relative to shaft assembly (30). Inner tube (322) comprises a pair of camming channels (324, 326) formed in diametrically opposite sides of inner tube (322). While inner tube (322) is translatable relative to outer sheath (32) in this example, inner tube (322) does not rotate relative to outer sheath (32) in this example.

As discussed above with reference to instrument (10), waveguide (38) is secured within shaft assembly (30) via a pin (31), which passes through waveguide (38) and shaft assembly (30). Pin (31) is located at a position along the length of waveguide (38) corresponding to a node associated with resonant ultrasonic vibrations communicated through waveguide (38). As will be described in greater detail below, rotation of pin (31) about the longitudinal axis of waveguide (38) causes concurrent rotation of waveguide (38) about the longitudinal axis of waveguide (38). As shown in FIGS. 19A and 19B, pin (31) extends through waveguide (38) and inner tube (302) such that a first end of pin (31) is slidably disposed within camming channel (324) and such that a second end of pin (31) is slidably disposed within camming channel (326). As will be discussed in more detail below, pin (31) is operable to slide within camming channels (324, 326) as inner tube (322) translates longitudinally relative to waveguide (38). This sliding within camming channels (324, 326) causes rotation of waveguide (38) about the longitudinal axis of waveguide (38).

FIGS. 19A and 19B show the steps of rotating waveguide (38) via longitudinal translation of inner tube (322) relative to waveguide (38). With clamp arm (44) in an open position relative to ultrasonic blade (42), inner tube (322) is in a first longitudinal position as shown in FIG. 19A. In this first longitudinal position, pin (31) is disposed within a proximal longitudinal portion (324A, 326A) of camming channels (324, 326). At this stage, ultrasonic blade (42) and clamp arm (44) are both oriented as shown in FIG. 3A. As inner tube (322) is translated longitudinally through a first range of motion relative to waveguide (38) and outer sheath (32), pin (31) slides within camming channels (324, 326) through proximal longitudinal portions (324A, 326A) until clamp arm (44) reaches a closed position relative to ultrasonic blade (42), similar to the configuration shown in FIG. 3B. Alternatively, clamp arm (44) may be in a substantially closed position at this stage (e.g., such that clamp arm (44) defines a sharply acute angle with ultrasonic blade (42), substantially near the closed position).

As inner tube (322) continues to translate longitudinally through a second range of motion relative to waveguide (38) and outer sheath (32), pin (31) slides through slanted portions (324B, 326B) and into distal longitudinal portions (324C, 326C) as shown in FIG. 19B. It should be understood that, as pin (31) slides through slanted portions (324B, 326B) and into distal longitudinal portions (324C, 326C), clamp arm (44) reaches or remains a closed position relative to ultrasonic blade (42). As shown in FIG. 19B, movement of pin (31) within camming channels (324, 326) through slanted portions (324B, 326B) causes rotation of waveguide (38) and thus ultrasonic blade (42). Thus, it should be understood that ultrasonic blade (42) rotates as clamp arm (44) pivots toward ultrasonic blade (42) and clamps tissue there between.

In the present example, ultrasonic blade (42) is configured to reach a state of full apposition with clamp pad (46) along the length of ultrasonic blade (42) and clamp pad (46) (e.g., as shown in FIG. 3B) once pin (31) reaches slanted portions (324B, 326B). As inner tube (322) is translated further relative to waveguide (38) and outer sheath (32) to rotate waveguide (38) as shown in FIG. 19B, the curved configuration of ultrasonic blade (42) and the rotation of ultrasonic blade (42) together provide a distally advancing rolling engagement, such that an increased amount of compression force is applied between the distal end of ultrasonic blade (42) and clamp pad (46). Thus, the compression force between the distal end of ultrasonic blade (42) and clamp pad (46) increases during the transition from the configuration shown in FIG. 19A to the configuration shown in FIG. 19B. This increase in distal compression may prevent formation of a tissue tag or cut a tissue tag at the distal end of end effector (40).

While rotation mechanism (320) is discussed as being used with instrument (10) in the present example, it should be understood that rotation mechanism (320) may be readily incorporated into instrument (100).

H. Eighth Exemplary Ultrasonic Blade Rotation Mechanism

Figure 20:
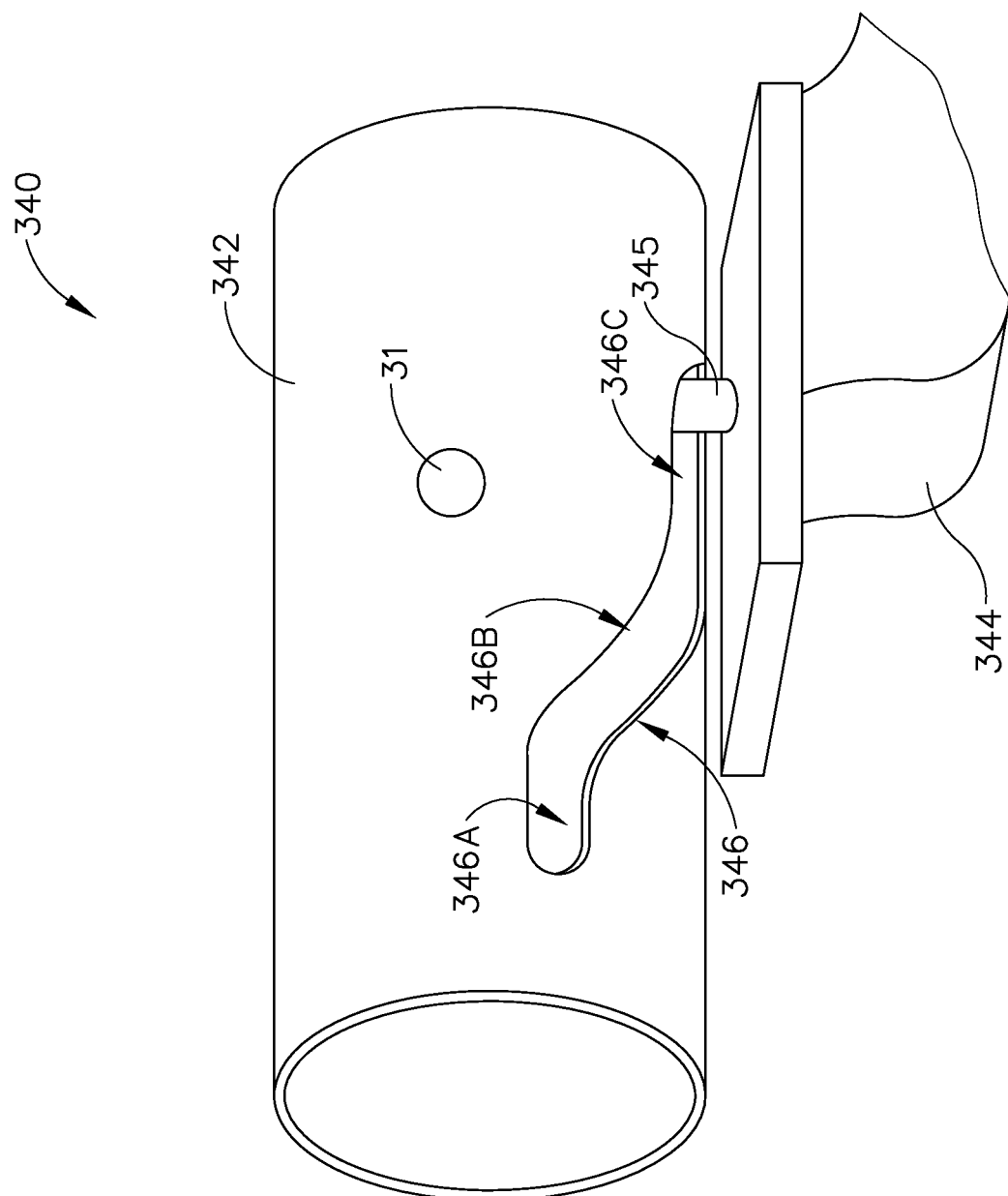
FIG. 20 depicts a perspective view of an inner tube and a yoke of an ultrasonic blade rotation mechanism suitable for incorporation into the instrument of FIG. 1.
Figure 21A:
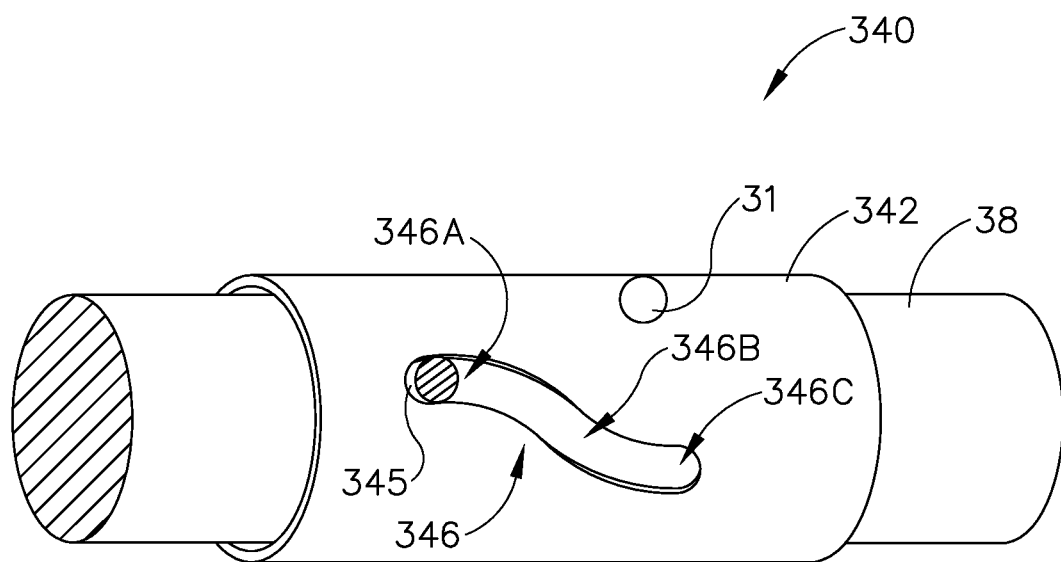
FIG. 21A depicts a perspective view of the inner tube of FIG. 20 and an ultrasonic blade, with the yoke in a first longitudinal position and with the inner tube and the ultrasonic blade in a first rotational position.
Figure 21B:
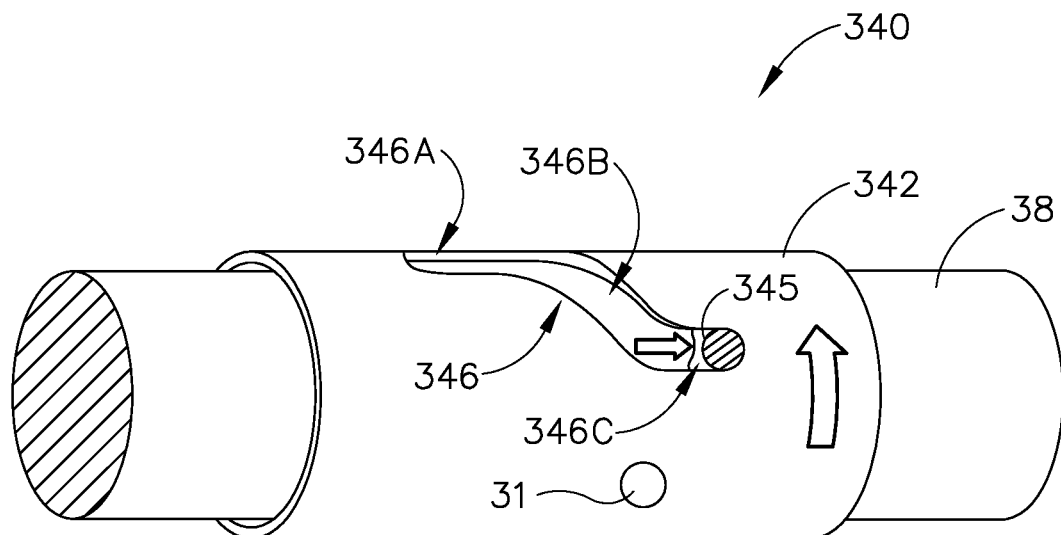
FIG. 21B depicts a perspective view of the inner tube of FIG. 20 and the ultrasonic blade, with the yoke moved into a second longitudinal position and with the inner tube and the ultrasonic blade rotated into a second rotational position.

FIGS. 20-21B show yet another exemplary alternative ultrasonic blade rotation mechanism (340) that may be readily incorporated into instrument (10). Rotation mechanism (340) of the present example comprises an exemplary alternative inner tube (342) and an exemplary triggering mechanism (344). Inner tube (342) of the present example is configured to operate substantially similar to inner tube (34) discussed above except for the differences discussed below. In particular, longitudinal translation of inner tube (342) relative to outer sheath (32) causes actuation of clamp arm (44) at end effector (40). Triggering mechanism (344) of the present example is mechanically coupled to trigger (28) such that pivoting of trigger (28) toward and away from pistol grip (24) causes actuation of triggering mechanism (344). As will be discussed in more detail below, actuation of triggering mechanism (344) causes rotation of waveguide (38).

Waveguide (38) of the present example is rotatably disposed within inner tube (342) such that waveguide (38) is rotatable relative to shaft assembly (30). As discussed above with reference to instrument (10), waveguide (38) is secured within shaft assembly (30) via a pin (31), which passes transversely through waveguide (38) and shaft assembly (30). In particular, in the present example, pin (31) passes through waveguide (38) and into inner tube (342) such that pin (31) rotates concurrently with inner tube (342). Pin (31) is located at a position along the length of waveguide (38) corresponding to a node associated with resonant ultrasonic vibrations communicated through waveguide (38). As will be described in greater detail below, rotation of pin (31) causes concurrent rotation of waveguide (38).

Inner tube (322) comprises a camming channel (346) formed in side of inner tube (342). Triggering mechanism (344) comprises a pin (345) projecting from a top surface of triggering mechanism (344) and into camming channel (346). Pin (345) is slidably disposed within camming channel (346). It should be understood that pin (35) extends into camming channel (346) but does not contact waveguide (38). As will be discussed in more detail below, pin (345) is operable to slide within camming channel (346) as inner tube (342) translates longitudinally. This sliding within camming channel (346) causes rotation of inner tube (342) and waveguide (38) about the longitudinal axis of waveguide via pin (31).

FIGS. 21A and 21B show the steps of rotating waveguide (38) via actuation of triggering mechanism (344). (Triggering mechanism (344), expect for pin (345), has been omitted from FIGS. 21A and 21B for the sake of clarity.) With clamp arm (44) in an open position, pin (345) of triggering mechanism (344) is in a first longitudinal position as shown in FIG. 21A. In this first longitudinal position, pin (345) is disposed within a distal longitudinal portion (346A) of camming channel (346). As triggering mechanism (344) is actuated, pin (345) is translated longitudinally within camming channel (346) such that pin (345) slides within camming channel (346) from distal longitudinal portion (346A) through a slanted portion (346B) and into a proximal longitudinal portion (346C) as shown in FIG. 21B. It should be understood that as pin (345) slides through slanted portion (346B) and into proximal longitudinal portion (346C), clamp arm (44) is pivoted into a closed position via longitudinal translation of inner tube (34) thereby clamping tissue within end effector (40). As shown in FIG. 21B, movement of pin (345) within camming channel (346) through slanted portion (346B) causes rotation of inner tube (342) and waveguide (38) via pin (31) and thus ultrasonic blade (42). Thus, it should be understood that ultrasonic blade (42) rotates as clamp arm (44) pivots toward ultrasonic blade (42) and clamps tissue therebetween.

In the present example, ultrasonic blade (42) is configured to reach a state of full apposition with clamp pad (46) along the length of ultrasonic blade (42) and clamp pad (46) (e.g., as shown in FIG. 3B) once pin (31) reaches slanted portion (346B). As pin (345) is driven further through channel (346) to rotate waveguide (38) as shown in FIG. 21B, the curved configuration of ultrasonic blade (42) and the rotation of ultrasonic blade (42) together provide a distally advancing rolling engagement, such that an increased amount of compression force is applied between the distal end of ultrasonic blade (42) and clamp pad (46). Thus, the compression force between the distal end of ultrasonic blade (42) and clamp pad (46) increases during the transition from the configuration shown in FIG. 21A to the configuration shown in FIG. 21B. This increase in distal compression may prevent formation of a tissue tag or cut a tissue tag at the distal end of end effector (40).

While rotation mechanism (340) is discussed as being used with instrument (10) in the present example, it should be understood that rotation mechanism (340) may be readily incorporated into instrument (100).

I. Ninth Exemplary Ultrasonic Blade Rotation Mechanism

Figure 22A:
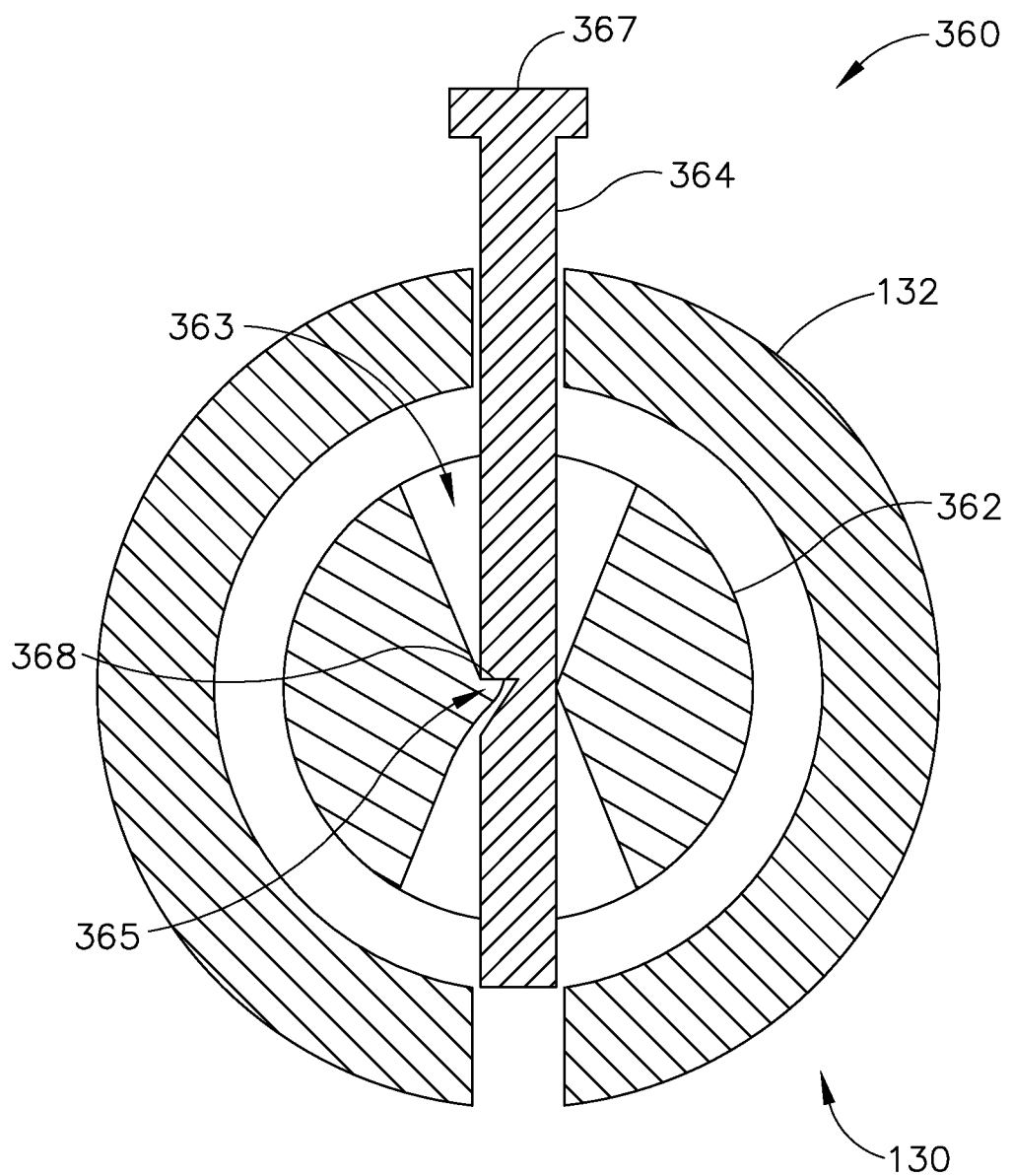
FIG. 22A depicts a cross-sectional view of yet another ultrasonic blade rotation mechanism suitable for incorporation into the instruments of FIG. 1 and FIG. 4, with a pin of the ultrasonic blade rotation mechanism in a first vertical position and with an ultrasonic blade in a first rotational position.
Figure 22B:
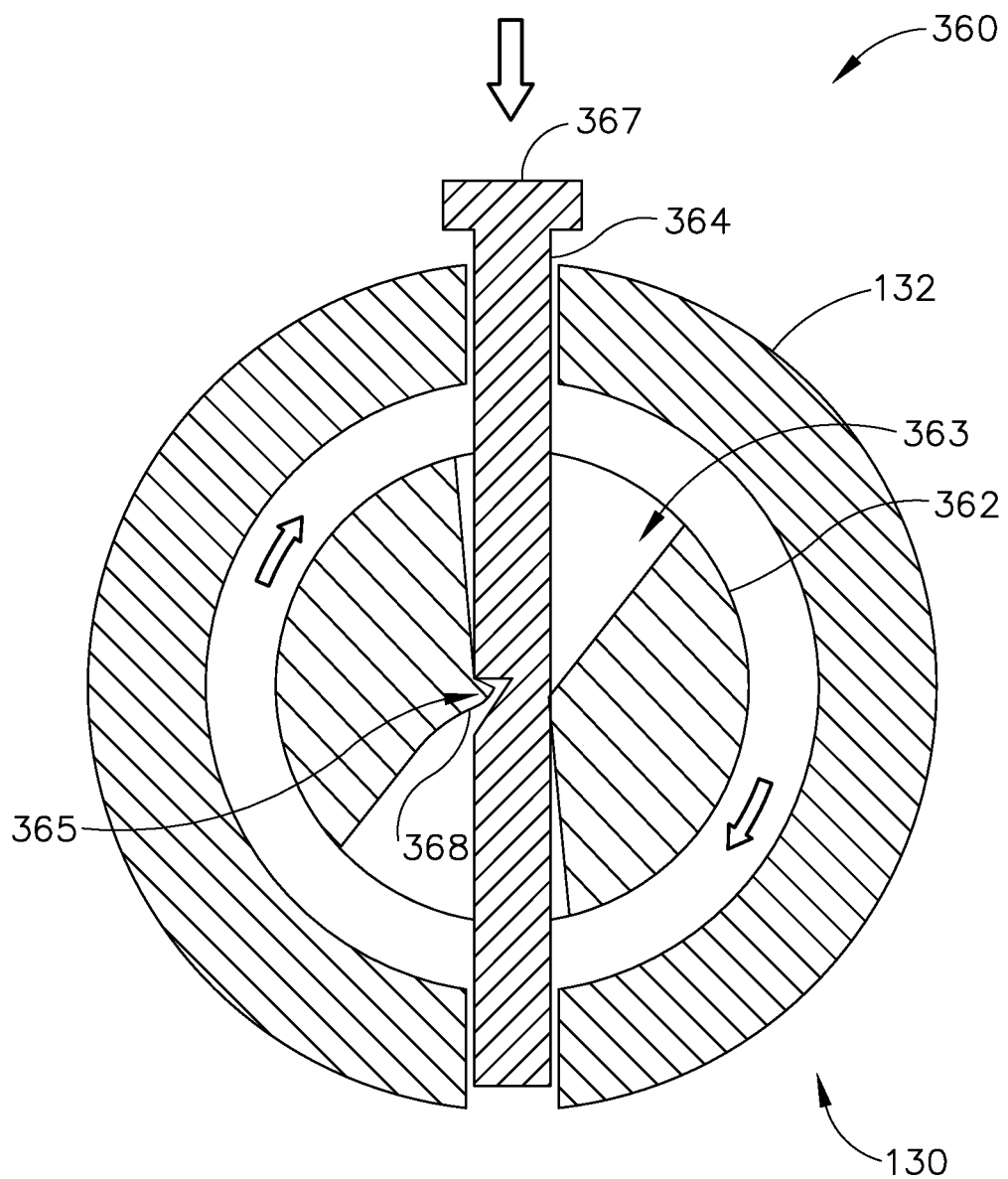
FIG. 22B depicts a cross-sectional view of the ultrasonic blade rotation mechanism of FIG. 22A, with the pin moved into a second vertical position and with the ultrasonic blade rotated into a second rotational position.
Figure 23:
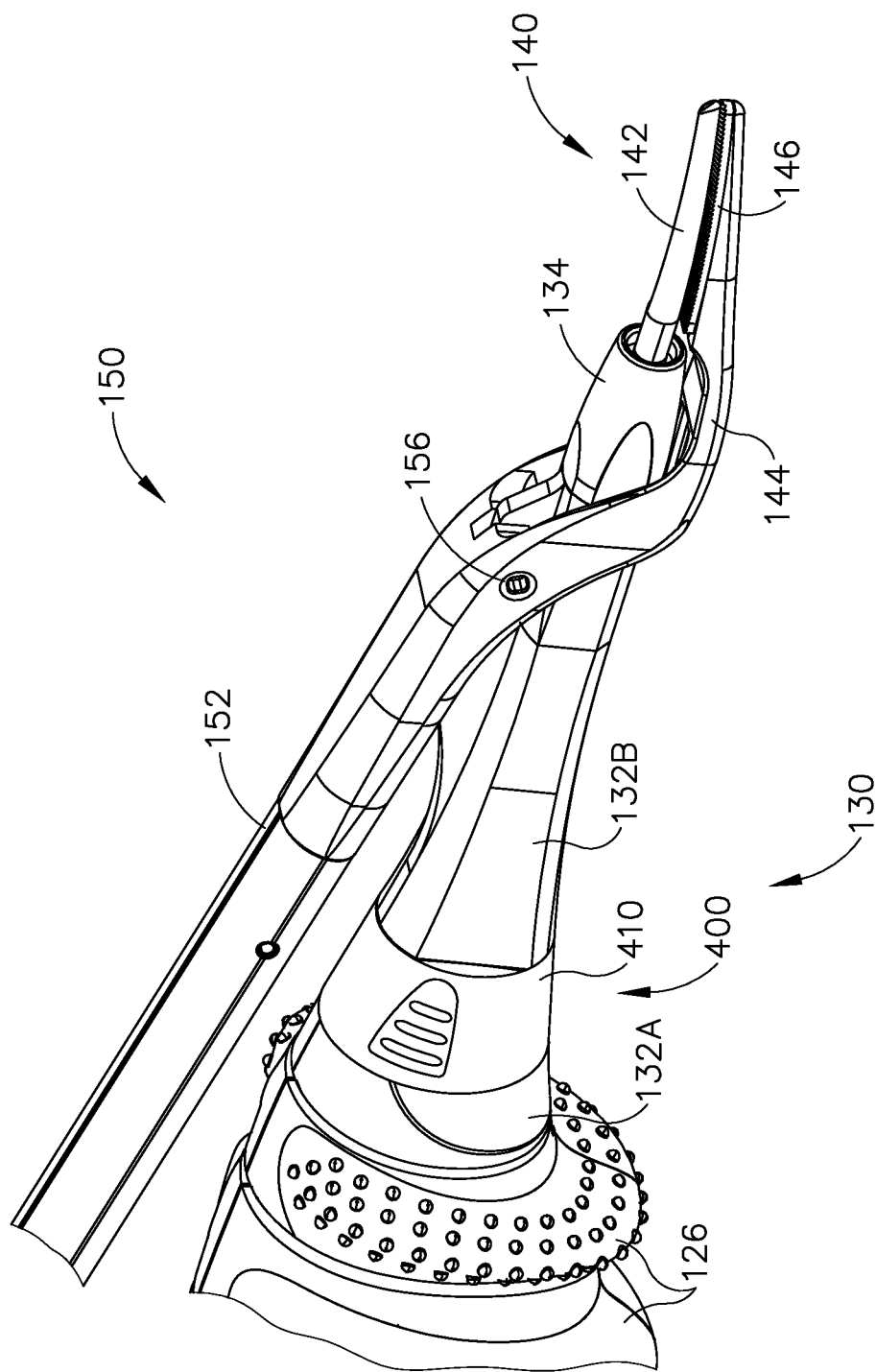
FIG. 23 depicts a perspective view of another variation of the instrument of FIG. 4 having an exemplary clamp arm rotation mechanism.

FIGS. 22A and 22B show yet another exemplary alternative ultrasonic blade rotation mechanism (360) that may be readily incorporated into instrument (100). Rotation mechanism (360) of the present example comprises an exemplary waveguide (362) and an exemplary pin (364). By way of example only, pin (364) may be formed of stainless steel coated with hard plastic. Of course, any other suitable material(s) may be used. Waveguide (362) is configured to operate substantially similar to waveguide (138) discussed above except for the differences discussed below. In particular, waveguide (362) communicates acoustic vibrations at ultrasonic frequencies to an ultrasonic blade (142) to thereby cut and/or seal tissue. Waveguide (362) of the present example is rotatably disposed within shaft assembly (130) such that waveguide (362) is rotatable relative to shaft assembly (130). Waveguide (362) is secured within shaft assembly (130) via pin (364), which passes through waveguide (362) and shaft assembly (130). Pin (364) is located at a position along the length of waveguide (362) corresponding to a node associated with resonant ultrasonic vibrations communicated through waveguide (362).

As shown in FIGS. 22A and 22B, pin (364) passes through an hourglass-shaped passageway (363) formed in waveguide (362). Thus it should be understood that waveguide (362) is operable to rotate relative to pin (364) as pin (364) translates within passageway (363). Pin (364) extends from shaft assembly (130) and a top of pin (364) presents a paddle (367). Paddle (367) may be engaged by a user to drive vertical translation of pin (364) along a path that is transverse to the longitudinal axis of waveguide (362). An interior surface of slot (363) of waveguide (362) presents an inwardly extending projection (368). Pin (364) has an inwardly directed recess (365) formed in an exterior of pin (364). Recess (365) of pin (364) is configured to receive projection (368) of slot (363) such that projection (368) engages pin (364) at recess (365). As will be discussed in more detail below, this engagement between recess (365) and projection (368) is configured to allow vertical translation of pin (364) (along a path that is transverse to the longitudinal axis of waveguide (362)) to cause rotation of waveguide (362) about the longitudinal axis of waveguide (362).

FIGS. 22A and 22B show the steps of rotating waveguide (362) via translation of pin (364). As shown in FIG. 22A, with pin (364) in a first vertical position, waveguide (362) and ultrasonic blade (142) are in a first rotational position. In this position, recess (365) is engaged with projection (365). A user may drive pin (364) along a path that is transverse to the longitudinal axis of waveguide (362), toward a second vertical position as shown in FIG. 22B. Because of the engagement between recess (365) of pin (364) and projection (368) of slot (363) of waveguide (362), the downward movement of pin (364) causes rotation of waveguide (362) and ultrasonic blade (142) about the longitudinal axis of waveguide (362). It should be understood that pin (364) may be actuated by the operator to rotate waveguide (362) and ultrasonic blade (142) at any time. For instance, the operator may actuate pin (364) by pressing paddle (367) when tissue is clamped within end effector (140). The curved configuration of ultrasonic blade (142) and the rotation of ultrasonic blade (142) together provide a distally advancing rolling engagement, such that an increased amount of compression force is applied between the distal end of ultrasonic blade (142) and clamp pad (146) as ultrasonic blade (142) is rotated. Thus, the compression force between the distal end of ultrasonic blade (142) and clamp pad (146) increases during the transition from the configuration shown in FIG. 22A to the configuration shown in FIG. 22B. This increase in distal compression may prevent formation of a tissue tag or cut a tissue tag at the distal end of end effector (140).

In some versions, paddle (367) or some other feature of pin (364) is configured and positioned such that shank (152) will drive pin (364) from the position shown in FIG. 22A to the position shown in FIG. 22B once clamp arm assembly (150) is pivoted within a certain range toward shaft assembly (130). By way of example only, pin (364) may be configured such that end effector (140) may reach a state of full closure, with ultrasonic blade (142) in full apposition with clamp pad (146), before shank (152) engages pin (364). Once clamp arm assembly (150) is pivoted further toward shaft assembly (130) after end effector (140) reaches this state, shank (152) drives pin (364) from the position shown in FIG. 22A to the position shown in FIG. 22B, thereby providing a rolling engagement between ultrasonic blade (142) and clamp pad (146). It should further be understood that waveguide (362) may be resiliently biased toward the first rotational position shown in FIG. 22A, such that waveguide (362) returns to the position shown in FIG. 22A as soon as the operator relaxes their grip on grip rings (124, 154). By way of example only, such resilient bias may be provided by a torsion spring or elastomeric bushing engaged with waveguide (362), a coil spring urging pin (364) to the position shown in FIG. 22A, and/or some other feature. It should also be understood that rotation mechanism (360) may include a selective locking feature that is operable to selectively lock waveguide (362) into the position shown in FIG. 22B. This may promote the use of the distal end of end effector (140) to make smaller "nibble" types of incisions in tissue. Various suitable features that may be used to provide such selective locking will be apparent to those of ordinary skill in the art in view of the teachings herein. As yet another merely illustrative variation, pin (364) may be configured to provide a cam feature similar to projection (368), such that slot (363) simply has an hourglass configuration. The cam feature of pin (364) may thus bear against the surface defining the hourglass shaped slot (363), to thereby provide rotation of waveguide (362) in response to pin (364) moving along a path that is transverse to the longitudinal axis of waveguide (362).

While rotation mechanism (360) is discussed as being incorporated into instrument (100) in the present example, it should be understood that rotation mechanism (360) may be readily incorporated into instrument (10).

III. Exemplary Ultrasonic Surgical Instruments with Clamp Arm Rotation Mechanisms As noted above, it may be desirable to provide some degree of relative rotation between an ultrasonic blade (42, 142) and a clamp arm (44, 144) in order to prevent or otherwise address the occurrence of tissue tags in tissue that is clamped between ultrasonic blade (42, 142) and clamp arm (44, 144). The various examples described above provide rotation of ultrasonic blade (42, 142) and waveguide (38, 138) relative to the rest of instrument (10, 100), to thereby provide rotation of ultrasonic blade (42, 142) relative to clamp arm (44, 144). By contrast, the examples described below provide rotation of clamp arm (44, 144) relative to the rest of instrument (10, 100), to thereby provide rotation of clamp arm (44, 144) relative to ultrasonic blade (42, 142). It should be understood that such rotation of clamp arm (44, 144) relative to ultrasonic blade (42, 142) may be just as effective at preventing or otherwise addressing the occurrence of tissue tags as the rotation of ultrasonic blade (42, 142) relative to clamp arm (144). It should be understood that the below examples may be viewed as variations of instruments (10, 100), such that various teachings below may be readily combined with various teachings above as will be apparent to those of ordinary skill in the art.

A. First Exemplary Clamp Arm Rotation Mechanism

FIGS. 23-25F show an exemplary clamp arm rotation mechanism (400) that may be readily incorporated into instrument (100). Outer sheath (132) of the present example comprises a first portion (132A) and a second portion (132B). First portion (132A) and second portion (132B) are rotatably coupled together such that second portion (132B) is rotatable relative to first portion (132A). Clamp arm assembly (150) is pivotally coupled with second portion (132B) of outer sheath (132) via pin (156). Thus it should be understood that clamp arm assembly (150), including clamp arm (144), is rotatable relative to first portion (132A) of outer sheath (132). In particular, clamp arm assembly (150) and second portion (132B) are together rotatable relative to first portion (132A) and the remainder of instrument (100), about the longitudinal axis of waveguide (138). Rotation mechanism (400) of the present example comprises a longitudinally translatable locking member (410). As will be discussed in more detail below, locking member (410) is configured to selectively engage a plurality of tabs (402A, 402B, 402C, 402D) extending outwardly from an exterior surface of second portion (132B) to thereby selectively prevent and/or allow rotation of second portion (132B) and clamp arm assembly (150) relative to first portion (132A) and the remainder of instrument (100). Locking member (410) is keyed to second portion (132B) such that locking member translates relative to second portion (132B) yet locking member (410) rotates concomitantly with second portion (132B).

Figure 24A:
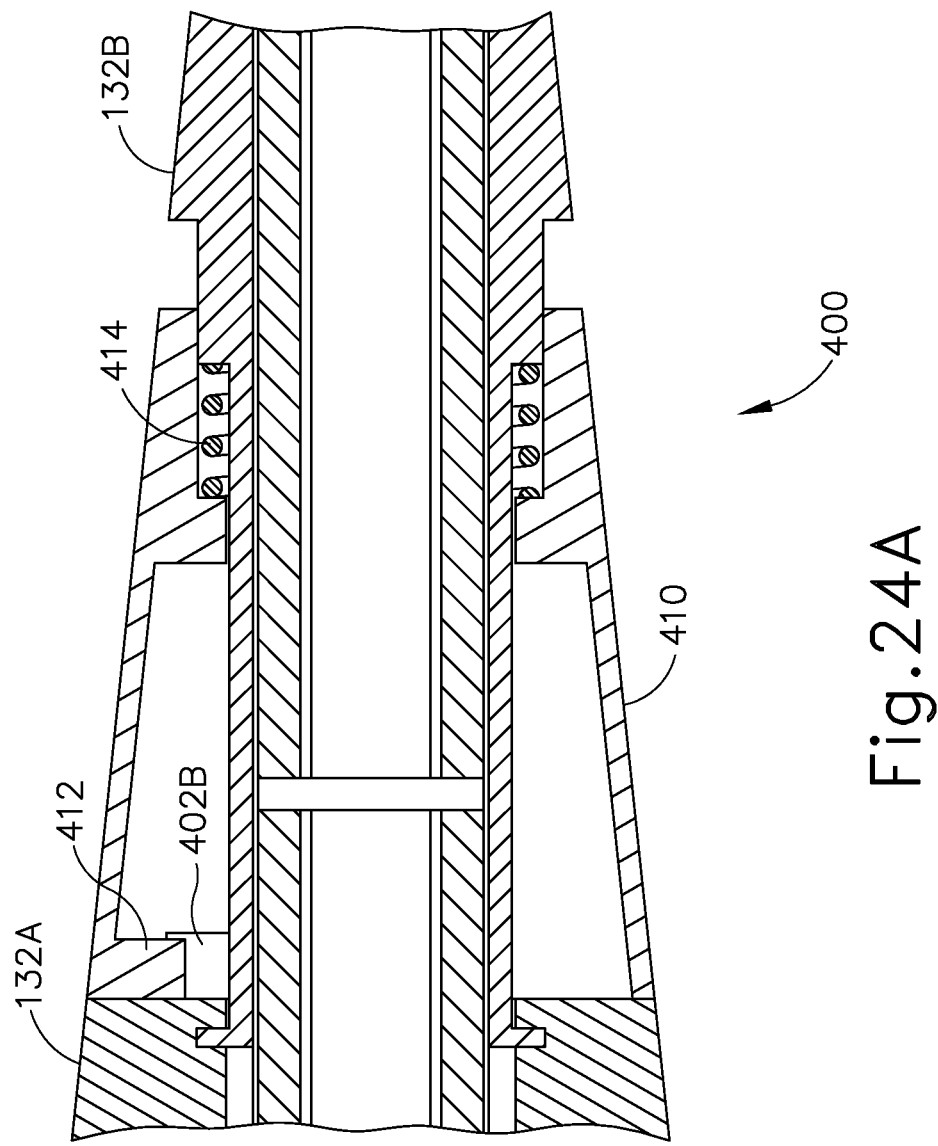
FIG. 24A depicts a cross-sectional view of a locking member of the clamp arm rotation mechanism of FIG. 23 in a first longitudinal position.
Figure 24B:
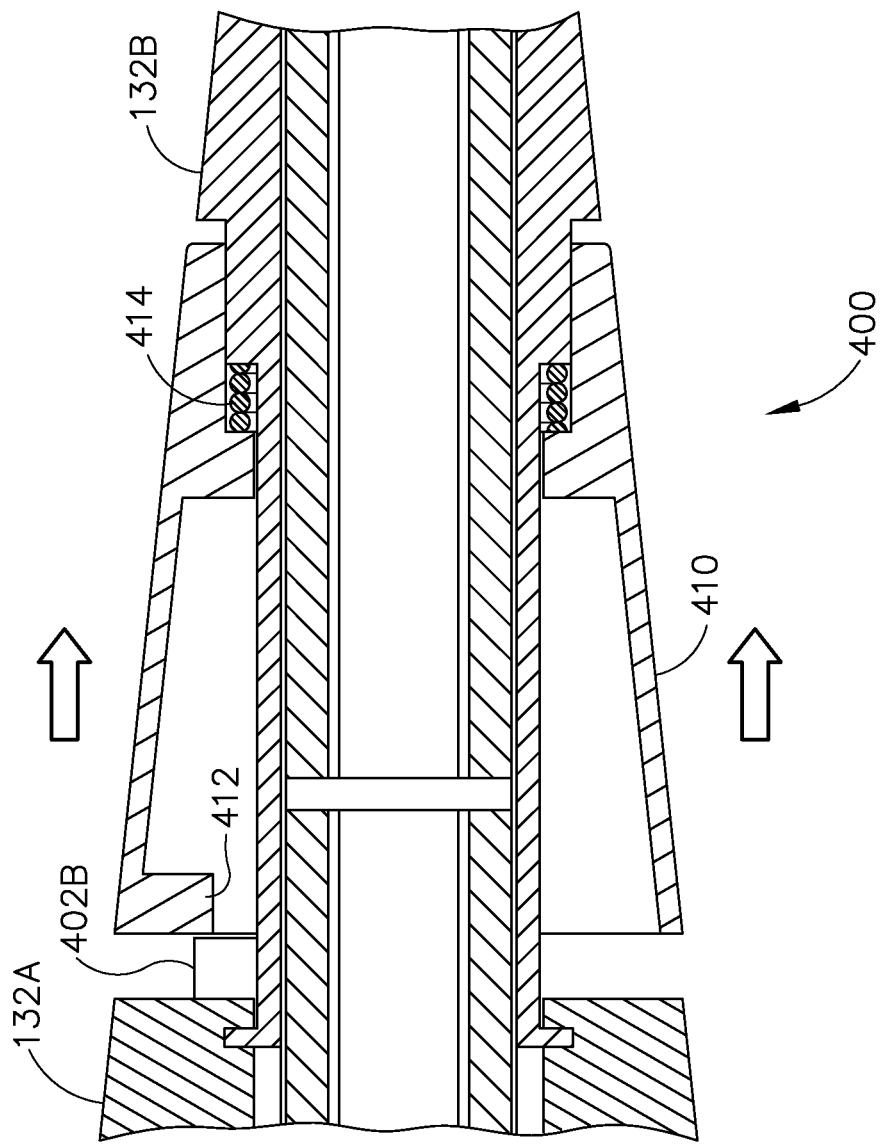
FIG. 24B depicts a cross-sectional view of the locking member of FIG. 24A moved into a second longitudinal position.

FIGS. 24A and 24B show the steps of selectively locking and unlocking second portion (132B) via locking member (410) of rotation mechanism (400) to thereby prevent and/or allow rotation of second portion (132B) and clamp arm assembly (150). Plurality of tabs (402A, 402B, 402C, 402D) extend outwardly from the exterior surface of second portion (132B) and define gaps in between respective tabs (402A, 402B, 402C, 402D). In a first longitudinal position, an inwardly extending tab (412) of locking member (410) is positioned within a particular gap defined by a particular pair of plurality of tabs (402A, 402B, 402C, 402D) as shown in FIG. 24A. In this position, because tab (412) of locking member (410) is within the particular gap defined by tabs (402A, 402B, 402C, 402D), second portion (132B) of outer sheath (132) and clamp arm assembly (150) may not be rotated relative to first portion (132A). Also as shown in FIG. 24A, locking member (410) is biased proximally toward this first longitudinal position via a coil spring (414) bearing against a distal surface of locking member (410) and a proximal surface of second portion (132B). Of course, a coil spring (414) is just an example and any other suitable type of resilient feature may be used.

A user may translate locking member (410) longitudinally distally into a second longitudinal position such that tab (412) is no longer within the particular gap defined by tabs (402A, 402B, 402C, 402D) and such that tab (412) no longer engages tabs (402A, 402B, 402C, 402D). FIG. 24B shows locking member (410) in such a second longitudinal position. In this second longitudinal position, because tab (412) no longer engages tabs (402A, 402B, 402C, 402D), second portion (132B) of outer sheath (132) and clamp arm assembly (150) may be rotated relative to first portion (132A). Once the operator has achieved a desired angular orientation of second portion (132B) and clamp arm assembly (150) relative to first portion (132A) and the remainder of instrument (100), the operator may release locking member (410). Upon the release of locking member (410), coil spring (414) will drive locking member (410) back to the proximal position shown in FIG. 24A, such that tab (412) will be located in a gap defined by tabs (402A, 402B, 402C, 402D). Tabs (412, 402A, 402B, 402C, 402D) will thus effectively lock the selected angular orientation of second portion (132B) and clamp arm assembly (150) relative to first portion (132A) and the remainder of instrument (100). It should be understood that tabs (412, 402A, 402B, 402C, 402D) are just one merely illustrative example and that various other kinds of features may be used, including but not limited to detent features, clamping features, etc. Furthermore, while tabs (412, 402A, 402B, 402C, 402D) provide a limited number of angular orientations, other versions may provide an infinite adjustability of the angular orientation within a 360° range or lesser angular range.

Figure 25A:
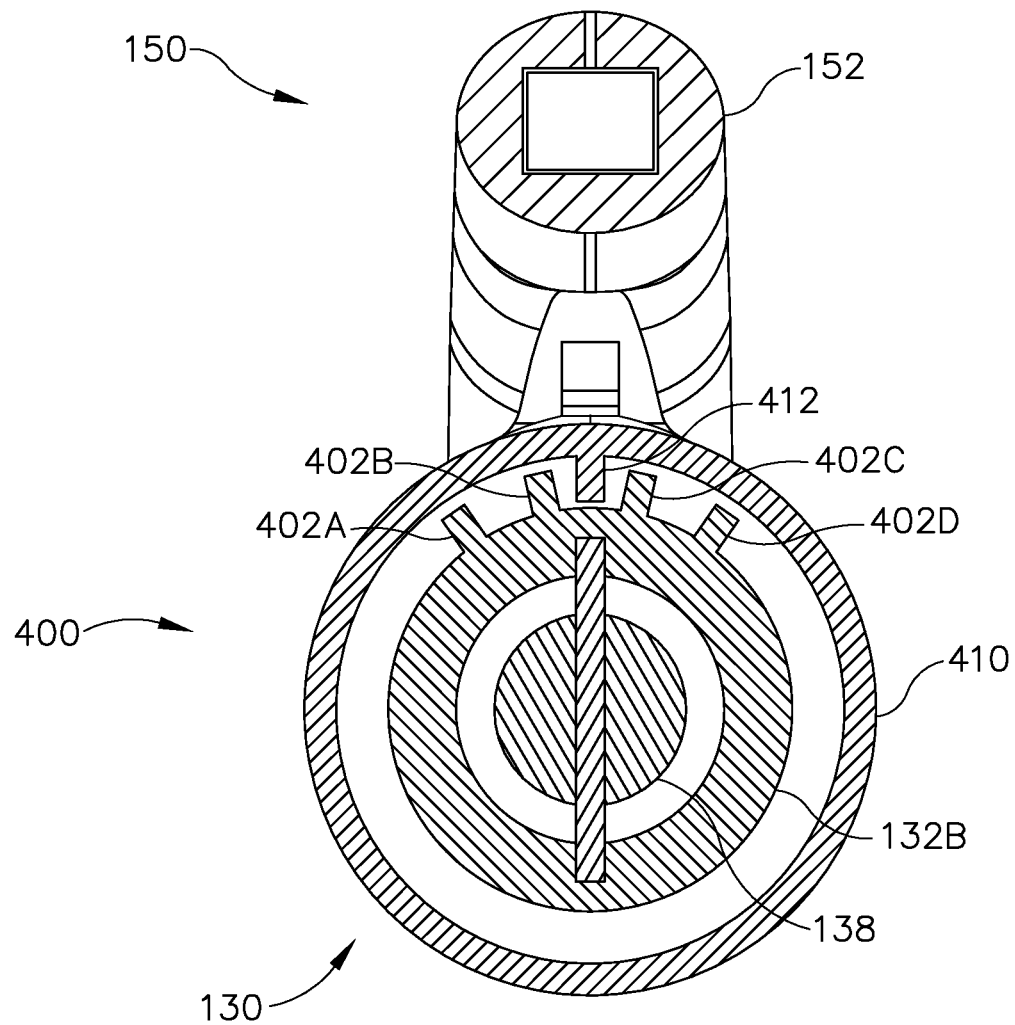
FIG. 25A depicts a cross-sectional view of clamp arm rotation mechanism of the instrument of FIG. 23, with the clamp arm in a first rotational position.
Figure 25B:
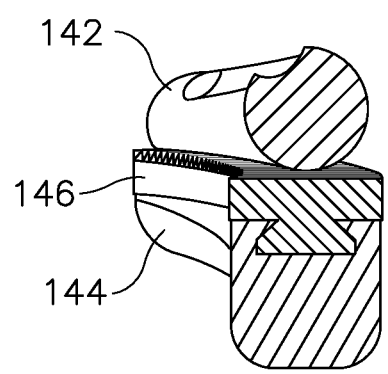
FIG. 25B depicts a cross-sectional view of the ultrasonic blade and the clamp arm of the instrument of FIG. 23, with the clamp arm in a first rotational position.
Figure 25C:
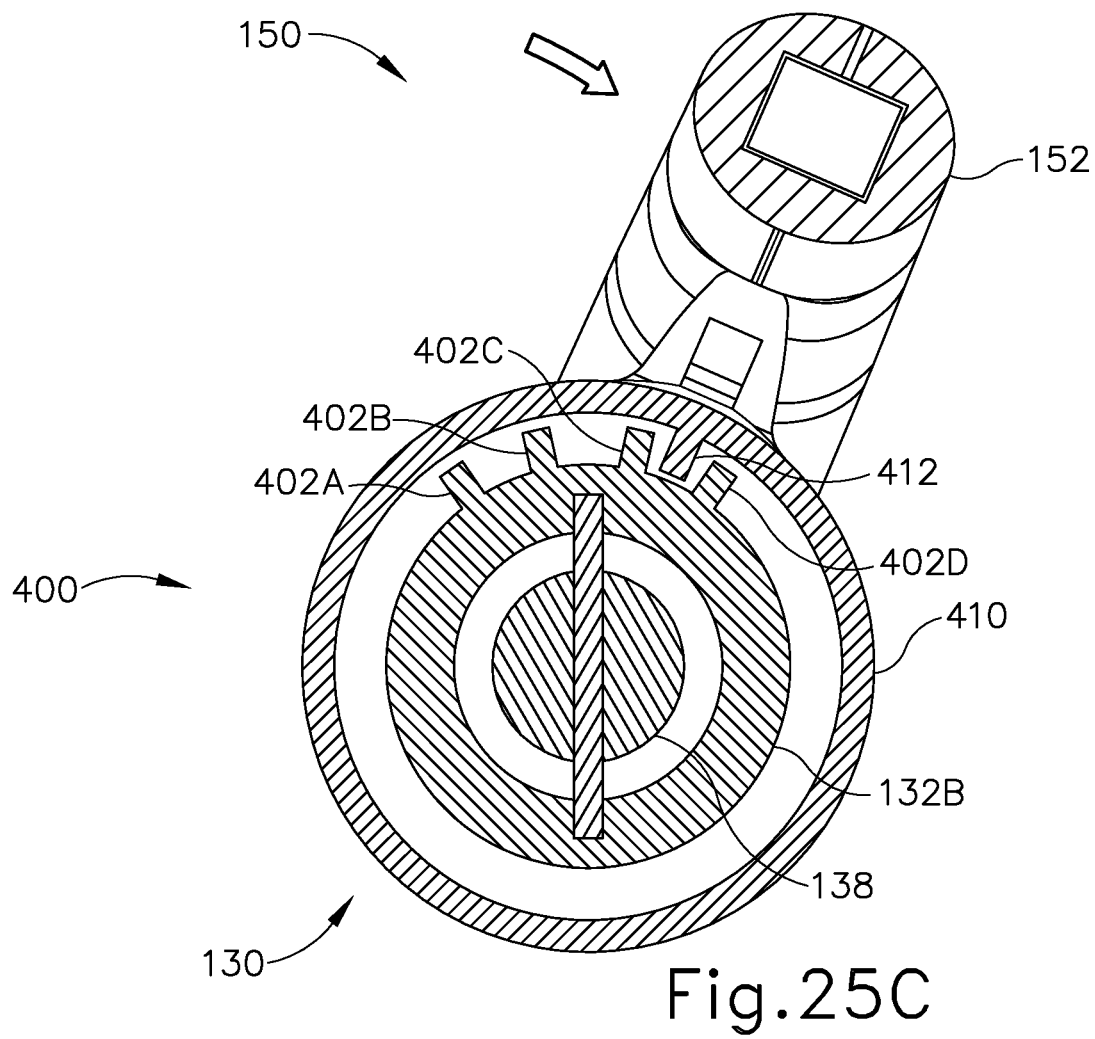
FIG. 25C depicts a cross-sectional view of clamp arm rotation mechanism of FIG. 25A, with the clamp arm moved into a second rotational position.
Figure 25D:
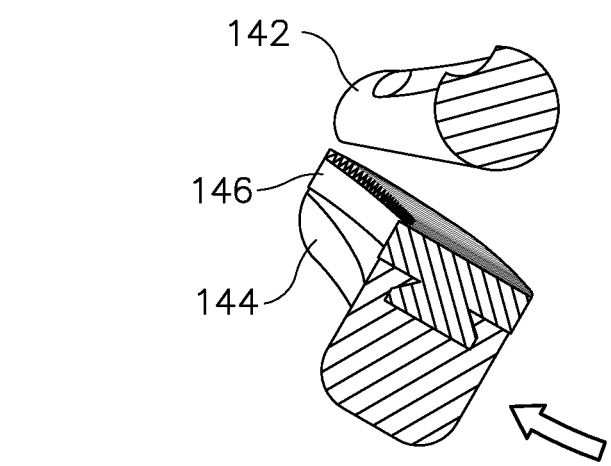
FIG. 25D depicts a cross-sectional view of the ultrasonic blade and the clamp arm of FIG. 25B, with the clamp arm moved into the second rotational position.
Figure 25E:
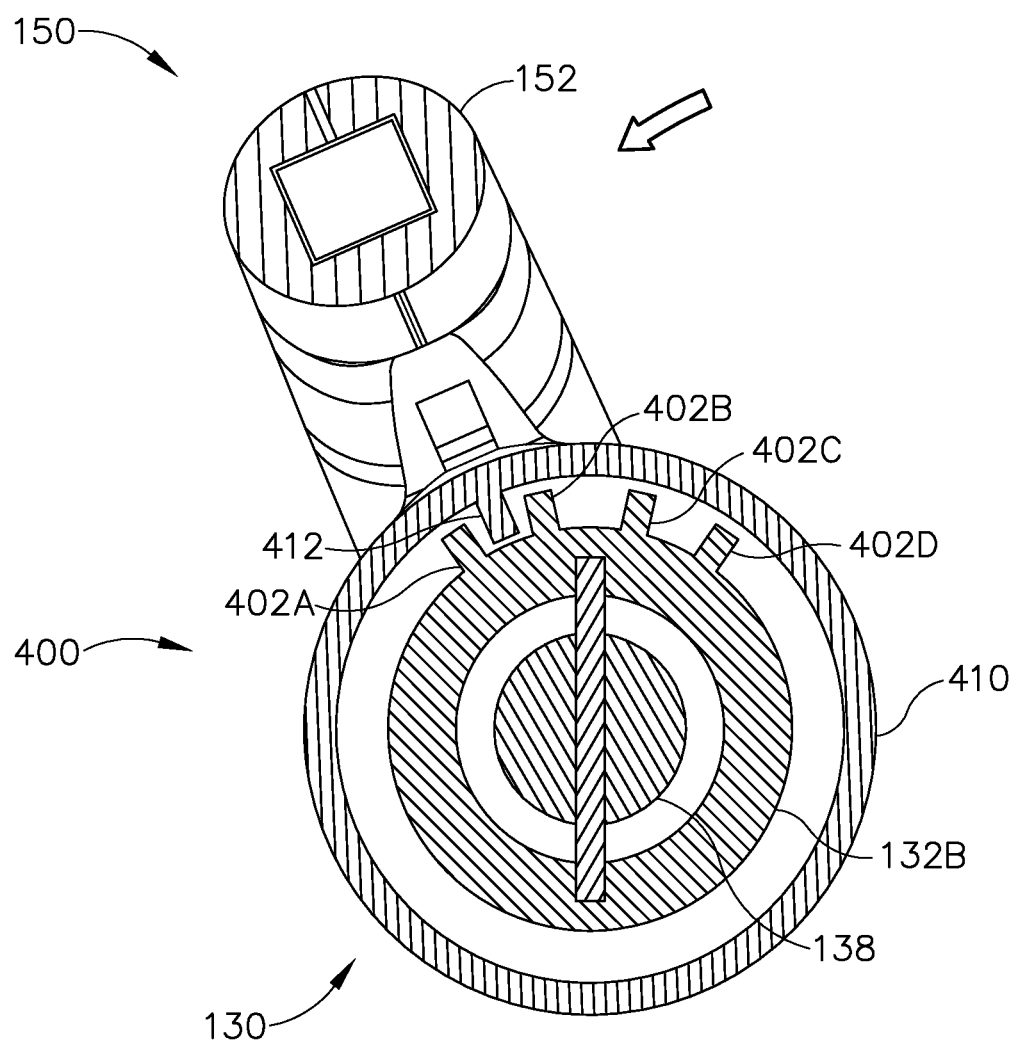
FIG. 25E depicts a cross-sectional view of clamp arm rotation mechanism of FIG. 25A, with the clamp arm moved into a third rotational position.
Figure 25F:
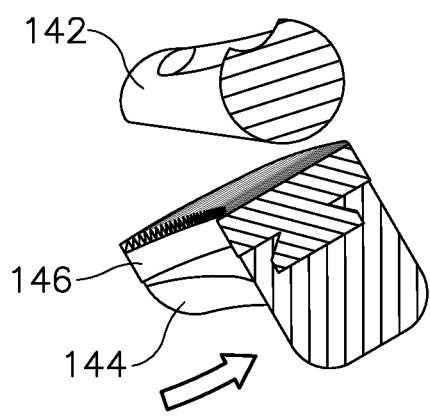
FIG. 25F depicts a cross-sectional view of the ultrasonic blade and the clamp arm of FIG. 25B, with the clamp arm moved into the third rotational position.
Figure 26:
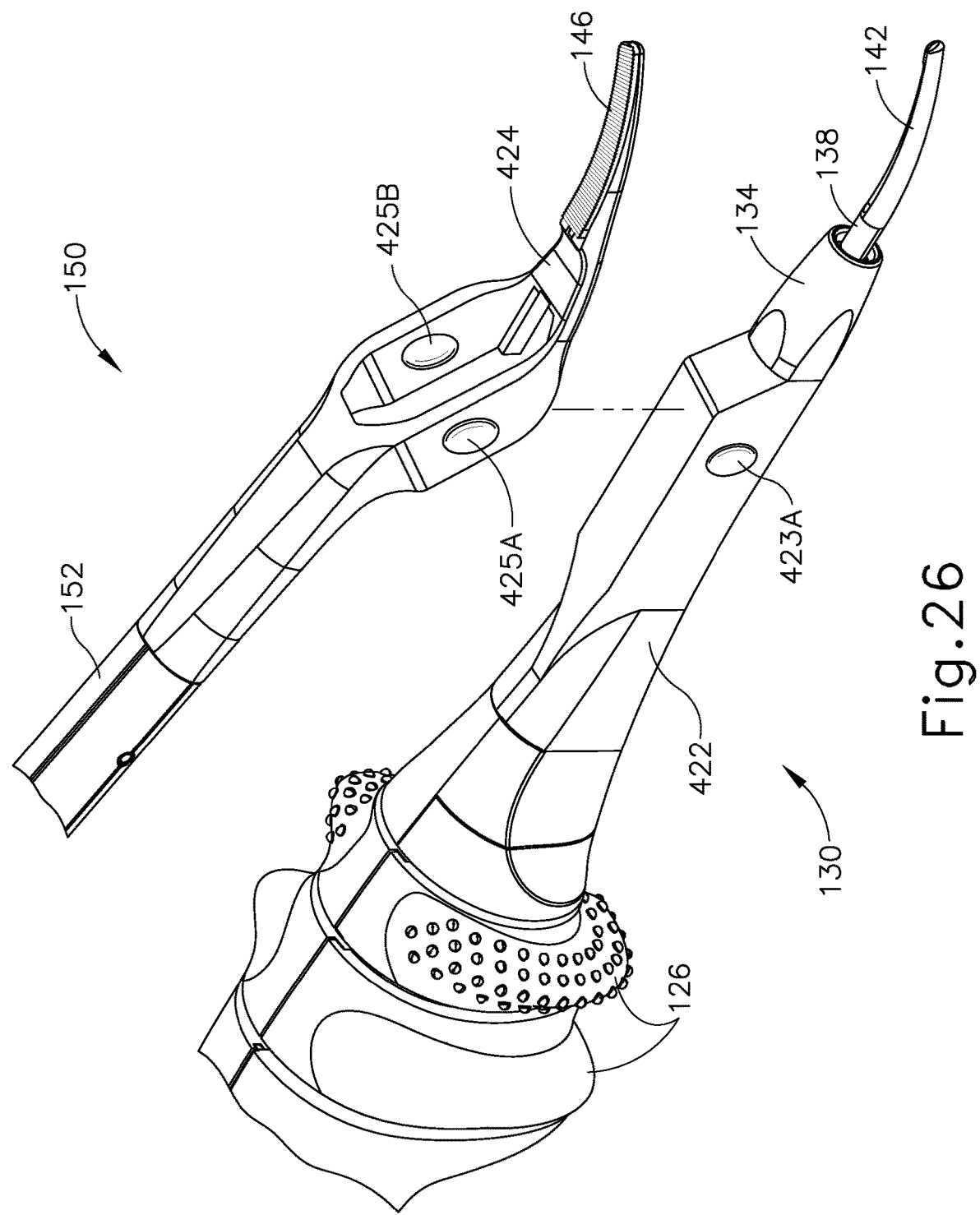
FIG. 26 depicts a partial exploded perspective view of another variation of the instrument of FIG. 4 having an exemplary alternative clamp arm rotation mechanism.

FIGS. 25A, 25C, and 25E show various rotational positions of second portion (132B) and clamp arm assembly (150); while FIGS. 25B, 25D, and 25F show the corresponding rotational positions of clamp arm (144) relative to ultrasonic blade (142). FIGS. 25A and 25B show second portion (132B) or outer sheath (132), clamp arm assembly (150), and clamp arm (144) in a first rotational position. In this first rotational position, tab (412) of locking member (410) is disposed within a gap defined by tabs (402B, 402C) of outer sheath (132). Clamp arm (144) is parallel to ultrasonic blade (142) such that the entire length of clamp pad (146) engages ultrasonic blade (142) as clamp arm (144) is closed toward ultrasonic blade (142).

FIGS. 25C and 25D show second portion (132B) or outer sheath (132), clamp arm assembly (150), and clamp arm (144) in a second rotational position. In this second rotational position, tab (412) of locking member (410) is disposed within a gap defined by tabs (402C, 402D) of outer sheath (132). Clamp arm (144) is angled obliquely relative to ultrasonic blade (142) such that the distal end of clamp pad (146) engages ultrasonic blade (142) first as clamp arm (144) is closed toward ultrasonic blade (142). In other words, the second rotational position is associated with a tip-loaded configuration for end effector (140). Such a tip-loaded configuration may be used to prevent tissue tags that might otherwise be left by end effector (140) if end effector (140) were actuated with ultrasonic blade (142) oriented substantially parallel to clamp pad (146). In addition or in the alternative, such a tip-loaded configuration may promote the use of the distal end of end effector (140) to make smaller "nibble" types of incisions in tissue. In some instances, after the distal end of clamp pad (146) engages ultrasonic blade (142) during closure of clamp arm (144), clamp arm (144) may move further through a second range of closure motion whereby the rest of the length of clamp pad (146) engages ultrasonic blade (142). For instance, clamp arm (144) and clamp pad (146) may provide some degree of deformability.

FIGS. 25E and 25F show second portion (132B) or outer sheath (132), clamp arm assembly (150), and clamp arm (144) in a third rotational position. In this third rotational position, tab (412) of locking member (410) is disposed within a gap defined by tabs (402A, 402B) of outer sheath (132). Clamp arm (144) is angled obliquely relative to ultrasonic blade (142) such that the proximal end of clamp pad (146) engages ultrasonic blade (142) first as clamp arm (144) is closed toward ultrasonic blade (142). In other words, the second rotational position is associated with a proximal-loaded configuration for end effector (140). Such a proximal-loaded configuration may be used to prevent tissue tags that might otherwise be left by end effector (140) if end effector (140) were actuated with ultrasonic blade (142) oriented substantially parallel to clamp pad (146). In some instances, after the proximal end of clamp pad (146) engages ultrasonic blade (142) during closure of clamp arm (144), clamp arm (144) may move further through a second range of closure motion whereby the rest of the length of clamp pad (146) engages ultrasonic blade (142). For instance, clamp arm (144) and clamp pad (146) may provide some degree of deformability.

It should be understood that the gaps defined by tabs (402A, 402B, 402C, 402D) may be arranged in an angular array about the exterior surface of second portion (132B) of outer sheath (132) such that any angular distance exists between each gap. For instance, the gaps may be at an angular distance of 45° from one another and/or any other suitable angular distance. While rotation mechanism (400) is discussed as being incorporated into instrument (100) in the present example, it should be understood that rotation mechanism (400) may be readily incorporated into instrument (10).

B. Second Exemplary Clamp Arm Rotation Mechanism

FIGS. 26-28C show an exemplary alternative clamp arm rotation mechanism (420) that may be readily incorporated into instrument (100). Rotation mechanism (420) of the present example comprises an exemplary alternative outer sheath (422) and an exemplary alternative clamp arm (424). Outer sheath (422) of the present example is configured to operate substantially similar to outer sheath (132) discussed above except for the differences discussed below. In particular, outer sheath (422) extends distally from body (122) of handle assembly (120). Clamp arm (424) is pivotably coupled with outer sheath (422). Clamp arm (424) of the present example is configured to operate substantially similar to clamp arm (44) discussed above except for the differences discussed below. In particular, clamp arm (424) is an integral feature of clamp arm assembly (150) and is pivotable toward and away from ultrasonic blade (142) based on pivoting of thumb grip ring (154) toward and away from body (122) of handle assembly (120). Clamp pad (146) is integrally secured to clamp arm (424).

Outer sheath (422) presents a pair of semi-spherical projections (423A, 423B) disposed on opposite sides of outer sheath (424). Clamp arm (424) comprises a pair of semi-spherical recesses (425A, 425B). In some other versions, semi-spherical recesses (425A, 425B) are substituted with openings. Semi-spherical recesses (425A, 425B) are configured to receive and engage semi-spherical projections (423A, 423B) of outer sheath (422). Clamp arm (424) may be configured to provide an inward bias to semi-spherical recesses (425A, 425B) such that semi-spherical recesses (425A, 425B) retain clamp arm (424) on semi-spherical projections (423A, 423B) during operation of instrument (100).

Figure 27A:
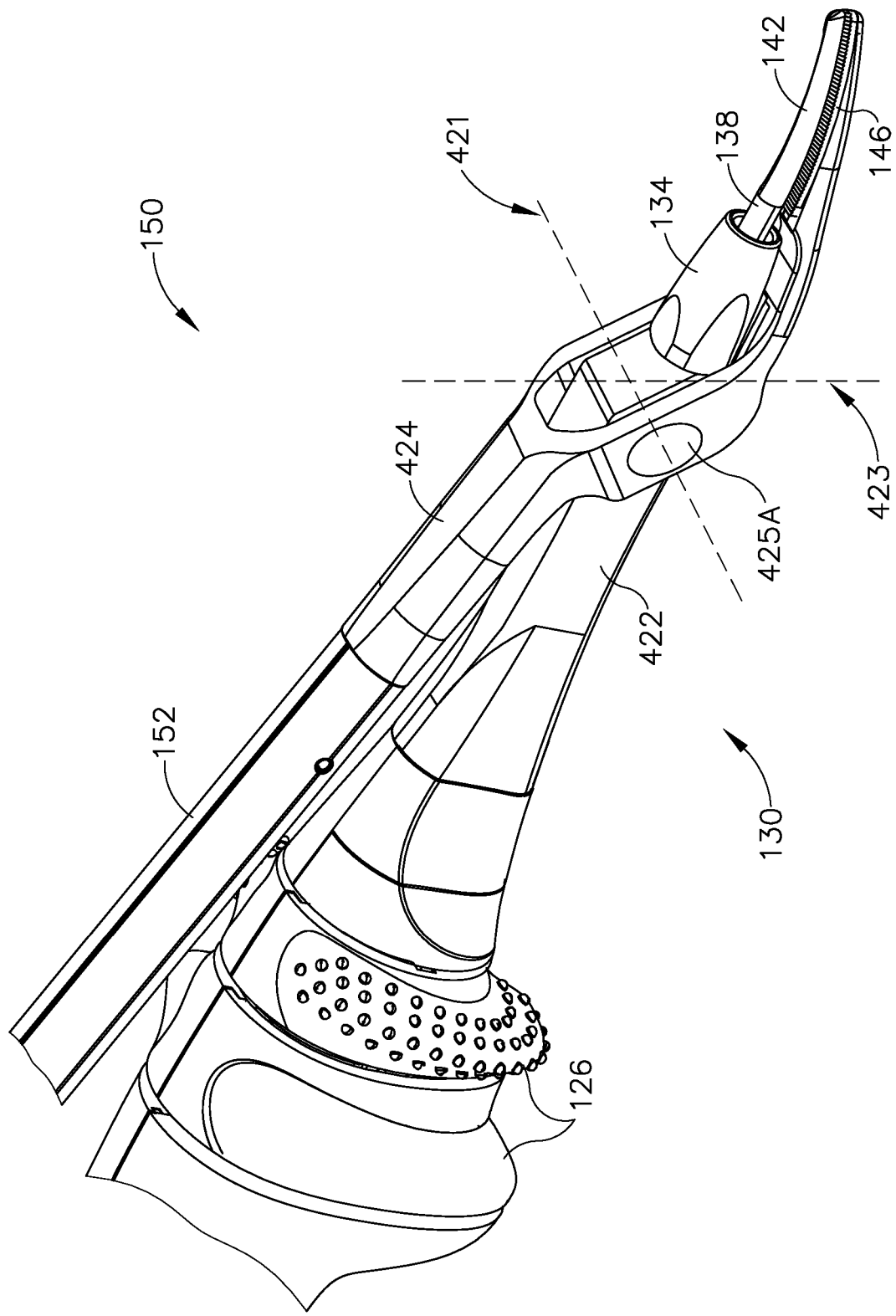
FIG. 27A depicts a perspective view of the instrument of FIG. 26 with the instrument in a closed configuration.
Figure 27B:
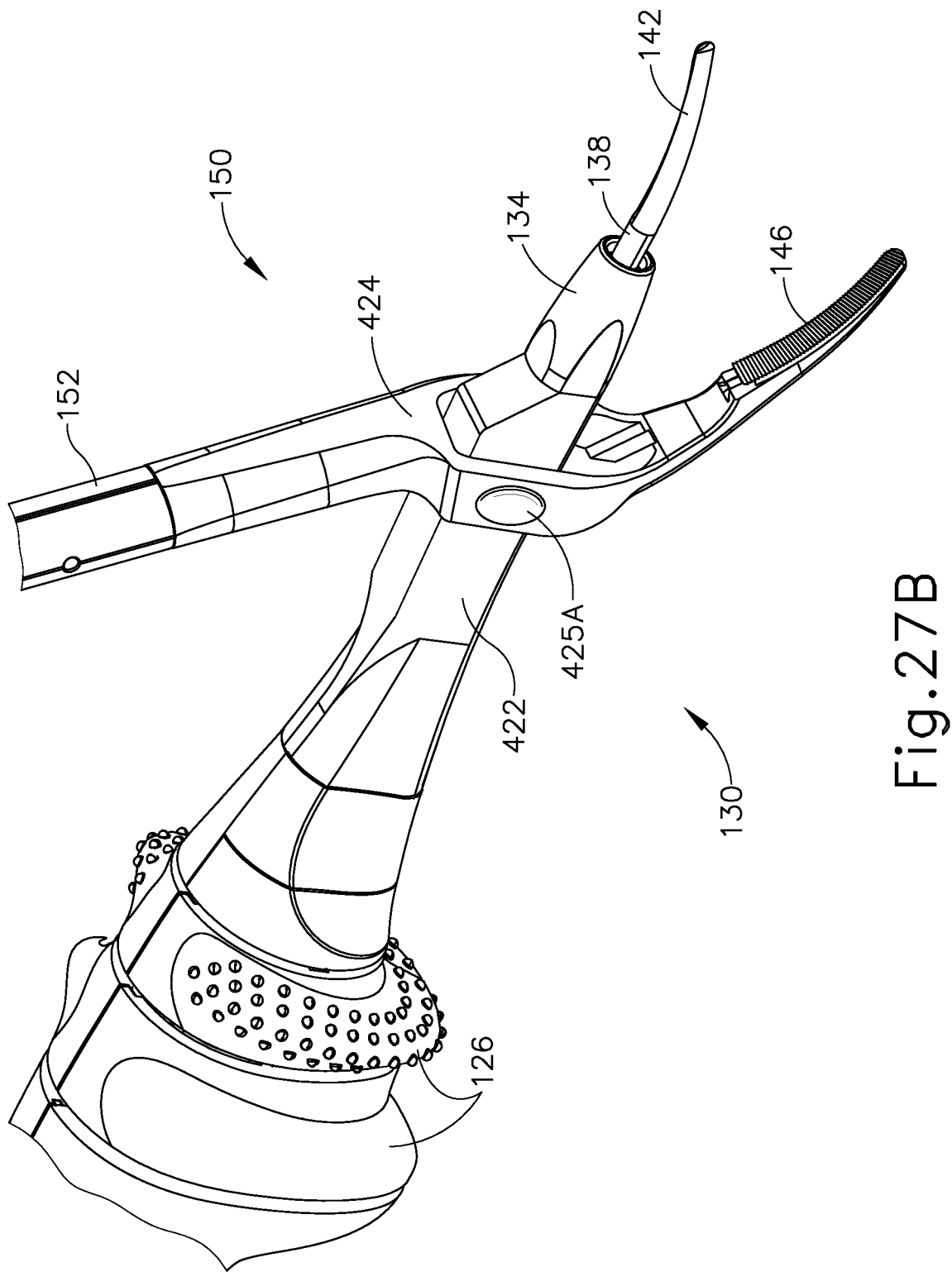
FIG. 27B depicts a perspective view of the instrument of FIG. 26 with the instrument moved into an open configuration.
Figure 28A:
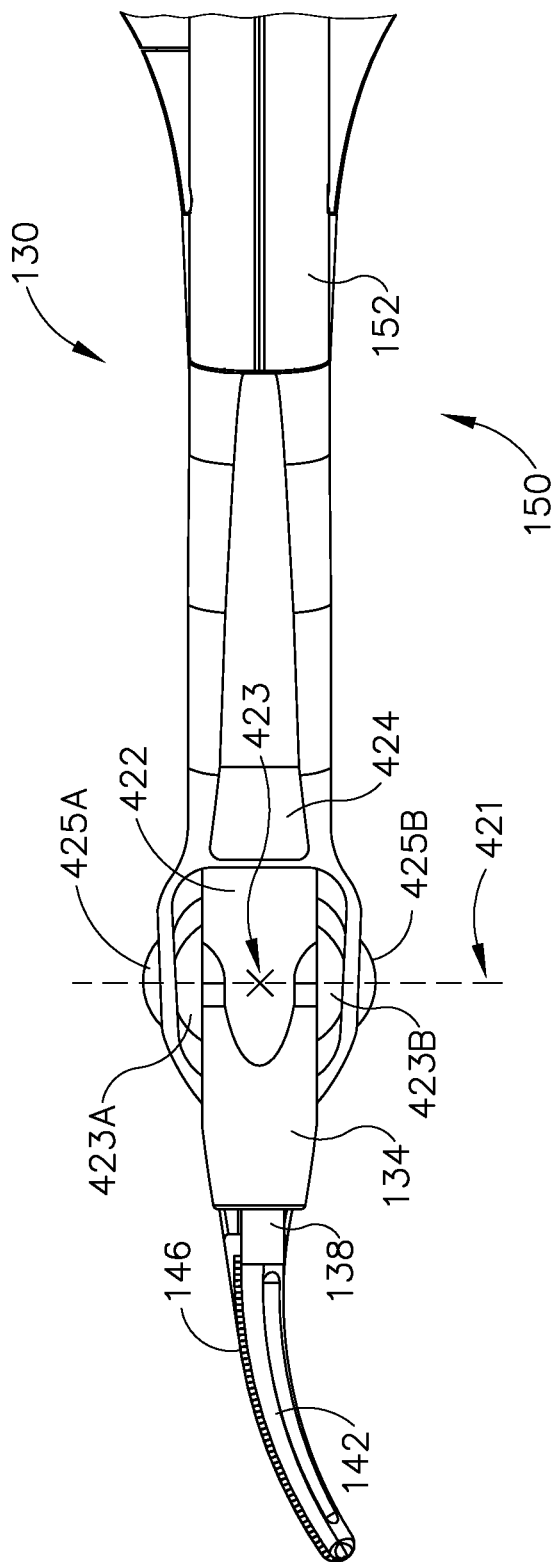
FIG. 28A depicts a top plan view of the instrument of FIG. 26 with the clamp arm in a first lateral rotational position.
Figure 28B:
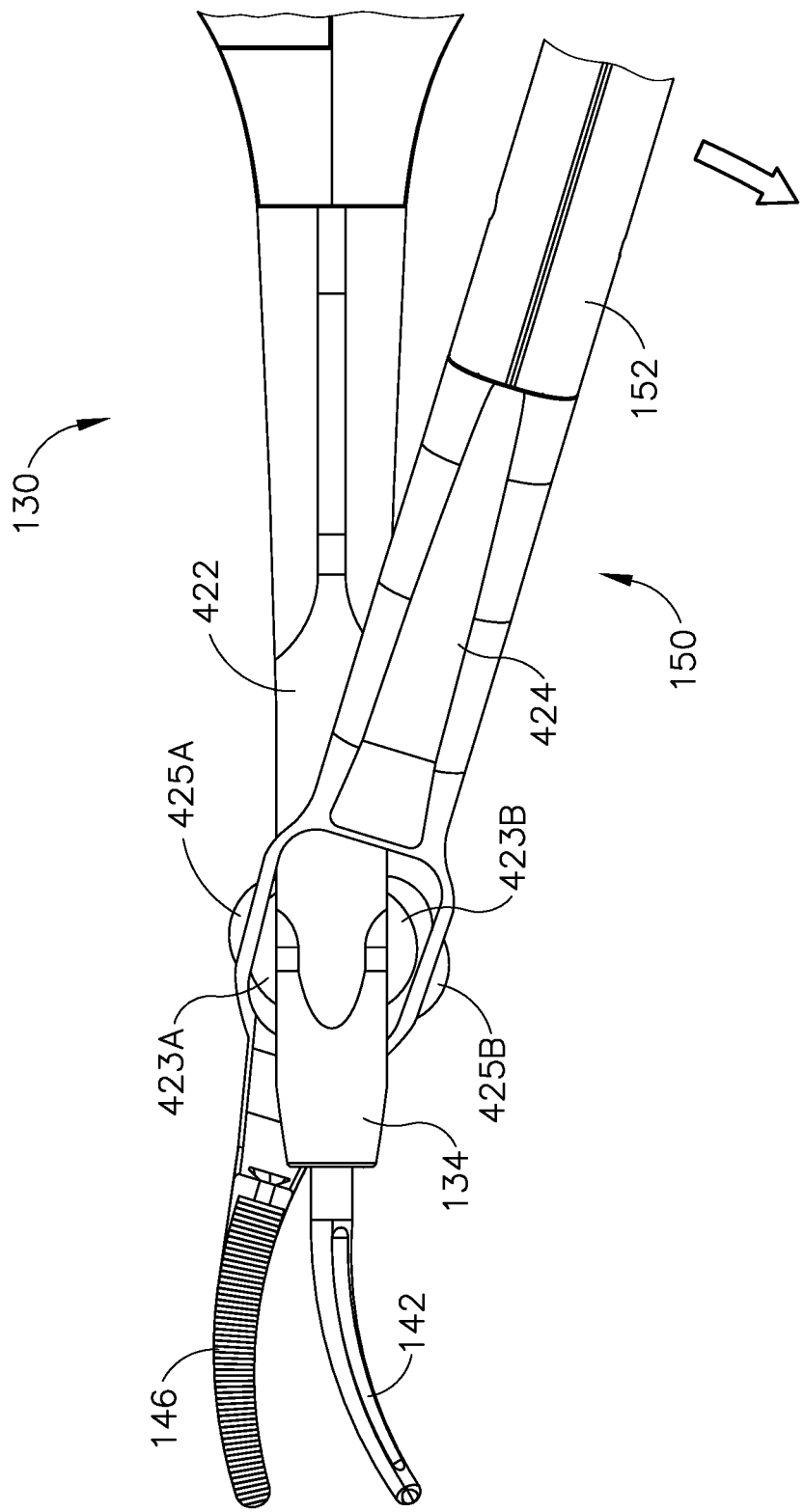
FIG. 28B depicts a top plan view of the instrument of FIG. 26 with the clamp arm moved into a second lateral rotational position.
Figure 28C:
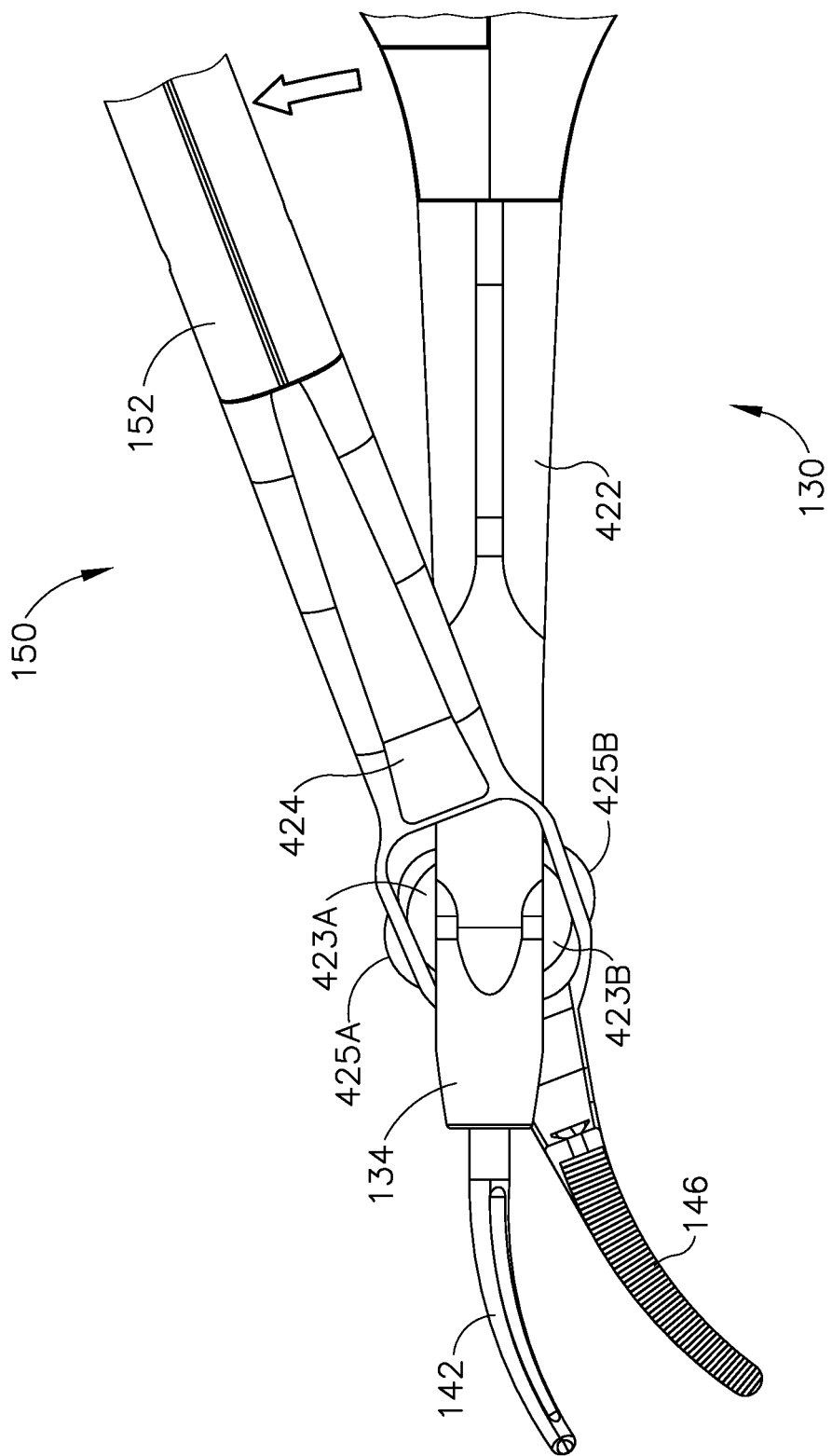
FIG. 28C depicts a top plan view of the instrument of FIG. 26 with the clamp arm moved into a third lateral rotational position.
Figure 29:
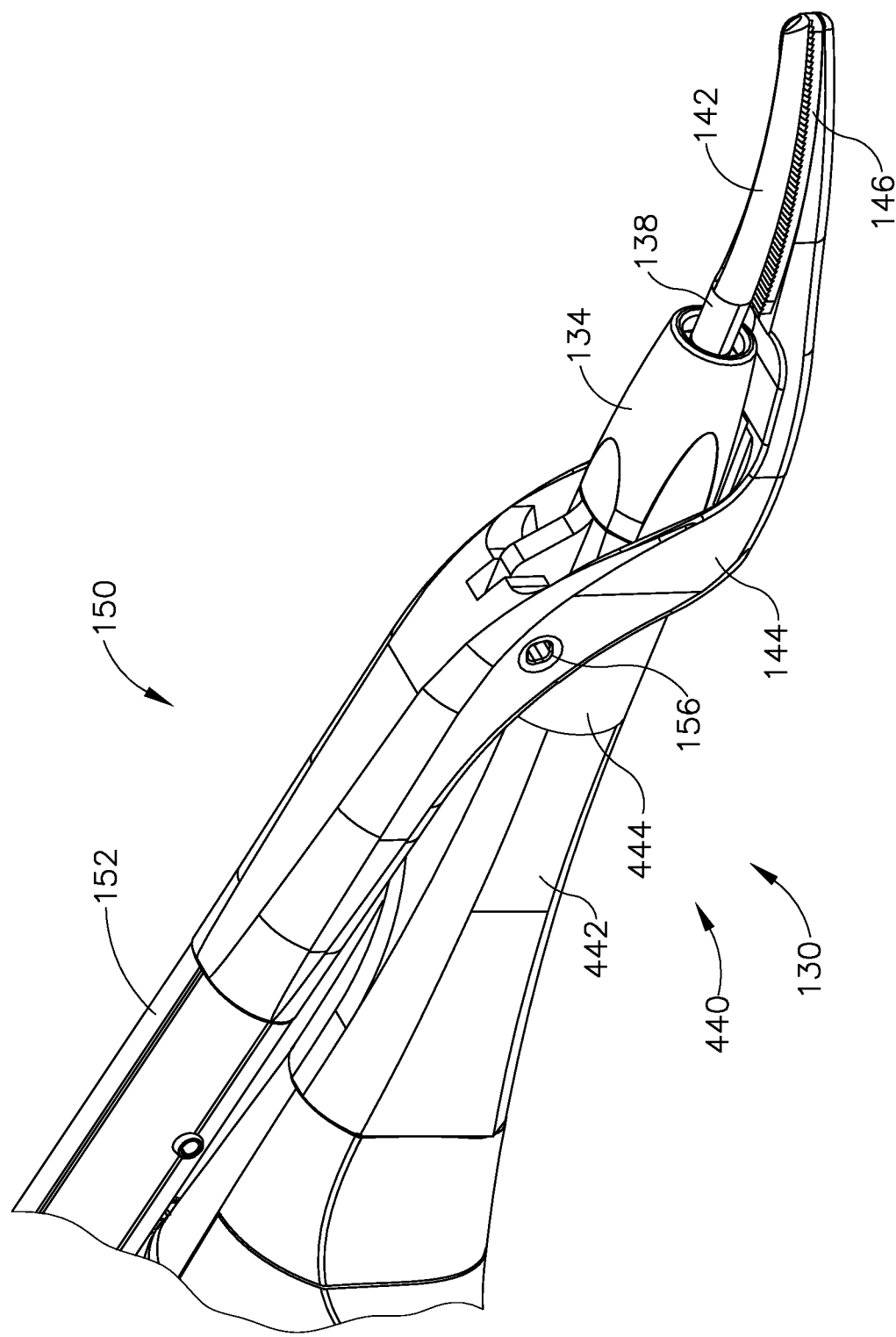
FIG. 29 depicts a perspective view of another variation of the instrument of FIG. 4 having another exemplary alternative clamp arm rotation mechanism.

The configurations of semi-spherical projections (423A, 423B) and semi-spherical recesses (425A, 425B) is configured to allow clamp arm assembly (150), including clamp arm (424) to rotate about multiple axes relative to outer sheath (422), waveguide (138), and ultrasonic blade (142). For instance, the engagement between semi-spherical projections (423A, 423B) and semi-spherical recesses (425A, 425B) allows clamp arm (424) to move toward and away from ultrasonic blade (142) about a first pivot axis (421) as shown in FIGS. 27A and 27B. Additionally, the engagement between semi-spherical projections (423A, 423B) and semi-spherical recesses (425A, 425B) allows clamp arm (424) to move laterally relative to ultrasonic blade (142) about a second pivot axis (423) as shown in FIGS. 28A-28C. In use, after the operator has clamped tissue between clamp arm (424) and ultrasonic blade (142) by driving clamp arm assembly (150) about first pivot axis (421) as shown in FIGS. 27A and 28A, and after the operator has activated ultrasonic blade (142) to vibrate ultrasonically to sever and seal the clamped tissue, the operator may then drive clamp arm assembly (150) in a lateral rocking motion about second pivot axis (423) as shown in FIGS. 28B-28C while holding clamp arm (424) in a clamped position about first pivot axis (421). This lateral movement of clamp arm (424) relative to ultrasonic blade (142) may prevent or cut tissue tags that might otherwise be present in the absence of such lateral movement. In some versions, one or more resilient members (e.g., wave springs, etc.) resiliently bias clamp arm (424) to the laterally centered position about second pivot axis (423) as shown in FIG. 28A; while still permitting clamp arm (424) to be deflected laterally about second pivot axis (423) as shown in FIGS. 28B-28C.

It should be understood that the lateral movement depicted in FIGS. 28B-28C may be exaggerated, such that the actual lateral movement of clamp arm (424) relative to ultrasonic blade (142) about second pivot axis (423) may not be nearly as pronounced as it is in FIGS. 28B-28C. It should also be understood that outer sheath (422) and/or one or more other features of instrument (100) may include a cam feature that drives clamp arm (424) laterally in the direction shown in FIG. 28B and/or in the direction shown in FIG. 28C during closure of clamp arm (424). For instance, such a cam feature may permit clamp arm (424) to first reach a state of parallel closure as shown in FIGS. 27A and 28A after clamp arm assembly (150) is pivoted a first range of motion about first pivot axis (421). Then if clamp arm assembly (150) is further pivoted through a second range of motion about first pivot axis (421), after clamp arm (424) has reached the state of parallel closure as shown in FIGS. 27A and 28A, the cam feature may drive clamp arm (424) laterally about the second pivot axis (423) in the direction shown in FIG. 28B and/or in the direction shown in FIG. 28C. It should be understood that clamp arm (424) and/or shank (152) may provide some degree of deformability to enable clamp arm assembly (150) to be driven through the second range of motion after clamp arm (424) has reached the state of parallel closure as shown in FIGS. 27A and 28A.

C. Third Exemplary Clamp Arm Rotation Mechanism

FIGS. 29-31C show another exemplary alternative clamp arm rotation mechanism (440) that may be readily incorporated into instrument (100). Rotation mechanism (440) of the present example comprises an exemplary alternative outer sheath (442). Outer sheath (442) of the present example is configured to operate substantially similar to outer sheath (132) discussed above except for the differences discussed below. In particular, outer sheath (442) extends distally from body (122) of handle assembly (120). Outer sheath (442) of the present example comprises a rotatable member (444). Clamp arm (144) is pivotably coupled with a rotatable member (444) of outer sheath (442) via pin (156).

Figure 30:
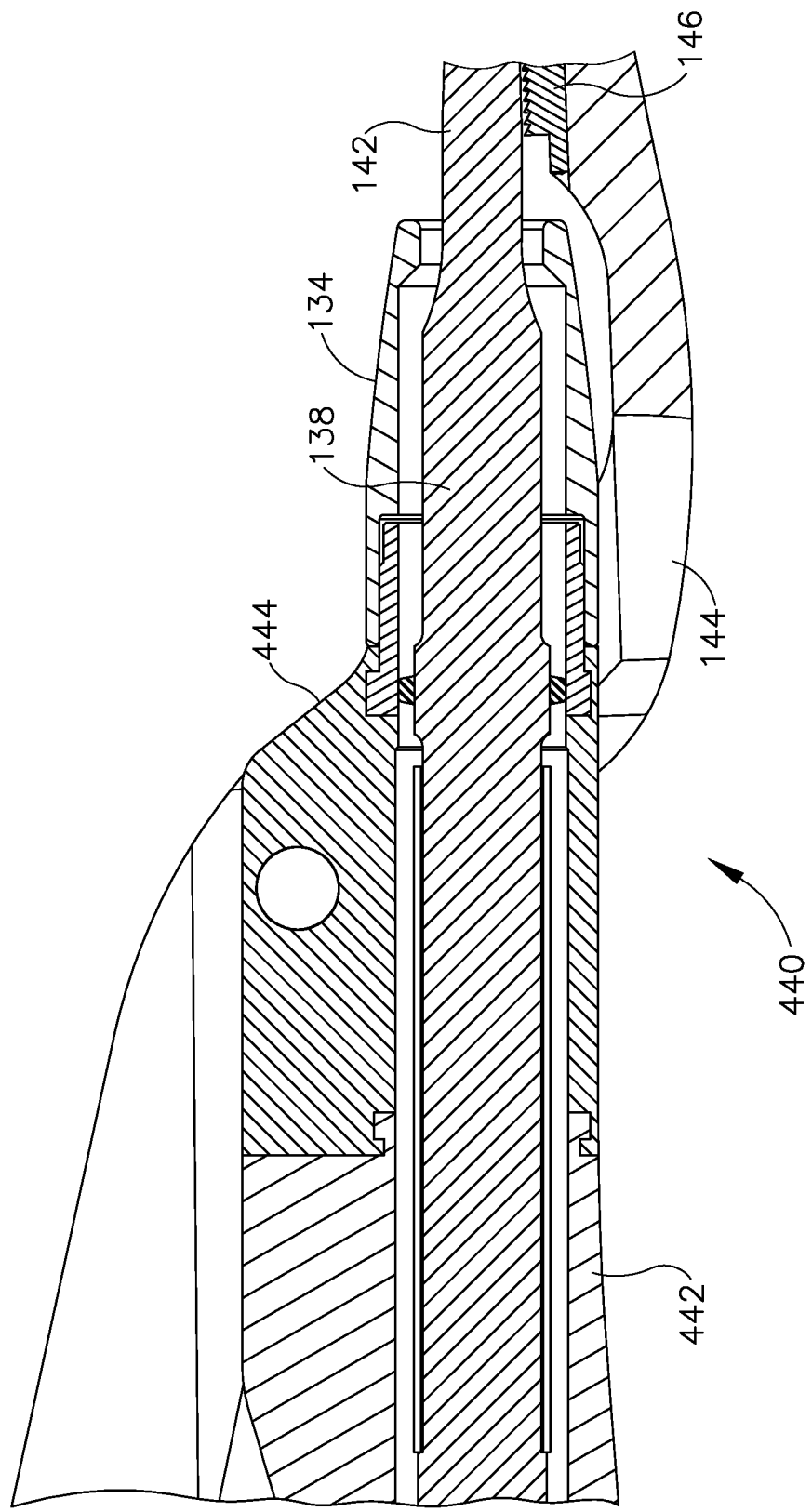
FIG. 30 depicts a cross-sectional view of the instrument of FIG. 29.
Figure 31A:
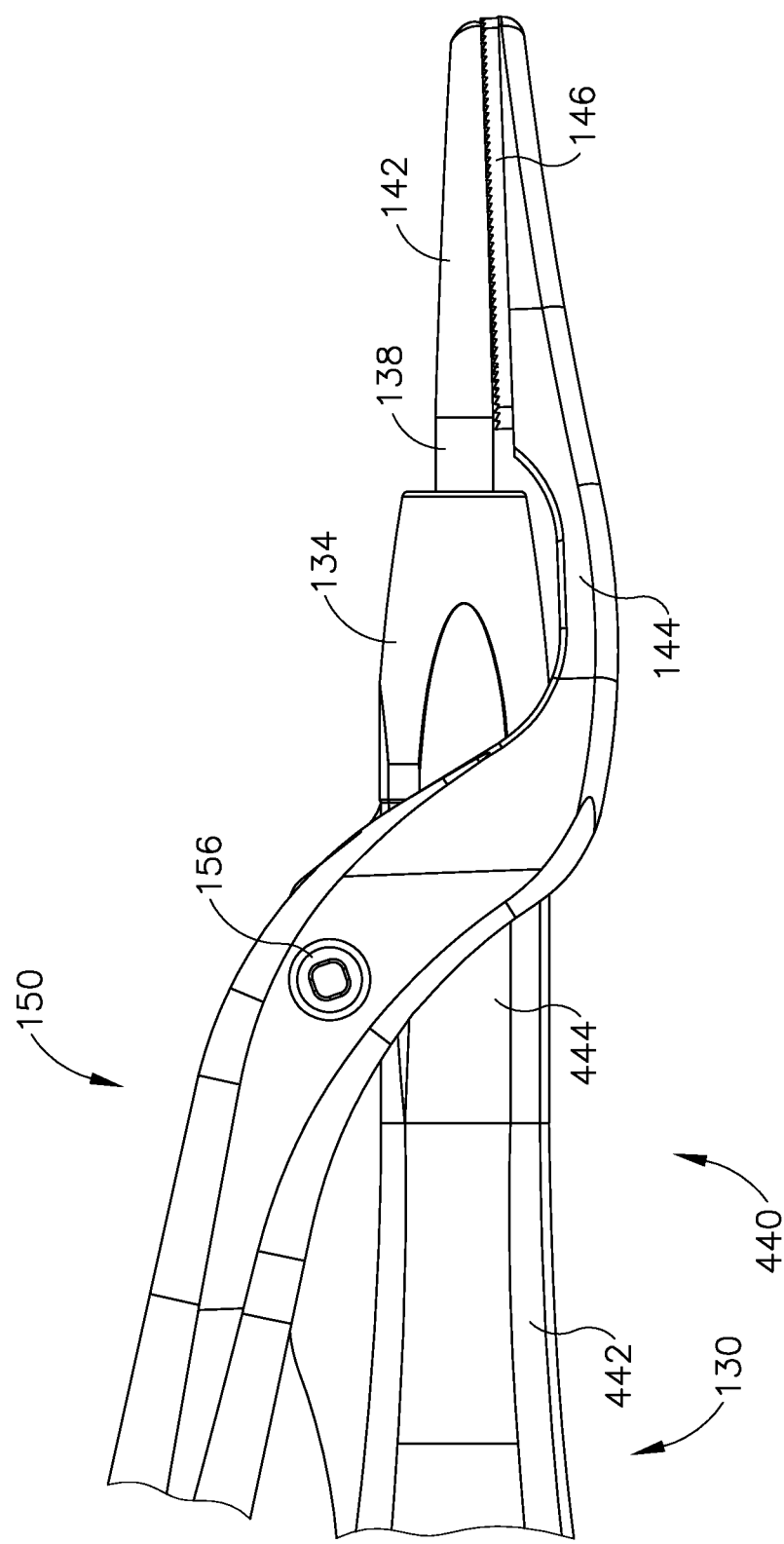
FIG. 31A depicts a side elevational view of the instrument of FIG. 29, with the clamp arm in a first rotational position.
Figure 31B:
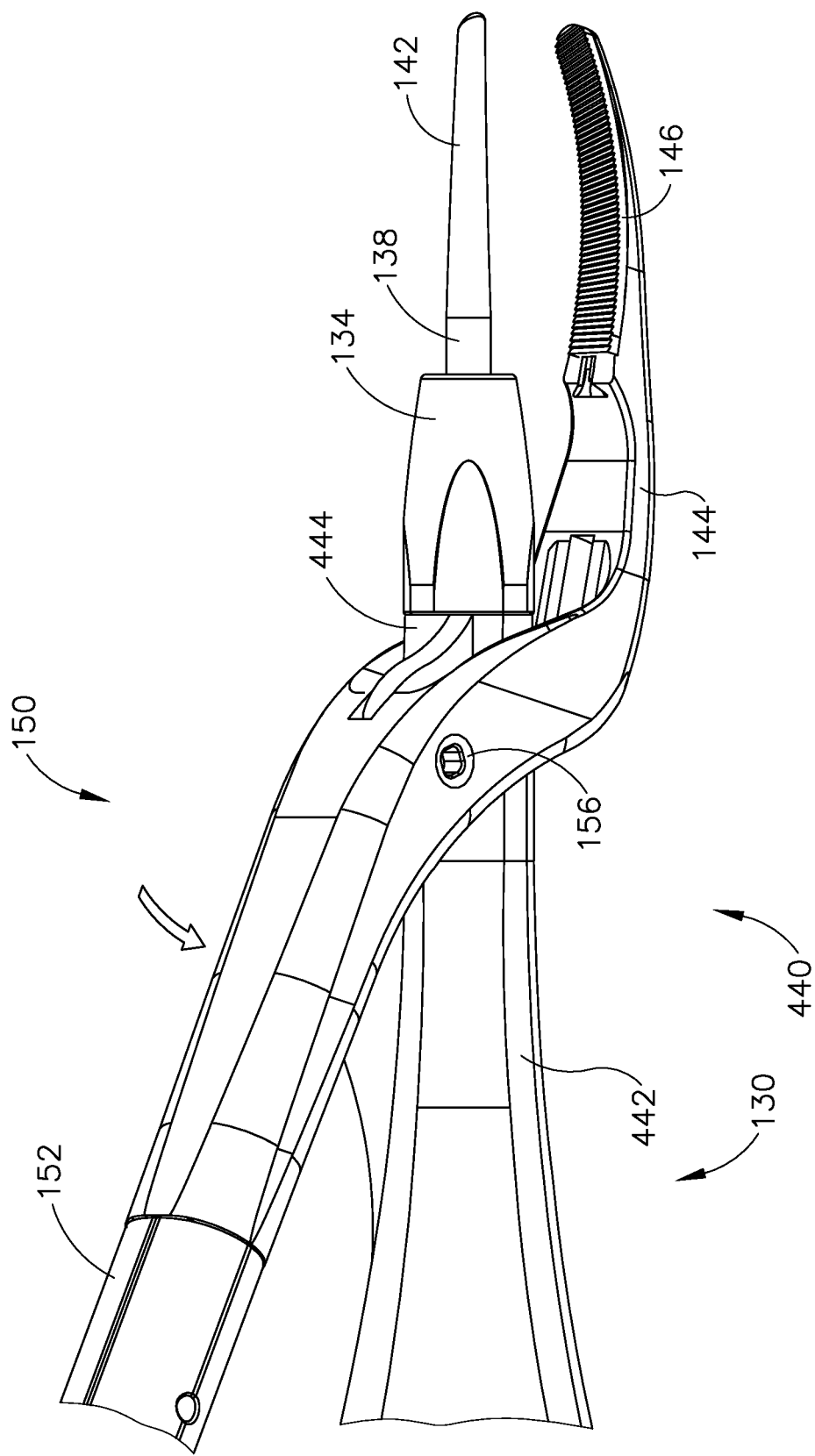
FIG. 31B depicts a side elevational view of the instrument of FIG. 29, with the clamp arm moved into a second rotational position.
Figure 31C:
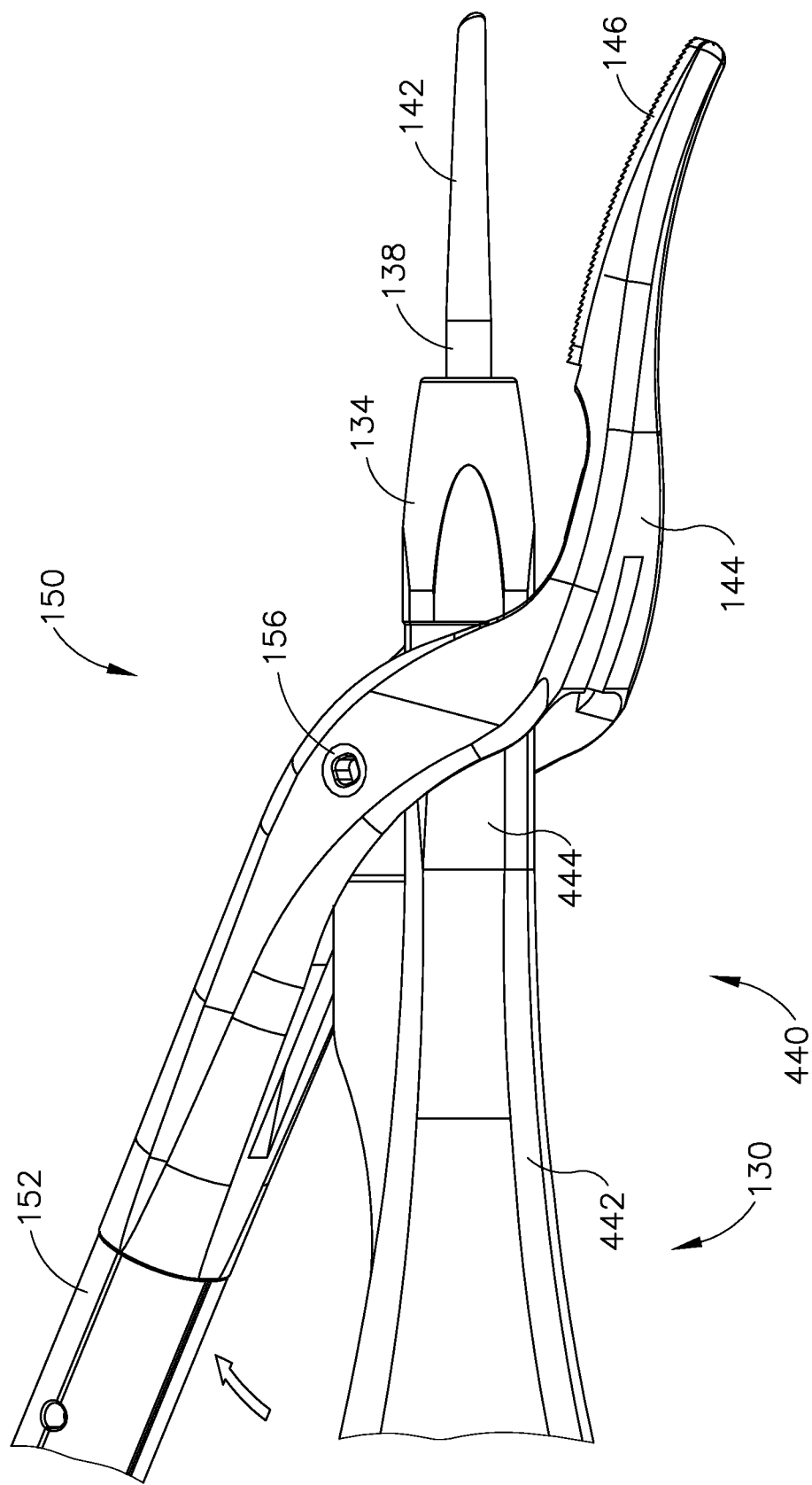
FIG. 31C depicts a side elevational view of the instrument of FIG. 29, with the clamp arm moved into a third rotational position.

As best seen in FIG. 30, rotatable member (444) is rotatably coupled with a distal end of outer sheath (442) and a proximal end of cap (134) such that rotatable member (444) is operable to rotate about the longitudinal axis of waveguide (138) relative to outer sheath (442). As noted above, clamp arm (144) is pivotably coupled with rotatable member (444). It should therefore be understood that clamp arm (144) and clamp arm assembly (150) are rotatable together about the longitudinal axis of waveguide (138) relative to outer sheath (442). FIGS. 31A-31C show rotation of clamp arm (144), clamp arm assembly (150), and rotatable member (444) about the longitudinal axis of waveguide (138) relative to outer sheath (442). It should be understood that clamp arm (144), clamp arm assembly (150), and rotatable member (444) are capable of rotating 360° about the longitudinal axis of waveguide (138) relative to outer sheath (442). It should also be appreciated that, at any point of rotation about the longitudinal axis of waveguide (138), clamp arm assembly (150) and clamp arm (144) may be pivoted toward and way from ultrasonic blade (142) to thereby clamp tissue.

In use, after the operator has clamped tissue between clamp arm (144) and ultrasonic blade (142) by driving clamp arm assembly (150) about the axis defined by pin (156) as shown in FIG. 31A, and after the operator has activated ultrasonic blade (142) to vibrate ultrasonically to sever and seal the clamped tissue, the operator may then drive clamp arm assembly (150) in a rotational motion about the axis defined by waveguide (138) as shown in FIGS. 31B-31C, while holding clamp arm (144) in a clamped position. This rotational movement of clamp arm (144) about the axis defined by waveguide (138), relative to ultrasonic blade (142), may prevent or cut tissue tags that might otherwise be present in the absence of such additional rotational movement.

While rotation mechanism (440) is discussed as being incorporated into instrument (100) in the present example, it should be understood that rotation mechanism (440) may be readily incorporated into instrument (10).

IV. Exemplary Rotational Support Devices

As discussed above, it may be desirable to provide mechanisms that allow waveguide (38, 138), ultrasonic blade (42, 142), and/or clamp arm (44, 144) to be selectively rotated relative to other components of instrument (10, 100). Waveguide (38, 138) and ultrasonic blade (42, 142) are secured to shaft assembly (30, 130) via pin (31, 133). Thus, it may further be desirable to provide rotational features that allow some degree of rotation of pin (31, 133) relative to shaft assembly (30, 130), to thereby enable rotation of waveguide (38, 138), ultrasonic blade (42, 142), and pin (31, 133) together relative to shaft assembly (30, 130). Various illustrative examples of an instrument that include such rotational features will be described in greater detail below, while other examples will be apparent to those of ordinary skill in the art in view of the teachings herein. It should be understood that the below examples may be viewed as variations of instruments (10, 100), such that various teachings below may be readily combined with various teachings above as will be apparent to those of ordinary skill in the art.

A. First Exemplary Rotational Support Device

Figure 32:
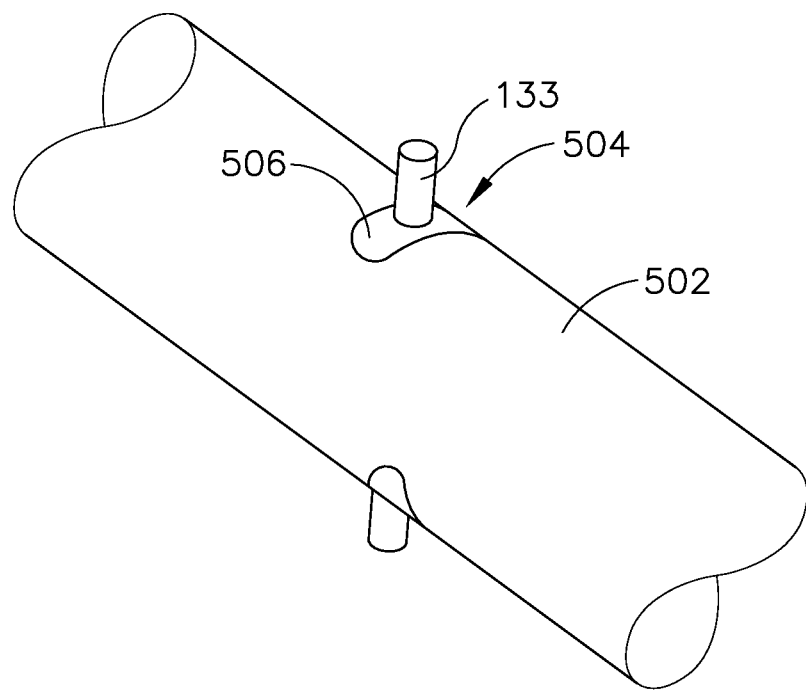
FIG. 32 depicts a perspective view of an exemplary ultrasonic blade suitable for incorporation into the instruments of FIG. 1 and FIG. 4 having a coupling feature to provide for rotation of the ultrasonic waveguide.
Figure 33A:
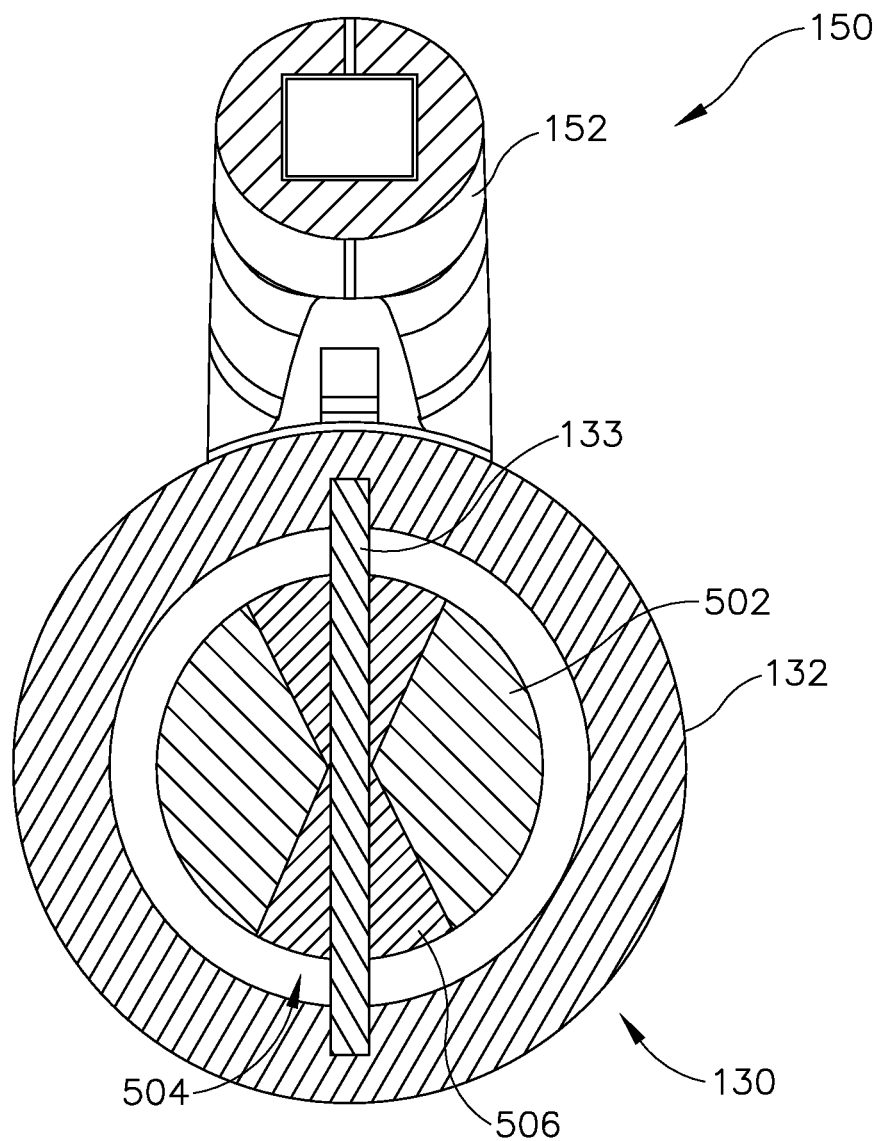
FIG. 33A depicts a cross-sectional view of a variation of the instrument of FIG. 4 with the coupling feature of FIG. 32, with the ultrasonic blade in a first rotational position.
Figure 33B:
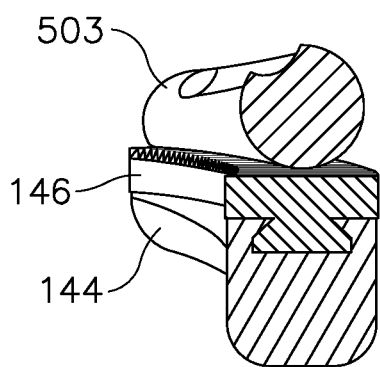
FIG. 33B depicts a cross-sectional view of the ultrasonic blade and the clamp arm of the instrument of FIG. 33A, with the ultrasonic blade in a first rotational position.
Figure 33C:
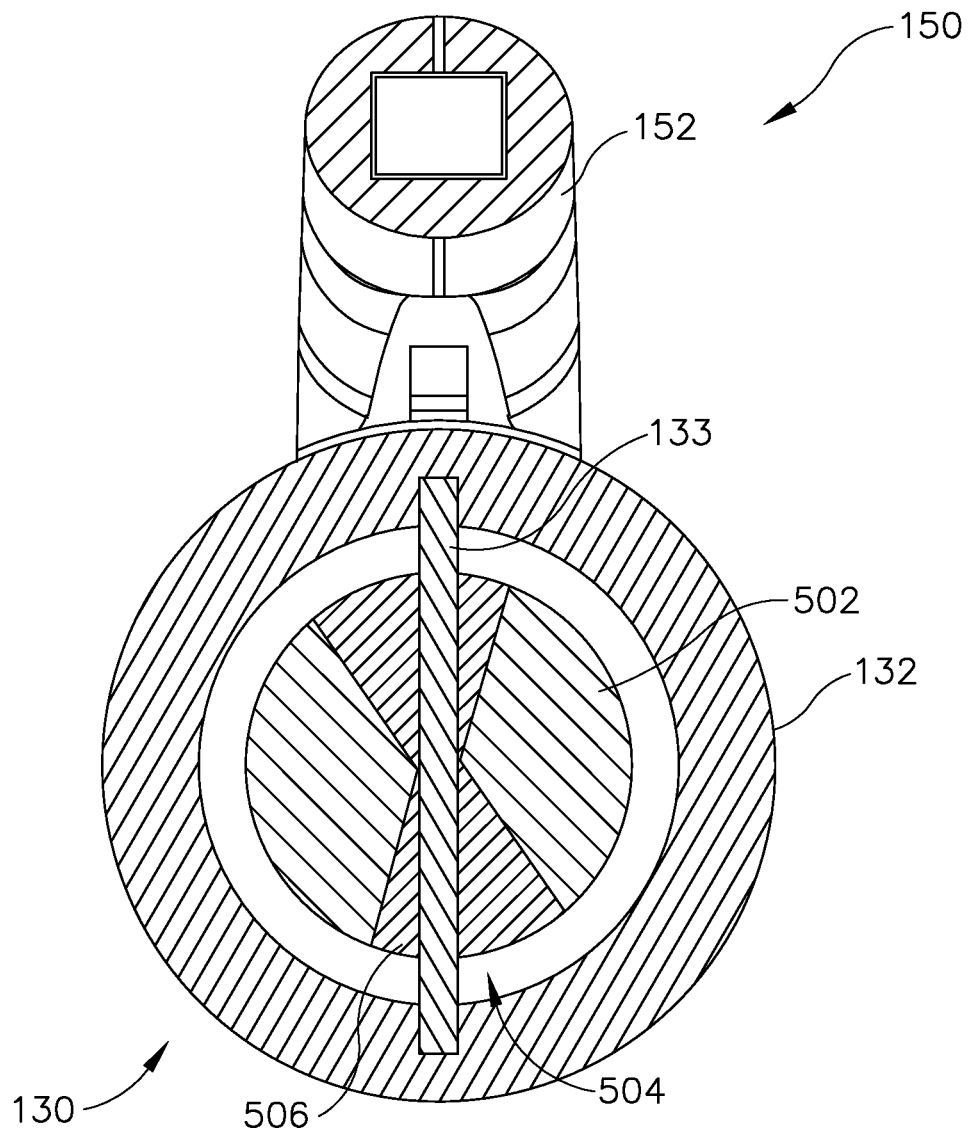
FIG. 33C depicts a cross-sectional view of the instrument of FIG. 33A, with the ultrasonic blade in moved into a second rotational position.
Figure 33D:
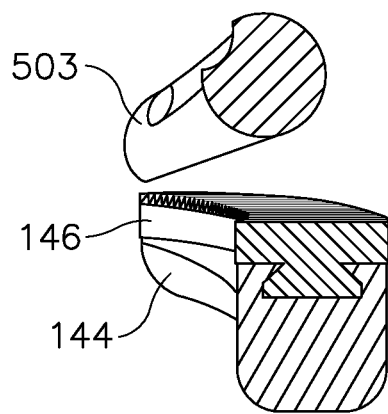
FIG. 33D depicts a cross-sectional view of the ultrasonic blade and the clamp arm of FIG. 33B, with the ultrasonic blade moved into the second rotational position.
Figure 33E:
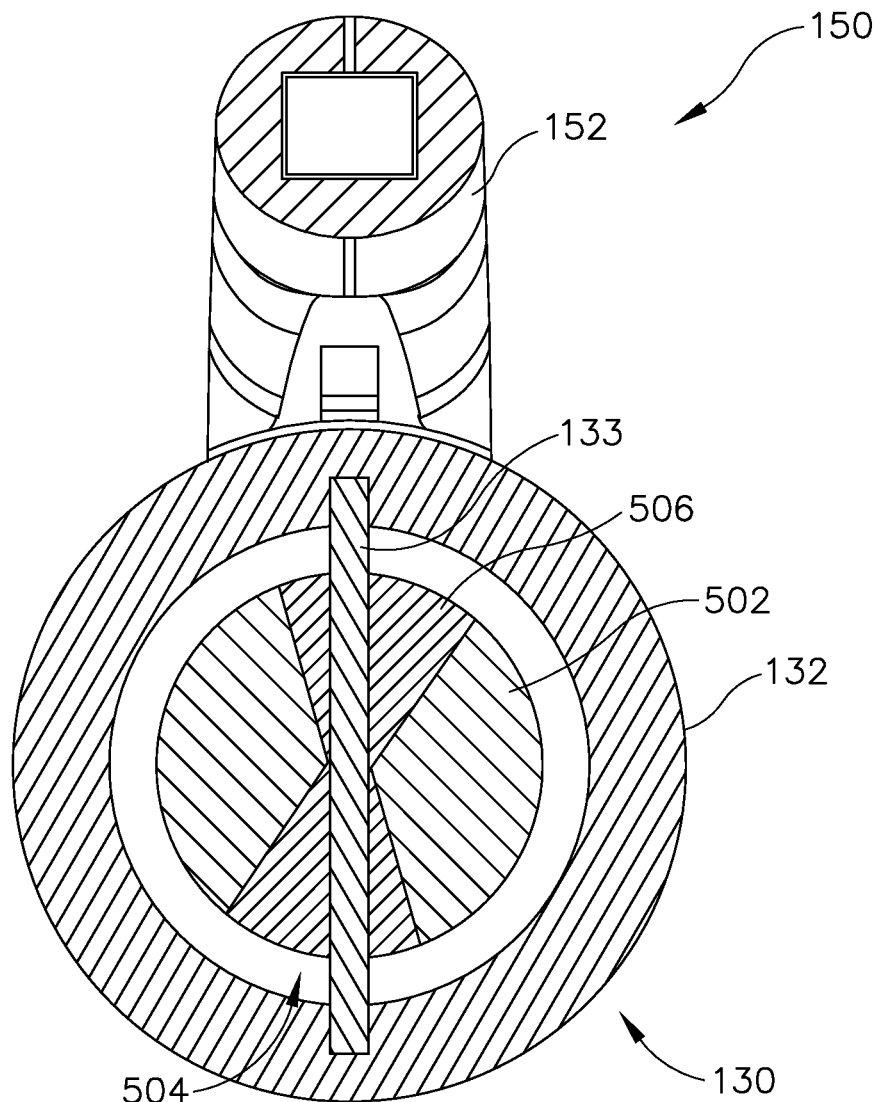
FIG. 33E depicts a cross-sectional view of the instrument of FIG. 33A, with the ultrasonic blade moved into a third rotational position.
Figure 33F:
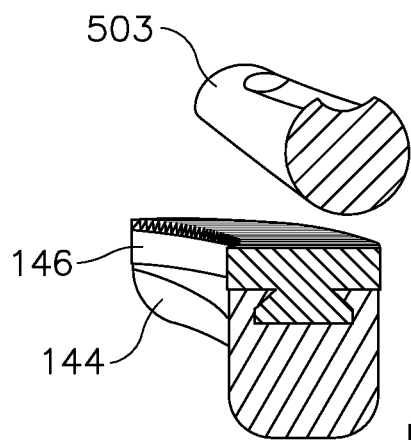
FIG. 33F depicts a cross-sectional view of the ultrasonic blade and the clamp arm of FIG. 33B, with the ultrasonic blade moved into the third rotational position.

FIGS. 32-33F show an exemplary rotational device (500) that may be readily incorporated into instrument (100). Rotational device (500) of the present example comprises an exemplary alternative waveguide (502). Waveguide (502) is configured to operate substantially similar to waveguide (138) discussed above except for the differences discussed below. In particular, waveguide (502) communicates acoustic vibrations at ultrasonic frequencies from an ultrasonic transducer to an ultrasonic blade (503) to thereby cut and/or seal tissue. As shown in FIGS. 33A, 33C, and 33E, pin (133) passes through an hourglass-shaped slot (504) formed in waveguide (502). Slot (504) of the present example is filled with a flexible elastomeric material (506), such that pin (133) is embedded within elastomeric material (506).

Waveguide (502) is operable to rotate relative to pin (133) as pin (133) rotates within slot (504). Pin (133) extends from waveguide (502) and into outer sheath (132) such that pin (133) remains stationary as waveguide (502) is rotated relative to pin (133) and outer sheath (132). Elastomeric material (506) provides sufficient flexibility to allow rotation of waveguide (502) relative to pin (133) as shown in FIGS. 33C and 33E; yet elastomeric material (506) also provides sufficient resilience to bias waveguide (502) to the nominal angular position shown in FIG. 33A.

FIGS. 33A, 33C, and 33E show rotational positions of waveguide (502); and FIGS. 33B, 33D, and 33F show the corresponding rotational positions of ultrasonic blade (503) relative to clamp arm (144). FIGS. 33A and 33B show waveguide (502) and ultrasonic blade (503) in a first rotational position. In this first rotational position, pin (133) is substantially centered within slot (504). Clamp arm (144) is parallel to ultrasonic blade (503) such that the entire length of ultrasonic blade (503) engages clamp pad (146) as clamp arm (144) is closed toward ultrasonic blade (503). Instrument (100) may include a knob and/or one or more other features that allow the operator to rotate waveguide (502) about the longitudinal axis of waveguide (502), relative to pin (133) and outer sheath (132). For instance, the operator may rotate waveguide (502) about the longitudinal axis of waveguide (502), relative to pin (133) and outer sheath (132), to the angular position shown in FIG. 33C and/or to the angular position shown in FIG. 33E. Alternatively, as will be described in greater detail below, waveguide (502) may be resiliently biased to the angular position shown in FIG. 33C or to the angular position shown in FIG. 33E.

FIGS. 33C and 33D show waveguide (502) and ultrasonic blade (503) in a second rotational position. In this second rotational position, waveguide (502) has been rotated counter-clockwise such that pin (133) is oriented obliquely within slot (504). Ultrasonic blade (503) is angled obliquely relative to clamp arm (144) such that the distal end of ultrasonic blade (503) engages clamp pad (146) first as clamp arm (144) is closed toward ultrasonic blade (503). In other words, the second rotational position is associated with a tip-loaded configuration for end effector (140). Such a tip-loaded configuration may be used to prevent tissue tags that might otherwise be left by end effector (140) if end effector (140) were actuated with ultrasonic blade (503) oriented substantially parallel to clamp pad (146). In addition or in the alternative, such a tip-loaded configuration may promote the use of the distal end of end effector (140) to make smaller "nibble" types of incisions in tissue. In some instances, after the distal end of ultrasonic blade (503) engages clamp pad (146) during closure of clamp arm (144), clamp arm (144) may move further through a second range of closure motion whereby the rest of the length of ultrasonic blade (503) engages clamp pad (146). For instance, elastomeric material (506) may deform to provide rotation of waveguide (502) from the position shown in FIG. 33C to the position shown in FIG. 33A as clamp arm (144) moves through the second range of motion. It should also be understood that the configuration of and relationship between pin (133) and elastomeric material (506) may provide the configuration of FIGS. 33C-33D as a nominal, default configuration, such that blade (503) is essentially biased to the tip-loaded configuration shown in FIGS. 33C-33D.

FIGS. 33E and 33F show waveguide (502) and ultrasonic blade (503) in a third rotational position. In this third rotational position, waveguide (502) has been rotated clockwise such that pin (133) is oriented obliquely within slot (504), in an opposite direction from the nominal plane. Ultrasonic blade (503) is angled obliquely relative to clamp arm (144) such that the proximal end of ultrasonic blade (503) engages clamp pad (146) first as clamp arm (144) is closed toward ultrasonic blade (503). In other words, the third rotational position is associated with a proximal-loaded configuration for end effector (140). Such a proximal-loaded configuration may be used to prevent tissue tags that might otherwise be left by end effector (140) if end effector (140) were actuated with ultrasonic blade (503) oriented substantially parallel to clamp pad (146). In some instances, after the proximal end of ultrasonic blade (503) engages clamp pad (146) during closure of clamp arm (144), clamp arm (144) may move further through a second range of closure motion whereby the rest of the length of ultrasonic blade (503) engages clamp pad (146). For instance, elastomeric material (506) may deform to provide rotation of waveguide (502) from the position shown in FIG. 33E to the position shown in FIG. 33A as clamp arm (144) moves through the second range of motion. It should also be understood that the configuration of and relationship between pin (133) and elastomeric material (506) may provide the configuration of FIGS. 33E-33F as a nominal, default configuration, such that blade (503) is essentially biased to the proximal-loaded configuration shown in FIGS. 33E-33F.

While rotational device (500) is discussed as being incorporated into instrument (100) in the present example, it should be understood that rotational device (500) may be readily incorporated into instrument (10).

B. Second Exemplary Rotational Support Device

Figure 34:
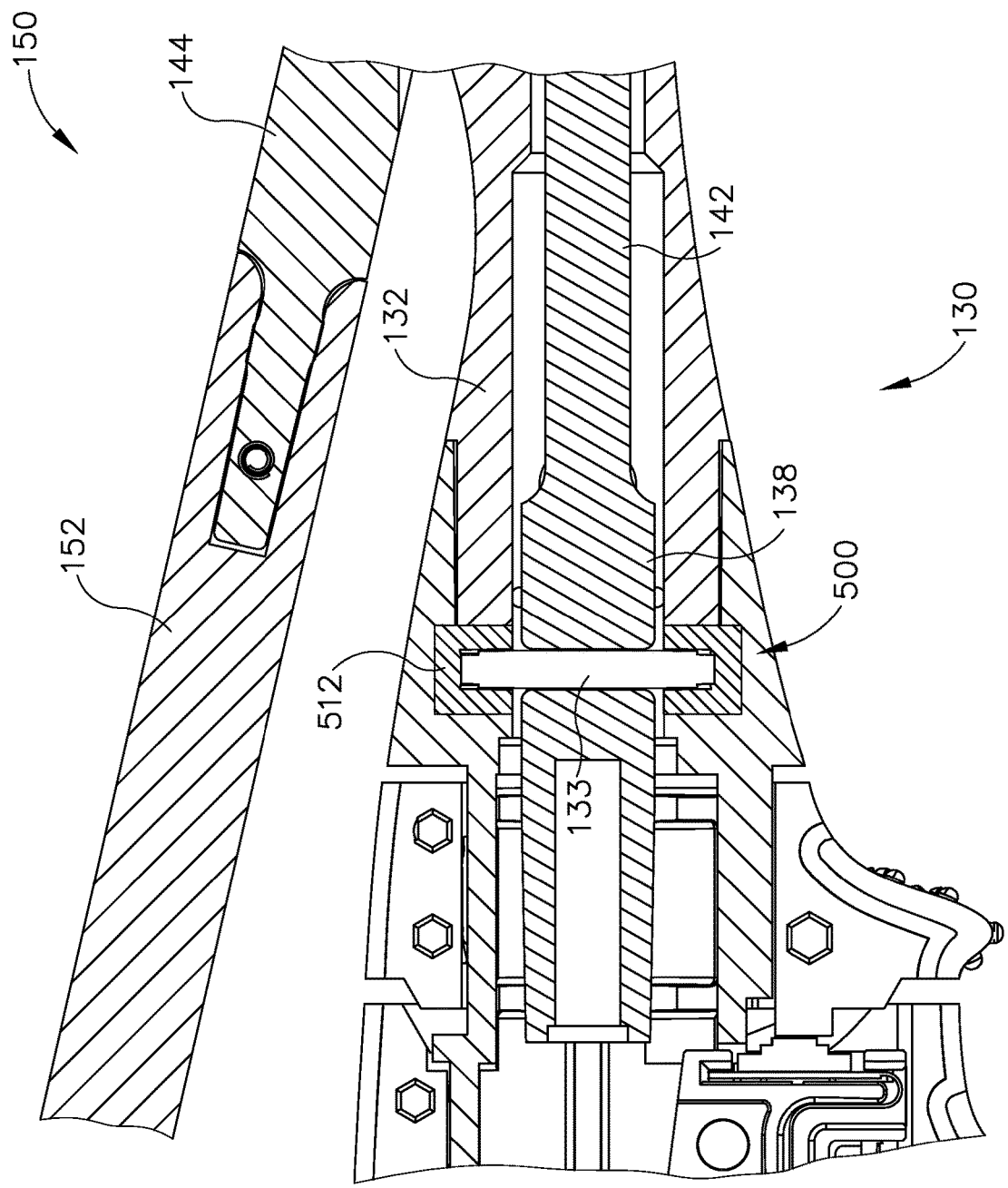
FIG. 34 depicts a cross-sectional view of another variation of the instrument of FIG. 4 having an exemplary alternative coupling feature to provide for rotation of the ultrasonic waveguide.

FIG. 34 shows an exemplary alternative rotational device (510) that may be readily incorporated into instrument (100). Rotational device (510) comprises an elastomeric bushing (512) that is secured within outer sheath (132) of shaft assembly (130). Pin (133) passes through waveguide (138) at a position along the length of waveguide (138) corresponding to a node associated with resonant ultrasonic vibrations communicated through waveguide (138). The free ends of pin (133) are embedded within elastomeric bushing (512). Elastomeric bushing (512) provides sufficient flexibility to allow rotation of waveguide (138) and pin (133) about the longitudinal axis of waveguide (138) relative to outer sheath (132); yet elastomeric bushing (512) also provides sufficient resilience to bias waveguide (138) and pin (133) to a nominal angular position about the longitudinal axis of waveguide (138) relative to outer sheath (132).

In some versions, elastomeric bushing (512) biases waveguide (138) and pin (133) to a nominal angular position about the longitudinal axis of waveguide (138) relative to outer sheath (132) where end effector (140) is in a tip-loaded configuration, similar to what is shown in FIG. 33D. Thus, as the operator pivotally drives clamp arm assembly (150) toward shaft assembly (130), the distal end of ultrasonic blade (142) engages clamp pad (146) first as clamp arm (144) is closed toward ultrasonic blade (142). After the distal end of ultrasonic blade (142) engages clamp pad (146) during closure of clamp arm (144), clamp arm (144) may move further through a second range of closure motion whereby the rest of the length of ultrasonic blade (142) engages clamp pad (146). For instance, elastomeric bushing (512) may deform to provide rotation of ultrasonic blade (142) from a position similar to that shown in FIG. 33D to the position similar to that shown in FIG. 33B as clamp arm (144) moves through the second range of motion. As the operator relaxes their grip on grip rings (124, 154), allowing clamp arm assembly (150) to pivot back away from shaft assembly (130), the resilient bias of elastomeric bushing (512) drives ultrasonic blade (142) back to the distal-loaded angular orientation.

In some other versions, elastomeric bushing (512) biases waveguide (138) and pin (133) to a nominal angular position about the longitudinal axis of waveguide (138) relative to outer sheath (132) where end effector (140) is in a proximal-loaded configuration, similar to what is shown in FIG. 33F. Thus, as the operator pivotally drives clamp arm assembly (150) toward shaft assembly (130), the proximal end of ultrasonic blade (142) engages clamp pad (146) first as clamp arm (144) is closed toward ultrasonic blade (142). After the proximal end of ultrasonic blade (142) engages clamp pad (146) during closure of clamp arm (144), clamp arm (144) may move further through a second range of closure motion whereby the rest of the length of ultrasonic blade (142) engages clamp pad (146). For instance, elastomeric bushing (512) may deform to provide rotation of ultrasonic blade (142) from a position similar to that shown in FIG. 33F to the position similar to that shown in FIG. 33B as clamp arm (144) moves through the second range of motion. As the operator relaxes their grip on grip rings (124, 154), allowing clamp arm assembly (150) to pivot back away from shaft assembly (130), the resilient bias of elastomeric bushing (512) drives ultrasonic blade (142) back to the proximal-loaded angular orientation.

In still other versions, elastomeric bushing (512) biases waveguide (138) and pin (133) to a nominal angular position about the longitudinal axis of waveguide (138) relative to outer sheath (132) where ultrasonic blade (142) is parallel to clamp arm (144), such that the entire length of ultrasonic blade (142) engages clamp pad (146) as clamp arm (144) is closed toward ultrasonic blade (503), similar to what is shown in FIG. 33B. Instrument (100) may include a knob and/or one or more other features that allow the operator to rotate waveguide (138) about the longitudinal axis of waveguide (138), relative to shaft assembly (130) and clamp arm assembly (150). For instance, the operator may rotate waveguide (138) about the longitudinal axis of waveguide (138), relative to shaft assembly (130) and clamp arm assembly (150), to the orient ultrasonic blade (142) at an angular position similar to the one shown in FIG. 33C and/or the one shown in FIG. 33E. This may be done while tissue is clamped between ultrasonic blade (142) and clamp pad (146). The rotation of ultrasonic blade (142) while tissue is clamped between ultrasonic blade (142) and clamp pad (146) may cut any tissue tags that might otherwise be left in tissue clamped between ultrasonic blade (142) and clamp pad (146).

In addition to providing a resilient bias and deformability, elastomeric bushing (512) may also dampen rotational vibration of waveguide (138) and/or noise from pin (133) to shaft assembly (130). It should also be understood that elastomeric bushing (512) may be configured to provide greater rotational compliance than axial compliance. In some variations, elastomeric bushing (512) is replaced with some other resilient member. By way of example only, rotational device (510) may instead comprise one or more leaf springs that are interposed between pin (133) and shaft assembly (130), to resiliently bias waveguide (138) to some nominal angular position while still allowing waveguide to rotate from that nominal angular position about the longitudinal axis of waveguide (138). Other suitable ways in which rotational device (510) may be configured will be apparent to those of ordinary skill in the art in view of the teachings herein. While rotational device (510) is discussed as being incorporated into instrument (100) in the present example, it should be understood that rotational device (510) may be readily incorporated into instrument (10).

V. Exemplary End Effector Variations

The examples described above provide modified relative movement between ultrasonic blade (42, 142) and clamp arm (44, 144) in order to prevent or otherwise address the occurrence of tissue tags. It should also be understood that the configuration of ultrasonic blade (42, 142) and/or clamp arm (44, 144) may also be modified in order to prevent or otherwise address the occurrence of tissue tags. Such modifications may be provided in addition to or in lieu of modifying the relative movement between ultrasonic blade (42, 142) and clamp arm (44, 144). Various merely illustrative examples of modifications to ultrasonic blade (42, 142)

and clamp arm (44, 144) are described in greater detail below; while still other examples will be apparent to those of ordinary skill in the art in view of the teachings herein. It should be understood that the below examples may be viewed as variations of instruments (10, 100), such that various teachings below may be readily combined with various teachings above as will be apparent to those of ordinary skill in the art.

A. Exemplary Ultrasonic Blade Variation

Figure 35:
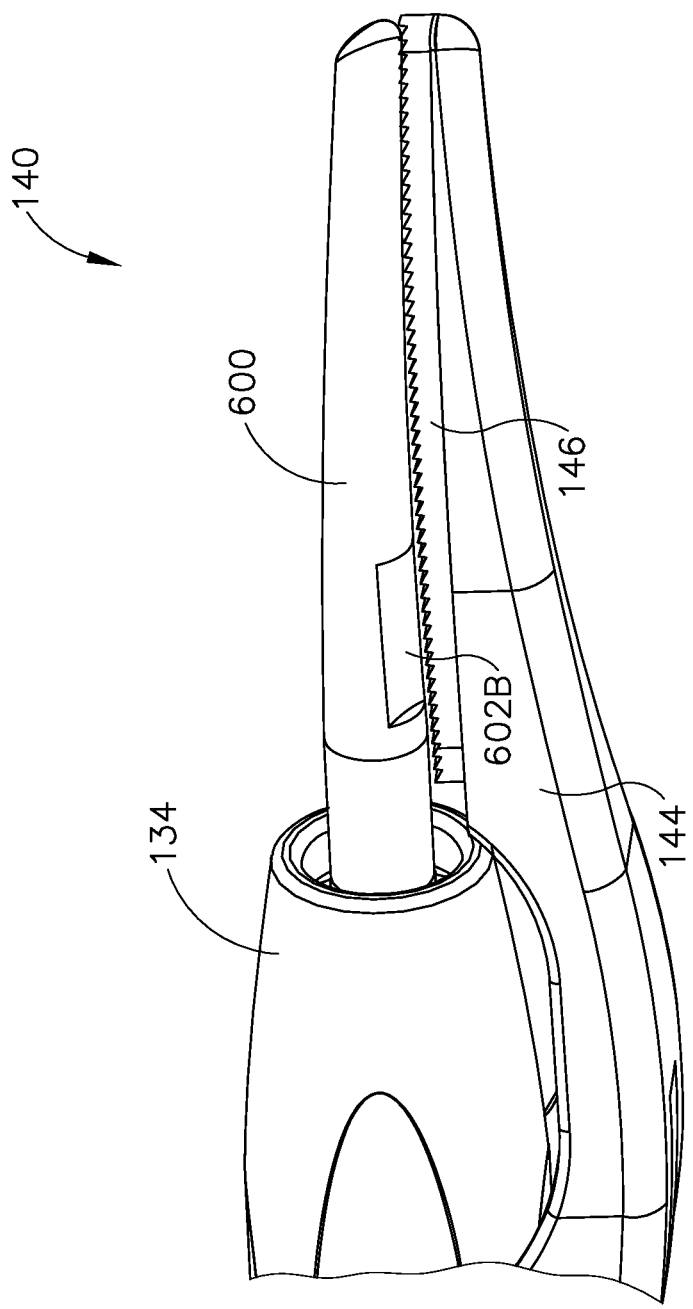
FIG. 35 depicts a perspective view of another variation of the instrument of FIG. 4 having an exemplary alternative ultrasonic blade.
Figure 36:
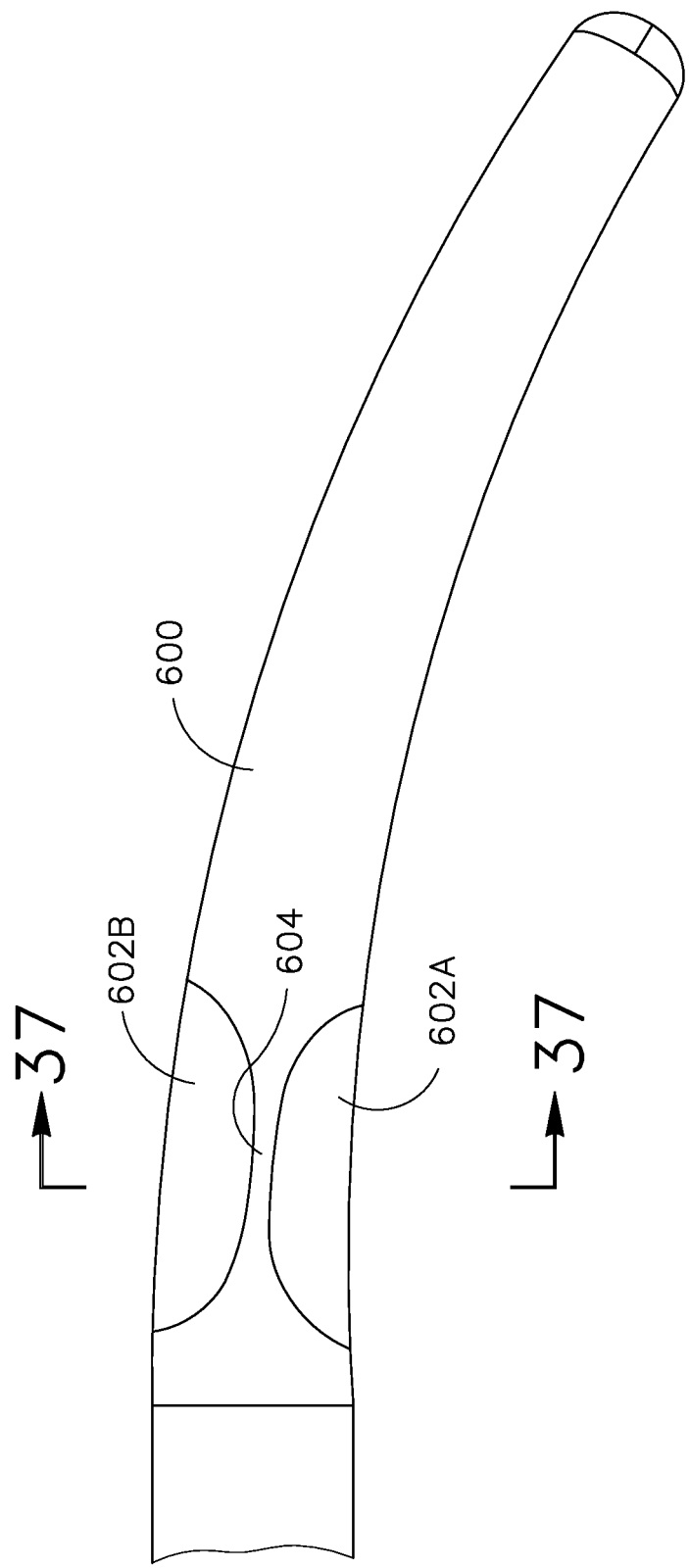
FIG. 36 depicts a top view of the ultrasonic blade of FIG. 35.
Figure 37:
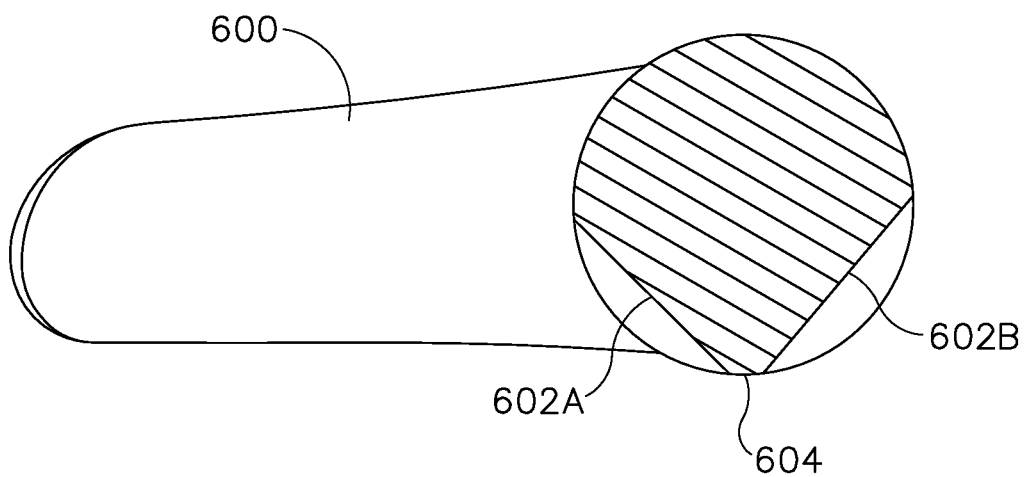
FIG. 37 depicts a cross-sectional view of the ultrasonic blade of FIG. 35, taken along line 37-37 of FIG. 36.

FIGS. 35-37 show an exemplary ultrasonic blade (600) that may be readily incorporated into instrument (100). Ultrasonic blade (600) of the present example is configured to operate substantially similar to ultrasonic blade (142) discussed above except for the differences discussed below. In particular, ultrasonic blade (600) is operable to transect and/or seal tissue clamped between clamp arm (144) and ultrasonic blade (600). A proximal portion of ultrasonic blade (600) comprises a pair of angled cutouts (602A, 602B) formed in opposite sides of ultrasonic blade (600). Angled cutouts (602A, 602B) define a bottom surface (604) having a minimized contact area. Angled cutouts (602A, 602B) and bottom surface (604) define a V-shaped profile configured to bear against tissue clamped between ultrasonic blade (600) and clamp pad (146) of clamp arm (144). The minimal contact area presented by bottom surface (604) causes a greater amount of pressure to be applied to tissue clamped between the proximal portion of ultrasonic blade (600) and clamp pad (146) than would otherwise be applied in the absence of angled cutouts (602A, 602B). It should therefore be understood that ultrasonic blade (600) is operable to apply an increased amount of pressure to tissue clamped between the proximal portion of ultrasonic blade (600) and clamp pad (146) to thereby prevent the formation of tissue tags at the region of angled cutouts (602A, 602B). While angled cutouts (602A, 602B) are formed in the proximal portion of ultrasonic blade (600) in this example, it should be understood that angled cutouts (602A, 602B) may be defined in any appropriate portion of ultrasonic blade (600) and along any suitable length of ultrasonic blade (600). For instance, angled cutouts (602A, 602B) and may be formed in a distal portion of ultrasonic blade (600).

While ultrasonic blade (600) is discussed as being incorporated into instrument (100) in the present example, it should be understood that ultrasonic blade (600) may be readily incorporated into instrument (10).

B. Exemplary Clamp Pad Variation

Figure 38:
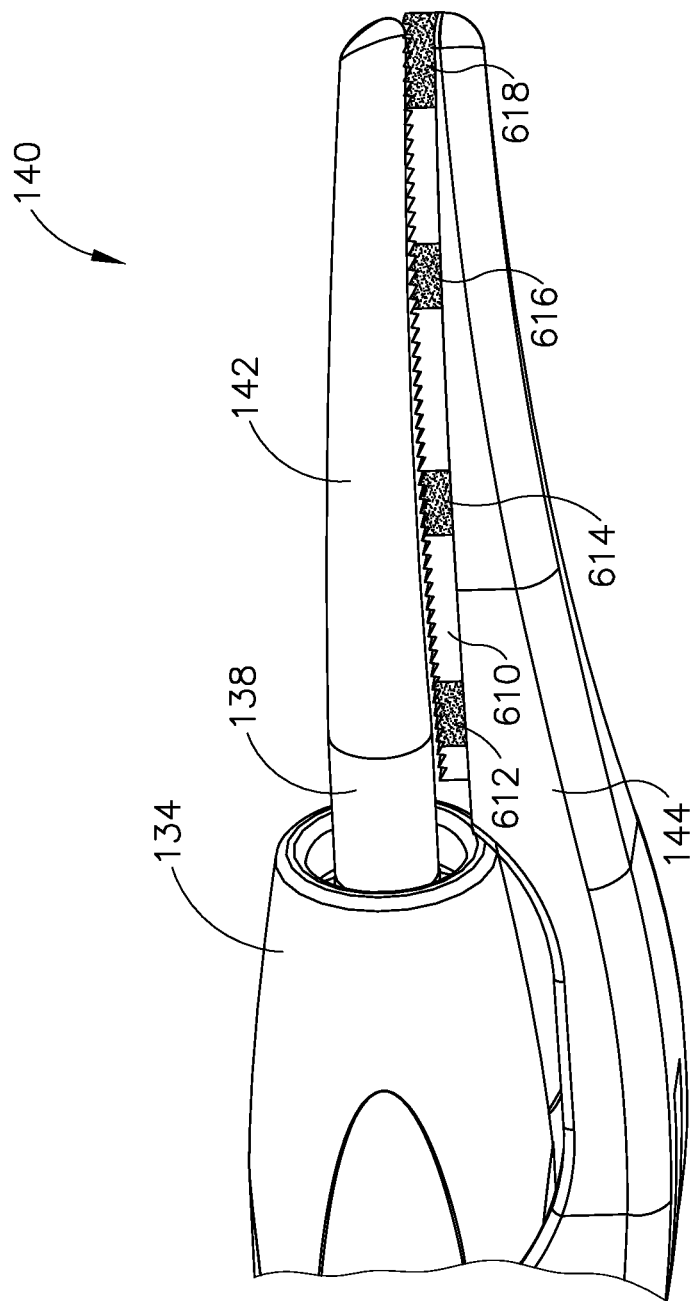
FIG. 38 depicts a perspective view of another variation the instrument of FIG. 4 having an exemplary alternative clamp pad.
Figure 39:
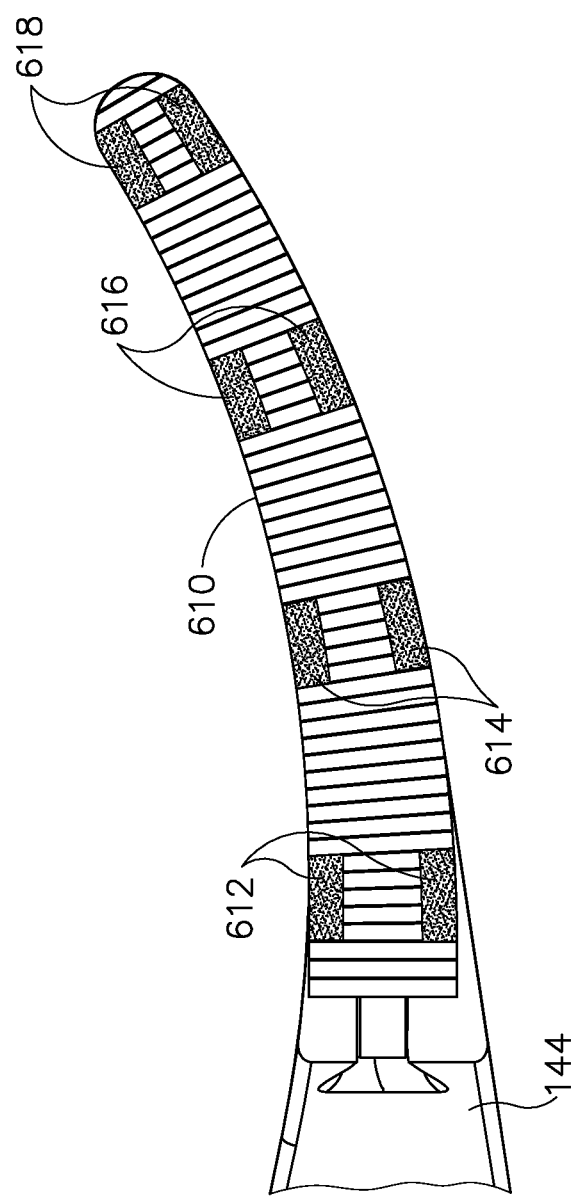
FIG. 39 depicts a top view of the clamp pad of FIG. 38.

FIGS. 38-39 show an exemplary clamp pad (610) that may be readily incorporated into instrument (100). Clamp pad (610) of the present example is configured to operate substantially similar to clamp pad (146) discussed above except for the differences discussed below. In particular, clamp pad (610) is secured to clamp arm (144) such that tissue may be clamped between clamp pad (610) and ultrasonic blade (142) to transect and/or seal the tissue. Clamp pad (610) of the present example comprises a plurality of electrodes (612, 614, 616, 618) disposed along the length of clamp pad (610) in a spaced-apart relationship, as best seen in FIG. 39.

Electrodes (612, 614, 616, 618) are provided as pairs that are configured to measure electrical impedance across the clamped tissue that is positioned between the electrodes (612, 614, 616, 618) of each pair. In other words, the distal-most pair of electrodes (618) may sense electrical impedance across clamped tissue that is positioned between the distal-most pair of electrodes (618), the proximal-most pair of electrodes (612) may sense electrical impedance across clamped tissue that is positioned between the proximal-most pair of electrodes (618), and so on. Electrodes (612, 614, 616, 618) may all sense impedance simultaneously or in a sequence (e.g., beginning at the distal-most pair of electrodes (618) and ending at the proximal-most pair of electrodes (618), etc.). Electrodes (612, 614, 616, 618) may also sense impedance many times per second.

Figure 40:
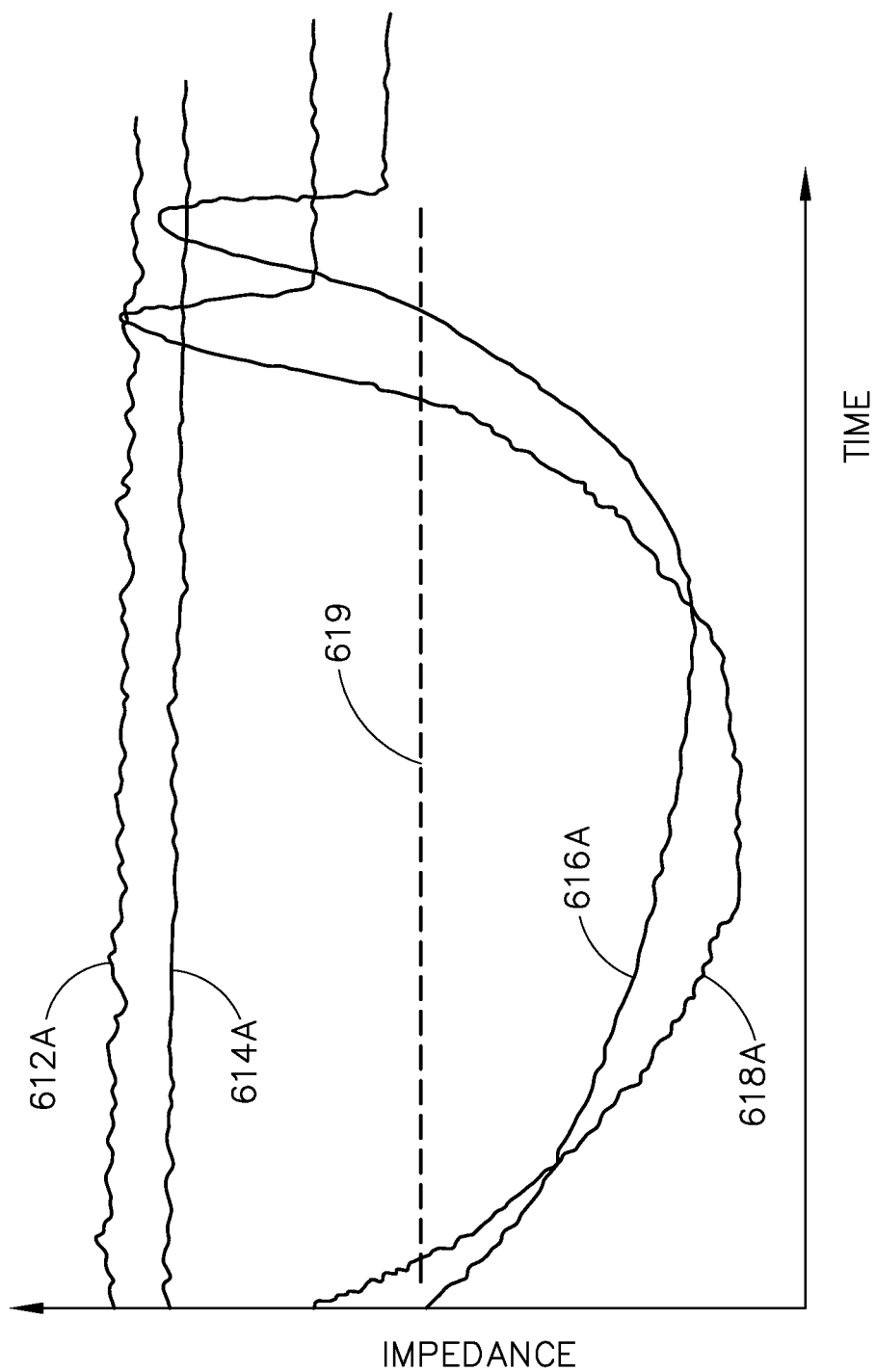
FIG. 40 depicts a diagram of electrical impedance sensed by the clamp pad of FIG. 38.

If any particular pair of electrodes (612, 614, 616, 618) sense an impedance value above a certain threshold, this may indicate that there is no tissue positioned between that particular pair of electrodes (612, 614, 616, 618). If any particular pair of electrodes (612, 614, 616, 618) sense an impedance value below a certain threshold, this may indicate that there is tissue positioned between that particular pair of electrodes (612, 614, 616, 618). Electrodes (612, 614, 616, 618) may thus collectively sense the distribution of tissue along the length of clamp pad (610). In the example shown in FIG. 40, electrodes (612, 614) each sense a respective level of electrical impedance (612A, 614A) above predetermined threshold (619) such that electrodes (612, 614) sense the absence of tissue in the region of clamp pad (610) monitored by electrodes (612, 614). Additionally, electrodes (616, 618) each sense a respective level of electrical impedance (616A, 618A) below predetermined threshold (619) such that electrodes (616, 618) sense the presence of tissue in the region of clamp pad (610) monitored by electrodes (616, 618).

Electrodes (612, 614, 616, 618) may be in communication with a control module (e.g., microprocessor, ASIC, etc.) that is operable to execute a control logic based upon the distribution of tissue along the length of clamp pad (610) as sensed by electrodes (612, 614, 616, 618). This control module may also be in communication with a feature that is operable to rotate clamp arm (144) relative to ultrasonic blade (142); and/or rotate ultrasonic blade (142) relative to clamp arm (144). By way of example only, the control module may be in communication with a feature like motor (242) as described above with respect to the example depicted in FIGS. 10-11D. Once the presence of tissue is sensed between one or more pairs of electrodes (612, 614, 616, 618), the control module may drive motor (242) or some other feature to provide relative rotation between ultrasonic blade (142) and clamp arm (144) to provide increased pressure at the distal ends of clamp pad (610) and ultrasonic blade (142) or at the proximal ends of clamp pad (610) and ultrasonic blade (142), based on the sensed location of tissue along the length of clamp pad (610). In addition to or as an alternative to driving a feature like motor (242), the control module may also provide audible and/or visual feedback to the operator to indicate where tissue is positioned along the length of clamp pad (610), based on impedance values sensed by electrodes (612, 614, 616, 618).

While the control module drives a feature like motor (242) to provide a rolling contact between clamp pad (610) and ultrasonic blade (142), the control module may continue to monitor the impedance values sensed by electrodes (612, 614, 616, 618). If the control module adjusts the relative angular positioning of clamp pad (610) and ultrasonic blade (142), and determines based on impedance values sensed by electrodes (612, 614, 616, 618) that there is still tissue positioned between clamp pad (610) and ultrasonic blade (142), the control module may continue to drive a feature like motor (242) to continue adjusting the relative angular positioning of clamp pad (610) and ultrasonic blade (142). For instance, clamp pad (610) and/or ultrasonic blade (142) may be slowly or rapidly rocked about a longitudinal axis in an oscillatory motion until all electrodes (612, 614, 616, 618) sense an impedance value above the threshold. In addition or in the alternative, the control module may drive a user feedback feature that indicates to the user when all electrodes (612, 614, 616, 618) sense an impedance value above the threshold, which may indicate that the entire length of tissue between clamp pad (610) and ultrasonic blade (142) has been cut without leaving tissue tags. Still other suitable ways in which an instrument (100) incorporating clamp pad (610) may be operated will be apparent to those of ordinary skill in the art in view of the teachings herein.

While clamp pad (610) is discussed as being incorporated into instrument (100) in the present example, it should be understood that clamp pad (610) and associated features may be readily incorporated into instrument (10).

C. Exemplary Clamp Arm and Pin Variation

Figure 41A:
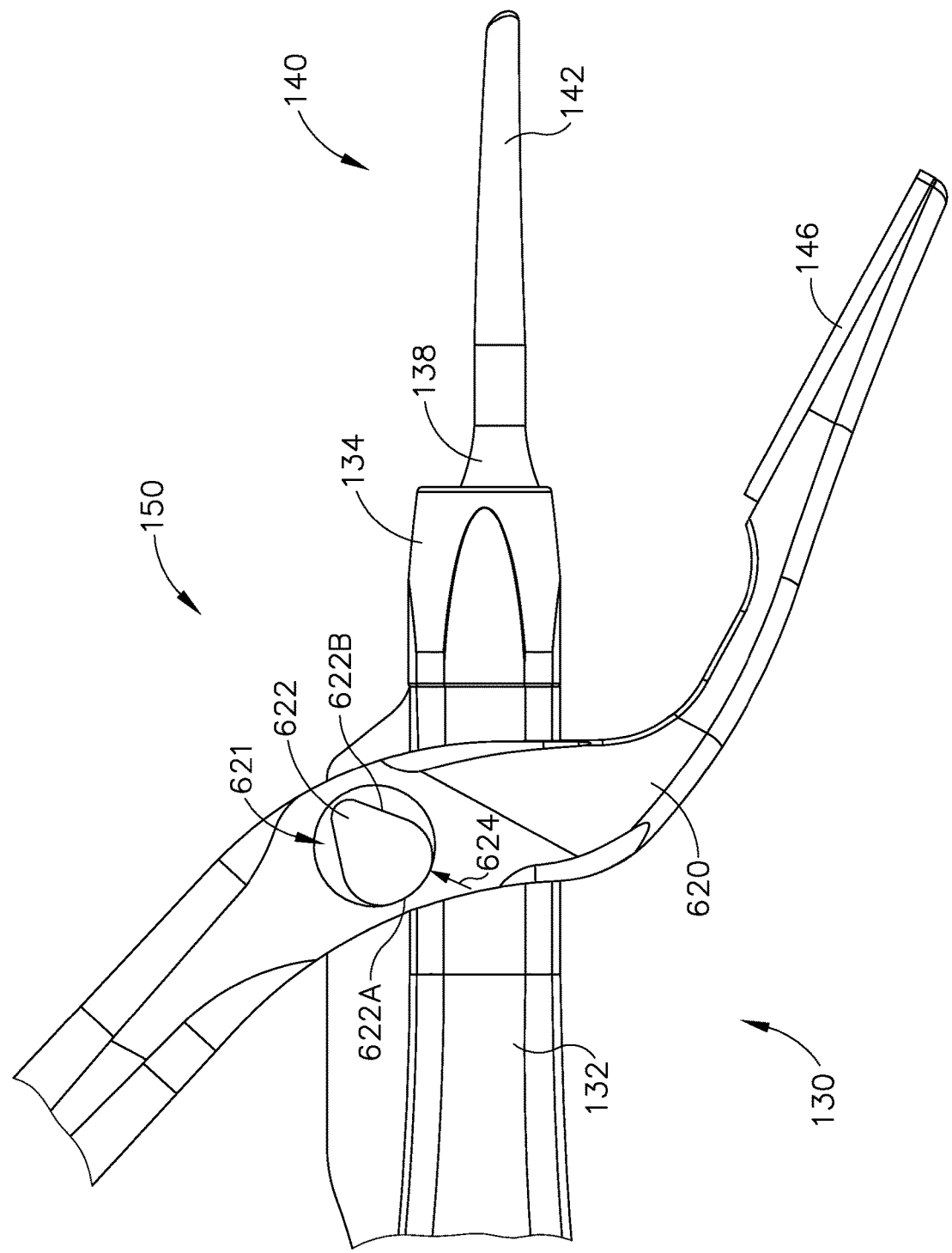
FIG. 41A depicts a side elevational view of another variation of the instrument of FIG. 4 having an exemplary pivoting cam mechanism, with the instrument in an open configuration.
Figure 41B:
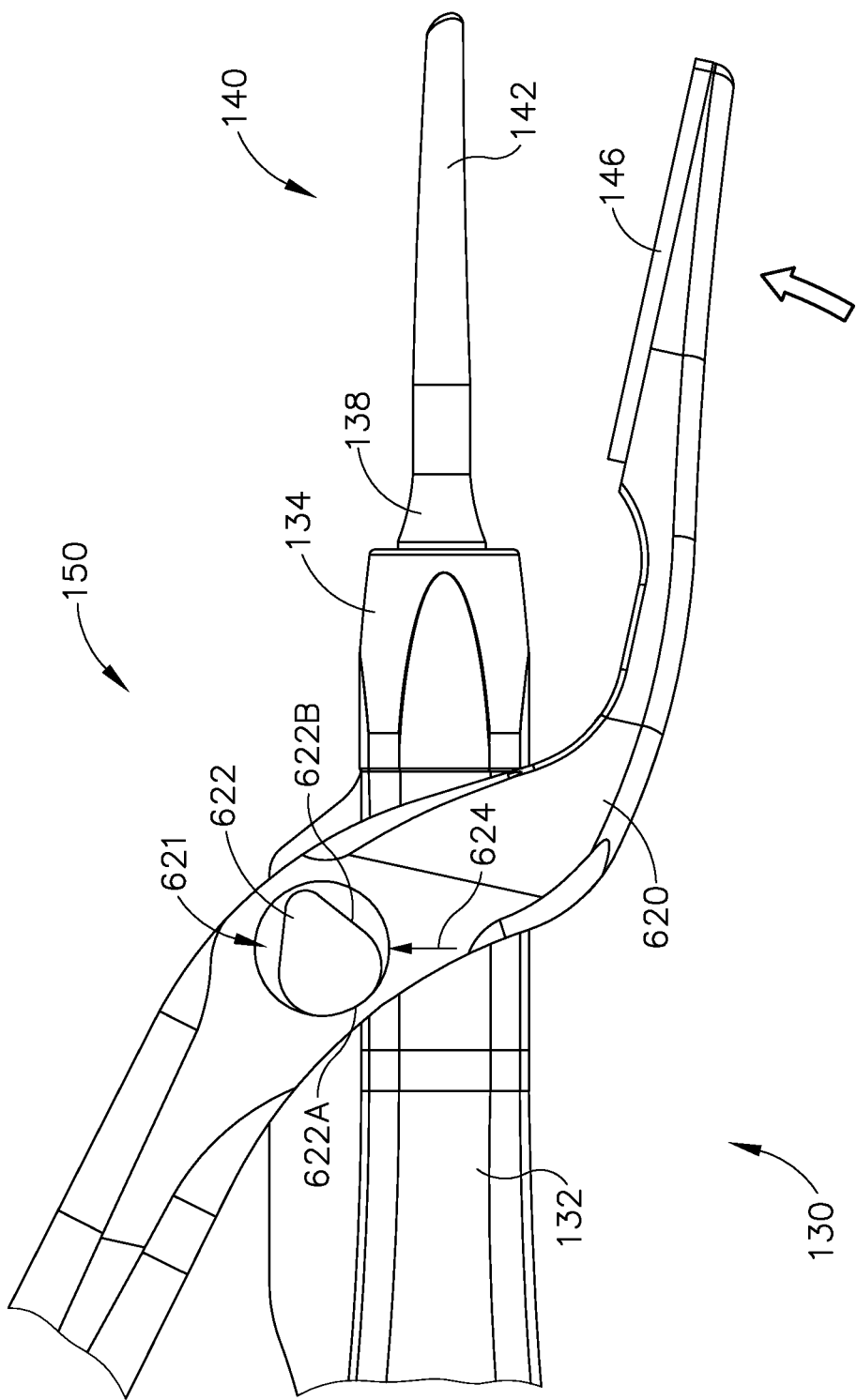
FIG. 41B depicts a side elevational view of the instrument of FIG. 41A, with the instrument moved into a partially closed configuration.
Figure 41C:
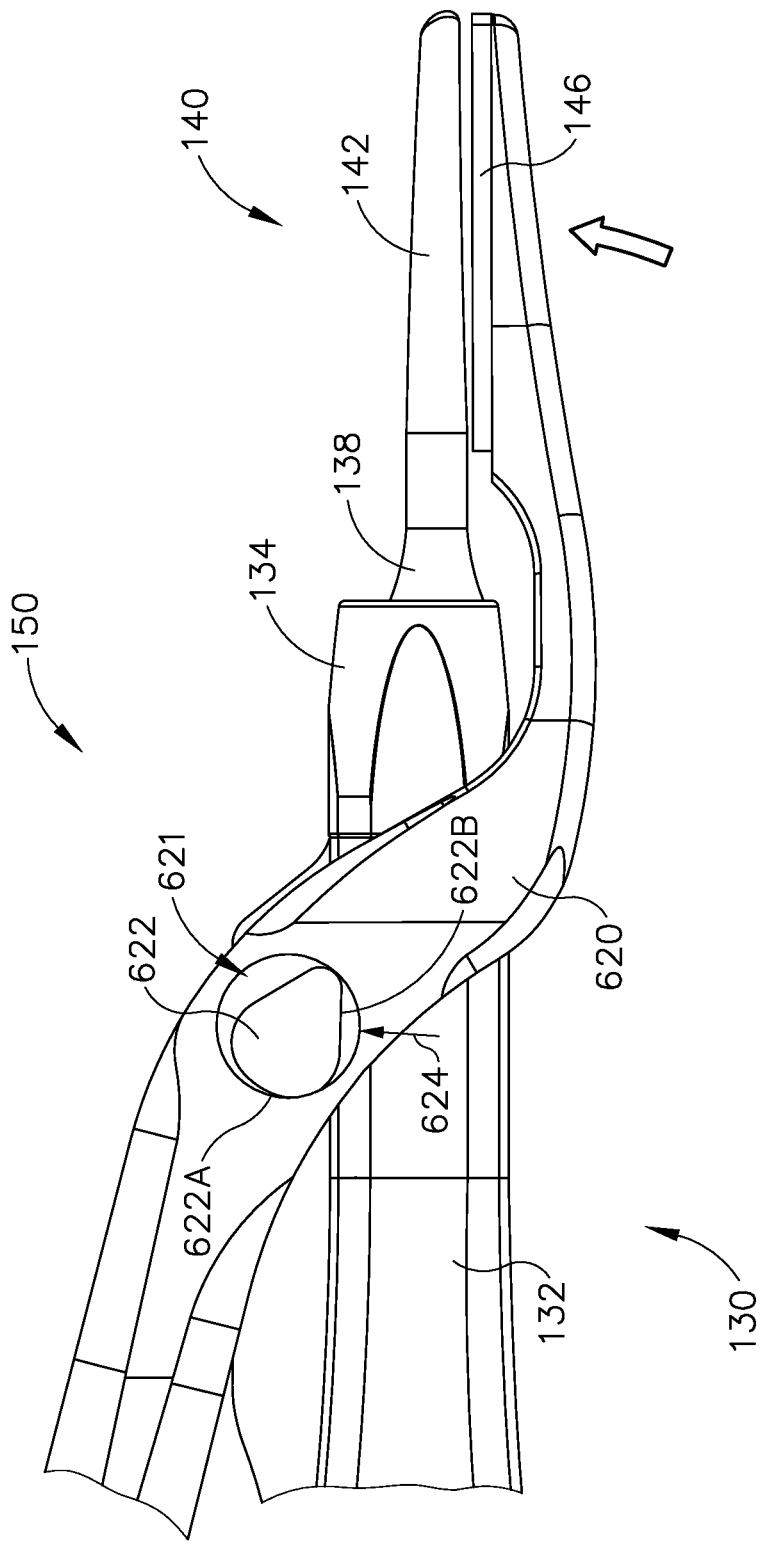
FIG. 41C depicts a side elevational view of the instrument of FIG. 41A, with the instrument moved into a completely closed position.
Figure 42:
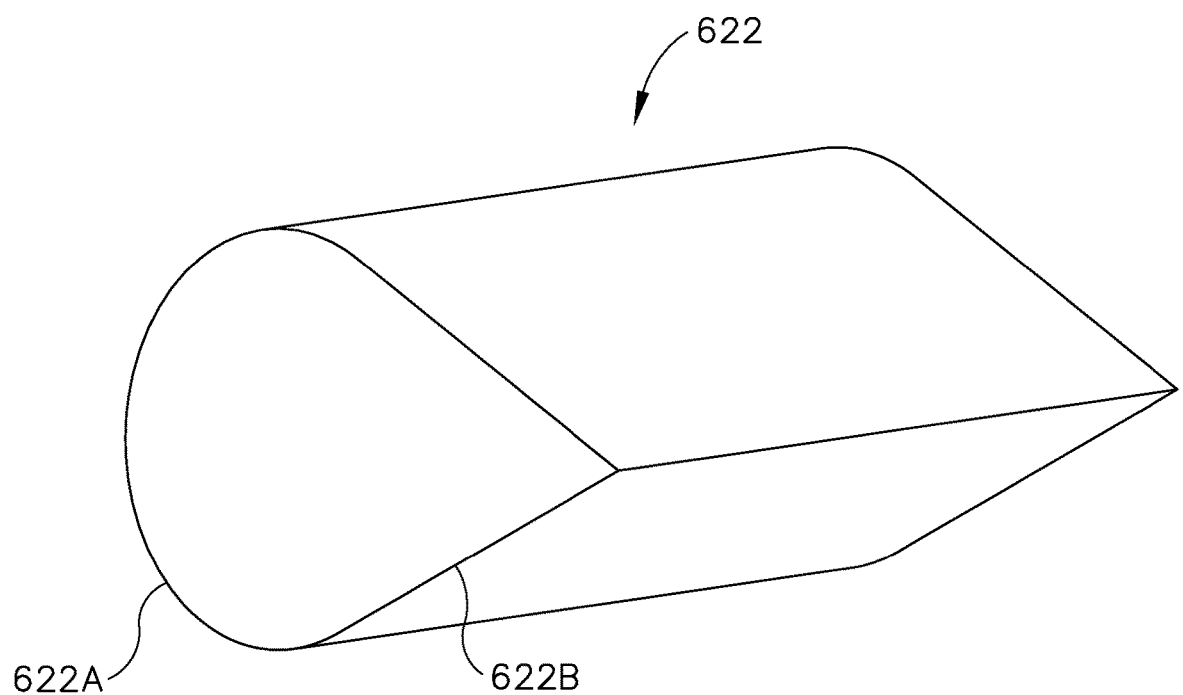
FIG. 42 depicts a perspective view of an exemplary pin of the pivoting cam mechanism of the instrument of FIG. 41A.

FIGS. 41A-42 show an exemplary clamp arm (620) and pivot pin (622) that may be readily incorporated into instrument (100). Clamp arm (620) is configured to operate substantially similar to clamp arm (144) discussed above except for the differences discussed below. In particular, clamp arm (620) is an integral feature of clamp arm assembly (150) and is pivotable toward and away from ultrasonic blade (142) based on pivoting of thumb grip ring (154) toward and away from body (122) of handle assembly (120). Pivot pin (622) is configured to operate substantially similar to pin (156) discussed above except for the differences discussed below. For instance, clamp arm assembly (150), including clamp arm (620), is pivotally coupled with outer sheath (132) via pin (622). Clamp arm (620) of the present example comprises a passageway (621) through which pin (622) passes to thereby pivotably couple clamp arm (620) with outer sheath (132). As best seen in FIGS. 41A-41C, passageway (621) comprises a circular profile, whereas, as best seen in FIG. 42, pin (622) comprises a teardrop-shaped profile. The teardrop-shaped profile of pin (622) includes a circular region (622A) and a substantially linear region (622B). Circular region (622A) is configured to bear against an interior surface of the circular profile of passageway (621), whereas a gap exists between the substantially linear region (622B) and the circular profile of passageway (621).

As previously discussed, clamp arm (620) and ultrasonic blade (142) are operable to clamp tissue. A portion of the force applied to this tissue via clamp arm (620) and ultrasonic blade (142) is transferred to pin (622). With clamp arm (620) in an open position, as shown in FIG. 41A, force applied to clamped tissue will be applied to circular region (622A) of pivot pin (622) via clamp arm (620) as represented by arrow (624) such that this force is incapable of moving clamp arm (620) upwardly or downwardly due to contact between circular region (622A) and the interior surface of the circular profile of passageway (621). With clamp arm (620) moved into a partially closed position, as shown in FIG. 41B, force applied to clamped tissue will be transmitted to circular region (622A) of pivot pin (622) via clamp arm (620), as represented by arrow (624), such that this force is incapable of moving clamp arm (620) upwardly or downwardly due to contact between circular region (622A) and the interior surface of the circular profile of passageway (621). With clamp arm (620) moved into a fully closed position, as shown in FIG. 41C, force applied to clamped tissue will be applied to linear region (622B) of pivot pin (622) via clamp arm (620), as represented by arrow (624), such that this force is capable of moving clamp arm (620) upwardly or downwardly due to clearance provided by the gap that exists between linear region (622A) and the interior surface of the circular profile of passageway (621). It should therefore be understood that in the fully closed position, clamp arm (620) may be moved upwardly and downwardly in a linear fashion relative to ultrasonic blade (142).

In some versions, pivot pin (622) is configured to allow end effector (140) to reach a full state of closure before clamp arm (620) may be moved upwardly and downwardly in a linear fashion relative to ultrasonic blade (142). In other words, clamp arm (620) may only move in a pivotal fashion relative to ultrasonic blade (142) when clamp arm (620) transitions from an open position to a closed position. Thus, the operator may first feel a hard stop when clamp arm (620) reaches the closed position, before clamp arm (620) may moves upwardly and downwardly in a linear fashion relative to ultrasonic blade (142). The operator may then continue to actuate clamp arm (620) further after reaching the closed position to provide additional linearly directed compression force on tissue captured between clamp arm (620) and ultrasonic blade. It should also be understood that the ultrasonic power delivered to ultrasonic blade (142) may be varied based on the state of closure of clamp arm (620).

Figure 43:
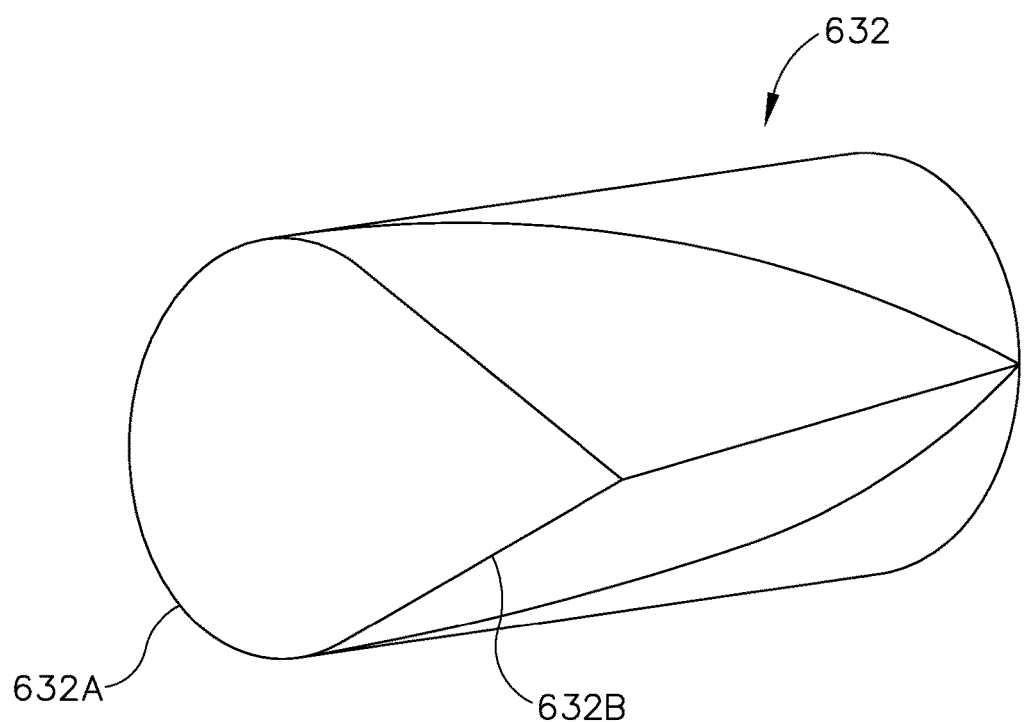
FIG. 43 depicts a perspective view of an exemplary alternative pin that may be used with the pivoting cam mechanism of the instrument of FIG. 41A.

FIG. 43 shows an exemplary alternative pin (632). A first end of pin (632) comprises a tear-shaped profile, whereas a second end of pin (632) comprises a circular profile. The tear-shaped profile of pin (632) includes a circular region (632A) and a substantially linear region (632B). It should be understood that the circular profile of pin (632) would provide a substantial gap between the circular profile and the interior surface of passageway (621). This substantial gap would allow for movement of clamp arm (620) in an upwardly and downwardly direction, as well as laterally relative to ultrasonic blade (142). This additional upward/downward movement and lateral movement may be provided after clamp arm (620) reaches a state of closure as described above, such that the additional upward/downward movement and lateral movement would be applied after tissue has been at least initially compressed between clamp arm (620) and ultrasonic blade.

While pins (622, 632) have been described as being incorporated into instrument (100), it should be understood that pins (622, 632) may alternatively be readily incorporated into instrument (10).

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
(a) a body assembly;
(b) a shaft assembly distally extending from the body assembly and including an acoustic waveguide;
(c) an ultrasonic blade distally extending from the shaft assembly and in acoustic communication with the acoustic waveguide;
(d) a clamp assembly including a clamp arm having a passageway surrounded by an interior surface extending therethrough; and
(e) a coupling assembly defining an axis and including a pin received within the passageway along the axis thereby operatively connecting the shaft assembly and the clamp arm, wherein a first portion of the pin is in contact with the interior surface, wherein a second portion of the pin and the interior surface define a gap therebetween, wherein the coupling assembly is configured to couple the clamp arm relative to the ultrasonic blade such that the clamp arm is configured to selectively move toward the ultrasonic blade from a first configuration through a second configuration toward a third configuration,
wherein the clamp arm is configured to pivot relative to the axis via the coupling assembly with selective movement from the first configuration toward the second configuration, and
wherein the clamp arm is configured to translate relative to the axis via the coupling assembly with selective movement from the second configuration toward the third configuration.

2. The surgical instrument of claim 1, wherein the first configuration is an open configuration of the clamp arm and the ultrasonic blade configured to receive a tissue, and wherein the second configuration is at least a partially closed configuration of the clamp arm and the ultrasonic blade.

3. The surgical instrument of claim 2, wherein the second configuration is a fully closed configuration of the clamp arm and the ultrasonic blade.

4. The surgical instrument of claim 1, wherein selective movement from the second configuration toward the third configuration reduces the gap.

5. The surgical instrument of claim 1, wherein the pin incudes a teardrop shaped surface, wherein the passageway includes a first circular surface, and wherein the teardrop shaped surface is received against the first circular surface.

6. The surgical instrument of claim 5, wherein the pin further includes a second circular surface.

7. The surgical instrument of claim 1, wherein the pin defines a first shape transverse to the axis, wherein the passageway defines a second shape transverse to the axis, and wherein the first shape is different than the second shape.

8. The surgical instrument of claim 1, wherein the axis is transverse to the distally extending ultrasonic blade.

9. The surgical instrument of claim 1, wherein the clamp arm is configured to pivot relative to the axis in a plane, wherein the clamp arm is configured to translate relative to the axis in the plane.

10. The surgical instrument of claim 9, wherein the clamp arm is configured to translate relative to the axis in the plane linearly toward the ultrasonic blade from the second configuration toward the third configuration.

11. The surgical instrument of claim 10, wherein the clamp arm is configured to move relative to the axis such that the clamp arm moves laterally from the plane relative to the ultrasonic blade from the second configuration toward the third configuration.

12. The surgical instrument of claim 1, wherein the clamp arm is configured to translate relative to the axis linearly toward the ultrasonic blade from the second configuration toward the third configuration.

13. The surgical instrument of claim 1, wherein at least a first portion of the pin has a teardrop shape.

14. The surgical instrument of claim 13, wherein at least a second portion of the pin has a circular shape.

15. The surgical instrument of claim 14, wherein the first portion is an end portion of the pin, and wherein the second portion is a central portion of the pin.

16. A method of compressing a tissue with a surgical instrument, the surgical instrument including (a) a body assembly; (b) a shaft assembly distally extending from the body assembly and including an acoustic waveguide; (c) an ultrasonic blade distally extending from the shaft assembly and in acoustic communication with the acoustic waveguide; (d) a clamp assembly including a clamp arm; and (e) a coupling assembly including a pin and defining an axis, wherein at least a first portion of the pin has a teardrop shape, wherein the coupling assembly is operatively connected to the shaft assembly and the clamp arm, wherein the coupling assembly is configured to couple the clamp arm relative to the ultrasonic blade such that the clamp arm is configured to selectively move toward the ultrasonic blade from a first configuration through a second configuration toward a third configuration, wherein the clamp arm is configured to pivot relative to the axis via the coupling assembly with selective movement from the first configuration toward the second configuration, and wherein the clamp arm is configured to translate relative to the axis via the coupling assembly with selective movement from the second configuration toward the third configuration, the method comprising:

(a) pivoting the clamp arm toward the ultrasonic blade to compress the tissue therebetween; and (b) translating the clamp arm toward the ultrasonic blade to further compress the tissue therebetween.

17. The method of claim 16, further comprising activating the ultrasonic blade after translating the clamp arm toward the ultrasonic blade.

18. A surgical instrument, comprising:

(a) a body assembly;

(b) a shaft assembly distally extending from the body assembly and including an acoustic waveguide;

(c) an ultrasonic blade distally extending from the shaft assembly and in acoustic communication with the acoustic waveguide;

(d) a clamp assembly including a clamp arm; and (e) a coupling assembly including a pin and defining an axis, wherein at least a first portion of the pin has a teardrop shape, wherein the coupling assembly is operatively connected to the shaft assembly and the clamp arm, wherein the coupling assembly is configured to couple the clamp arm relative to the ultrasonic blade such that the clamp arm is configured to selectively move toward the ultrasonic blade from a first configuration through a second configuration toward a third configuration, wherein the clamp arm is configured to pivot relative to the axis via the coupling assembly with selective movement from the first configuration toward the second configuration, and wherein the clamp arm is configured to translate relative to the axis via the coupling assembly with selective movement from the second configuration toward the third configuration.

19. The surgical instrument of claim 18, wherein at least a second portion of the pin has a circular shape.

20. The surgical instrument of claim 19, wherein the first portion is an end portion of the pin, and wherein the second portion is a central portion of the pin.

* * * * *